(12) United States Patent
Chen et al.

(10) Patent No.: US 12,350,262 B2
(45) Date of Patent: Jul. 8, 2025

(54) METHODS OF TREATMENT FOR CYSTIC FIBROSIS

(71) Applicant: Vertex Pharmaceuticals Incorporated, Boston, MA (US)

(72) Inventors: Weichao George Chen, San Diego, CA (US); Eric L Haseltine, Melrose, MA (US); Samuel Moskowitz, Waban, MA (US); Sarah Robertson, Somerville, MA (US); David Waltz, Waban, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 0 days.

(21) Appl. No.: 17/899,660

(22) Filed: Aug. 31, 2022

(65) Prior Publication Data

US 2023/0241045 A1   Aug. 3, 2023

Related U.S. Application Data

(63) Continuation of application No. 16/629,472, filed as application No. PCT/US2018/042486 on Jul. 17, 2018, now Pat. No. 11,517,564.

(60) Provisional application No. 62/657,508, filed on Apr. 13, 2018, provisional application No. 62/633,024, filed on Feb. 20, 2018, provisional application No. 62/623,748, filed on Jan. 30, 2018, provisional application No. 62/562,029, filed on Sep. 22, 2017, provisional application No. 62/533,392, filed on Jul. 17, 2017.

(51) Int. Cl.
| | |
|---|---|
| *A61K 31/4439* | (2006.01) |
| *A61K 31/404* | (2006.01) |
| *A61K 31/443* | (2006.01) |
| *A61K 31/47* | (2006.01) |
| *A61P 11/00* | (2006.01) |

(52) U.S. Cl.
CPC ........ *A61K 31/4439* (2013.01); *A61K 31/404* (2013.01); *A61K 31/443* (2013.01); *A61K 31/47* (2013.01); *A61P 11/00* (2018.01)

(58) Field of Classification Search
CPC .................................................. A61K 31/4439
USPC ...................................................... 514/341
See application file for complete search history.

(56) References Cited

U.S. PATENT DOCUMENTS

| | | |
|---|---|---|
| 5,410,061 A | 4/1995 | Gilmore et al. |
| 6,441,004 B1 | 8/2002 | Faull et al. |
| 6,787,651 B2 | 9/2004 | Stolle et al. |
| 6,949,572 B2 | 9/2005 | Bertinato et al. |
| 6,979,692 B2 | 12/2005 | Bertinato et al. |
| 7,368,573 B2 | 5/2008 | Bertinato et al. |
| 8,058,299 B2 | 11/2011 | Bolin et al. |
| 9,663,508 B2 | 5/2017 | Bregman et al. |
| 9,782,408 B2 | 10/2017 | Miller et al. |
| 9,981,910 B2 | 5/2018 | Altenbach et al. |
| 10,118,916 B2 | 11/2018 | Altenbach et al. |
| 10,131,670 B2 | 11/2018 | Strohbach et al. |
| 10,138,227 B2 | 11/2018 | Altenbach et al. |
| 10,208,053 B2 | 2/2019 | Strohbach et al. |
| 10,258,624 B2 | 4/2019 | Miller et al. |
| 10,570,115 B2 | 2/2020 | Alcacio et al. |
| 10,654,829 B2 | 5/2020 | Dhamankar et al. |
| 10,758,534 B2 | 9/2020 | Miller et al. |
| 10,793,547 B2 | 10/2020 | Abela et al. |
| 11,155,533 B2 | 10/2021 | Dhamankar et al. |
| 11,179,367 B2 | 11/2021 | Chu et al. |
| 11,186,566 B2 | 11/2021 | Alcacio et al. |
| 11,253,509 B2 | 2/2022 | Chen et al. |
| 11,414,439 B2 | 8/2022 | Abela et al. |
| 11,426,407 B2 | 8/2022 | Miller et al. |
| 11,434,201 B2 | 9/2022 | Angell et al. |
| 11,453,655 B2 | 9/2022 | Abela et al. |
| 11,465,985 B2 | 10/2022 | Angell et al. |
| 11,517,564 B2 | 12/2022 | Chen et al. |
| 12,168,009 B2 | 12/2024 | Miller et al. |
| 2002/0055631 A1 | 5/2002 | Augeri et al. |

(Continued)

FOREIGN PATENT DOCUMENTS

| | | |
|---|---|---|
| AU | 2013231151 A1 | 10/2013 |
| AU | 2013270464 A1 | 1/2014 |

(Continued)

OTHER PUBLICATIONS

Anilkumar, G.N. et al. (2011) "II. Novel HCV NS5B polymerase inhibitors: Discovery of indole C2 acyl sulfonamides" *Biogranic & Medicinal Chemistry Letters*, 22(1):713-717.

(Continued)

*Primary Examiner* — Taofiq A Solola
(74) *Attorney, Agent, or Firm* — Finnegan, Henderson, Farabow, Garrett & Dunner, LLP

(57) ABSTRACT

Compound I of the formula

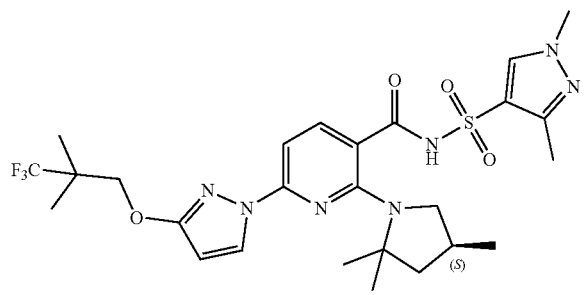

and/or pharmaceutically acceptable salt(s) of Compound I comprised in a pharmaceutical composition and methods of using the same to treat cystic fibrosis.

4 Claims, 15 Drawing Sheets

(56) References Cited

U.S. PATENT DOCUMENTS

| | | |
|---|---|---|
| 2002/0086887 A1 | 7/2002 | Augeri et al. |
| 2004/0006237 A1 | 1/2004 | Dolitzky et al. |
| 2005/0171185 A1 | 8/2005 | Yamasaki et al. |
| 2005/0197376 A1 | 9/2005 | Kayakiri et al. |
| 2007/0105833 A1 | 5/2007 | Ruah et al. |
| 2010/0160322 A1 | 6/2010 | Bruncko et al. |
| 2010/0227888 A1 | 9/2010 | Ruah et al. |
| 2011/0165118 A1 | 7/2011 | Chan et al. |
| 2013/0072483 A1 | 3/2013 | Zhong et al. |
| 2013/0267493 A1 | 10/2013 | Bhattacharya et al. |
| 2013/0317000 A1 | 11/2013 | Chowdhury et al. |
| 2013/0317001 A1 | 11/2013 | Andrez et al. |
| 2014/0080825 A1 | 3/2014 | Hadida-Ruah et al. |
| 2014/0296200 A1 | 10/2014 | Brown et al. |
| 2015/0320736 A1 | 11/2015 | Phenix et al. |
| 2015/0322002 A1 | 11/2015 | Dehnhardt et al. |
| 2016/0098585 A1 | 4/2016 | Sempere et al. |
| 2018/0099932 A1 | 4/2018 | Altenbach et al. |
| 2018/0141954 A1 | 5/2018 | Strohbach et al. |
| 2018/0170938 A1 | 6/2018 | Strohbach et al. |
| 2018/0244611 A1 | 8/2018 | Altenbach et al. |
| 2018/0244640 A1 | 8/2018 | Altenbach et al. |
| 2019/0055220 A1 | 2/2019 | Bear et al. |
| 2019/0077784 A1 | 3/2019 | Altenbach et al. |
| 2019/0153000 A1 | 5/2019 | Munoz et al. |
| 2019/0240197 A1 | 8/2019 | Chu et al. |
| 2019/0269683 A1 | 9/2019 | Miller et al. |
| 2020/0138798 A1 | 5/2020 | Chen et al. |
| 2020/0171015 A1 | 6/2020 | Haseltine et al. |
| 2020/0369608 A1 | 11/2020 | Angell et al. |
| 2020/0392109 A1 | 12/2020 | Dhamankar et al. |
| 2021/0032272 A1 | 2/2021 | Abela et al. |
| 2021/0052584 A1 | 2/2021 | Miller et al. |
| 2021/0069174 A1 | 3/2021 | Chu et al. |
| 2021/0113547 A1 | 4/2021 | Chen et al. |
| 2021/0139514 A1 | 5/2021 | Abela et al. |
| 2021/0228489 A1 | 7/2021 | Dokou et al. |
| 2022/0257564 A1 | 8/2022 | Chu et al. |
| 2022/0306606 A1 | 9/2022 | Alcacio et al. |
| 2023/0357191 A1 | 11/2023 | Abela et al. |
| 2024/0025877 A1 | 1/2024 | Angell et al. |

FOREIGN PATENT DOCUMENTS

| | | | |
|---|---|---|---|
| CA | 2145473 | A1 | 9/1995 |
| CN | 101087781 | A | 12/2007 |
| CN | 102458122 | A | 5/2012 |
| CN | 103946221 | A | 7/2014 |
| EA | 011074 | B1 | 12/2008 |
| EA | 28378 | B1 | 11/2017 |
| EP | 0 194 599 | A2 | 9/1986 |
| EP | 0 673 930 | A1 | 9/1995 |
| EP | 1 318 978 | B1 | 2/2006 |
| FR | 1335705 | A | 8/1963 |
| GB | 967177 | A | 8/1964 |
| IN | 201917015614 | | 7/2019 |
| IN | 201917024177 | | 8/2019 |
| JP | 10-114654 | A | 5/1998 |
| JP | 2007-511530 | A | 5/2007 |
| JP | 2008-524233 | A | 7/2008 |
| JP | 2011-520785 | A | 7/2011 |
| KR | 10-2005-0061501 | A | 6/2005 |
| RU | 2463303 | C2 | 10/2012 |
| RU | 2608610 | C2 | 1/2017 |
| TW | 201713617 | A | 4/2017 |
| WO | WO 91/015479 | A1 | 10/1991 |
| WO | WO 96/03380 | A1 | 2/1996 |
| WO | WO 96/22022 | A1 | 7/1996 |
| WO | WO 97/18712 | A1 | 5/1997 |
| WO | WO 97/22586 | A1 | 6/1997 |
| WO | WO 98/08818 | A1 | 3/1998 |
| WO | WO 98/31226 | A1 | 7/1998 |
| WO | WO 99/07351 | A2 | 2/1999 |
| WO | WO 99/16744 | A1 | 4/1999 |
| WO | WO 99/37153 | A1 | 7/1999 |
| WO | WO 99/41238 | A1 | 8/1999 |
| WO | WO 00/76969 | A1 | 12/2000 |
| WO | WO 01/08487 | A1 | 2/2001 |
| WO | WO 01/15533 | A1 | 3/2001 |
| WO | WO 01/39597 | A2 | 6/2001 |
| WO | WO 02/15902 | A1 | 2/2002 |
| WO | WO 02/24636 | A2 | 3/2002 |
| WO | WO 02/30895 | A1 | 4/2002 |
| WO | WO 02/085120 | A2 | 10/2002 |
| WO | WO 02/096883 | A1 | 12/2002 |
| WO | WO 03/002533 | A1 | 1/2003 |
| WO | WO 03/022050 | A1 | 3/2003 |
| WO | WO 03/028458 | A1 | 4/2003 |
| WO | WO 03/043423 | A1 | 5/2003 |
| WO | WO 03/043655 | A1 | 5/2003 |
| WO | WO 03/101959 | A1 | 12/2003 |
| WO | WO 03/103394 | A2 | 12/2003 |
| WO | WO 2004/021788 | A1 | 3/2004 |
| WO | WO 2004/021987 | A2 | 3/2004 |
| WO | WO 2004/037798 | A1 | 5/2004 |
| WO | WO 2004/039753 | A2 | 5/2004 |
| WO | WO 2004/043939 | A1 | 5/2004 |
| WO | WO 2004/046141 | A1 | 6/2004 |
| WO | WO 2004/056775 | A1 | 7/2004 |
| WO | WO 2004/056777 | A1 | 7/2004 |
| WO | WO 2004/078114 | A2 | 9/2004 |
| WO | WO 2004/085420 | A1 | 10/2004 |
| WO | WO 2004/111014 | A1 | 12/2004 |
| WO | WO 2005/049018 | A1 | 6/2005 |
| WO | WO 2005/054191 | A1 | 6/2005 |
| WO | WO 2005/070006 | A2 | 8/2005 |
| WO | WO 2005/075435 | A1 | 8/2005 |
| WO | WO 2005/080373 | A1 | 9/2005 |
| WO | WO 2005/085216 | A1 | 9/2005 |
| WO | WO 2005/099705 | A2 | 10/2005 |
| WO | WO 2005/108369 | A1 | 11/2005 |
| WO | WO 2006/002421 | A2 | 1/2006 |
| WO | WO 2006/030807 | A1 | 3/2006 |
| WO | WO 2006/039212 | A2 | 4/2006 |
| WO | WO 2006/065204 | A1 | 6/2006 |
| WO | WO 2006/066968 | A1 | 6/2006 |
| WO | WO 2006/067392 | A2 | 6/2006 |
| WO | WO 2007/019397 | A2 | 2/2007 |
| WO | WO 2007/021982 | A2 | 2/2007 |
| WO | WO 2007/053641 | A2 | 5/2007 |
| WO | WO 2007/075946 | A1 | 7/2007 |
| WO | WO 2007/079139 | A2 | 7/2007 |
| WO | WO 2007/087066 | A2 | 8/2007 |
| WO | WO 2007/113327 | A2 | 10/2007 |
| WO | WO 2007/117715 | A2 | 10/2007 |
| WO | WO 2007/134279 | A2 | 11/2007 |
| WO | WO 2008/005457 | A2 | 1/2008 |
| WO | WO 2008/100867 | A2 | 8/2008 |
| WO | WO 2008/127399 | A2 | 10/2008 |
| WO | WO 2008/141385 | A1 | 11/2008 |
| WO | WO 2009/006315 | A1 | 1/2009 |
| WO | WO 2009/027730 | A1 | 3/2009 |
| WO | WO 2009/032116 | A1 | 3/2009 |
| WO | WO 2009/038683 | A2 | 3/2009 |
| WO | WO 2009/064848 | A1 | 5/2009 |
| WO | WO 2009/071947 | A2 | 6/2009 |
| WO | WO 2009/073757 | A1 | 6/2009 |
| WO | WO 2009/076142 | A2 | 6/2009 |
| WO | WO 2009/127822 | A2 | 10/2009 |
| WO | WO 2009/138758 | A2 | 11/2009 |
| WO | WO 2010/003444 | A2 | 1/2010 |
| WO | WO 2010/007116 | A1 | 1/2010 |
| WO | WO 2010/019239 | A2 | 2/2010 |
| WO | WO 2010/022307 | A2 | 2/2010 |
| WO | WO 2010/025295 | A2 | 3/2010 |
| WO | WO 2010/048526 | A2 | 4/2010 |
| WO | WO 2010/053471 | A1 | 5/2010 |
| WO | WO 2010/054138 | A2 | 5/2010 |
| WO | WO 2010/065824 | A2 | 6/2010 |
| WO | WO 2010/078103 | A1 | 7/2010 |
| WO | WO 2010/083441 | A2 | 7/2010 |
| WO | WO 2010/102758 | A2 | 9/2010 |
| WO | WO 2010/108155 | A1 | 9/2010 |
| WO | WO 2010/108162 | A1 | 9/2010 |

(56) References Cited

FOREIGN PATENT DOCUMENTS

| | | |
|---|---|---|
| WO | WO 2010/110231 A1 | 9/2010 |
| WO | WO 2010/123822 A1 | 10/2010 |
| WO | WO 2010/138588 A2 | 12/2010 |
| WO | WO 2011/019413 A1 | 2/2011 |
| WO | WO 2011/068560 A1 | 6/2011 |
| WO | WO 2011/072241 A1 | 6/2011 |
| WO | WO 2011/102514 A1 | 8/2011 |
| WO | WO 2011/113894 A1 | 9/2011 |
| WO | WO 2011/116397 A1 | 9/2011 |
| WO | WO 2011/119984 A1 | 9/2011 |
| WO | WO 2011/127241 A2 | 10/2011 |
| WO | WO 2011/127290 A2 | 10/2011 |
| WO | WO 2011/128251 A1 | 10/2011 |
| WO | WO 2011/133751 A2 | 10/2011 |
| WO | WO 2011/133951 A1 | 10/2011 |
| WO | WO 2011/150016 A1 | 12/2011 |
| WO | WO 2012/027247 A2 | 3/2012 |
| WO | WO 2012/027731 A2 | 3/2012 |
| WO | WO 2012/052540 A1 | 4/2012 |
| WO | WO 2012/087938 A1 | 6/2012 |
| WO | WO 2012/089721 A1 | 7/2012 |
| WO | WO 2012/089722 A2 | 7/2012 |
| WO | WO 2012/102297 A1 | 8/2012 |
| WO | WO 2012/110519 A1 | 8/2012 |
| WO | WO 2012/116960 A1 | 9/2012 |
| WO | WO 2012/139891 A1 | 10/2012 |
| WO | WO 2012/158885 A1 | 11/2012 |
| WO | WO 2012/166415 A1 | 12/2012 |
| WO | WO 2012/170061 A1 | 12/2012 |
| WO | WO 2013/033068 A1 | 3/2013 |
| WO | WO 2013/037955 A1 | 3/2013 |
| WO | WO 2013/038373 A1 | 3/2013 |
| WO | WO 2013/038390 A1 | 3/2013 |
| WO | WO 2013/041602 A1 | 3/2013 |
| WO | WO 2013/070961 A1 | 5/2013 |
| WO | WO 2013/082102 A1 | 6/2013 |
| WO | WO 2013/112804 A1 | 8/2013 |
| WO | WO 2013/118805 A1 | 8/2013 |
| WO | WO 2013/130669 A1 | 9/2013 |
| WO | WO 2013/158121 A1 | 10/2013 |
| WO | WO 2013/177224 A1 | 11/2013 |
| WO | WO 2013/185112 A1 | 12/2013 |
| WO | WO 2013/185202 A1 | 12/2013 |
| WO | WO 2014/008458 A2 | 1/2014 |
| WO | WO 2014/014841 A1 | 1/2014 |
| WO | WO 2014/015841 A1 | 1/2014 |
| WO | WO 2014/015841 A2 | 1/2014 |
| WO | WO 2014/017093 A1 | 1/2014 |
| WO | WO 2014/028381 A1 | 2/2014 |
| WO | WO 2014/028968 A1 | 2/2014 |
| WO | WO 2014/039714 A2 | 3/2014 |
| WO | WO 2014/047427 A2 | 3/2014 |
| WO | WO 2014/0474727 A2 | 3/2014 |
| WO | WO 2014/071122 A1 | 5/2014 |
| WO | WO 2014/071247 A1 | 5/2014 |
| WO | WO 2014/071378 A1 | 5/2014 |
| WO | WO 2014/078842 A1 | 5/2014 |
| WO | WO 2014/086723 A1 | 6/2014 |
| WO | WO 2014/086739 A1 | 6/2014 |
| WO | WO 2014/086751 A1 | 6/2014 |
| WO | WO 2014/096388 A2 | 6/2014 |
| WO | WO 2014/109858 A1 | 7/2014 |
| WO | WO 2014/144100 A2 | 9/2014 |
| WO | WO 2014/152013 A1 | 9/2014 |
| WO | WO 2014/152018 A1 | 9/2014 |
| WO | WO 2014/180562 A1 | 11/2014 |
| WO | WO 2014/181287 A1 | 11/2014 |
| WO | WO 2014/190199 A1 | 11/2014 |
| WO | WO 2015/010832 A1 | 1/2015 |
| WO | WO 2015/031608 A1 | 3/2015 |
| WO | WO 2015/069287 A1 | 5/2015 |
| WO | WO 2015/073231 A1 | 7/2015 |
| WO | WO 2015/160787 A1 | 10/2015 |
| WO | WO 2016/057730 A1 | 2/2016 |
| WO | WO 2016/057572 A1 | 4/2016 |
| WO | WO 2016/081556 A1 | 5/2016 |
| WO | WO 2016/105484 A1 | 6/2016 |
| WO | WO 2016/105485 A2 | 6/2016 |
| WO | WO 2016/128529 A1 | 8/2016 |
| WO | WO 2016/160945 A1 | 10/2016 |
| WO | WO 2017/053455 A1 | 3/2017 |
| WO | WO 2017/053711 A2 | 3/2017 |
| WO | WO 2017/172802 A1 | 10/2017 |
| WO | WO 2017/173274 A1 | 10/2017 |
| WO | WO 2017/177124 A1 | 10/2017 |
| WO | WO 2017/187321 A1 | 11/2017 |
| WO | WO 2017/223188 A1 | 12/2017 |
| WO | WO 2018/064632 A1 | 4/2018 |
| WO | WO 2018/080591 A1 | 5/2018 |
| WO | WO 2018/081377 A1 | 5/2018 |
| WO | WO 2018/081378 A1 | 5/2018 |
| WO | WO 2018/081381 A1 | 5/2018 |
| WO | WO 2018/107100 A1 | 6/2018 |
| WO | WO 2018/116185 A1 | 6/2018 |
| WO | WO 2018/127130 A1 | 7/2018 |
| WO | WO 2018/183367 A1 | 10/2018 |
| WO | WO 2018/201126 A1 | 11/2018 |
| WO | WO 2018/227049 A1 | 12/2018 |
| WO | WO 2019/010092 A1 | 1/2019 |
| WO | WO 2019/018353 A1 | 1/2019 |
| WO | WO 2019/018395 A1 | 1/2019 |
| WO | WO 2019/028228 A1 | 2/2019 |
| WO | WO 2019/071078 A1 | 4/2019 |
| WO | WO 2019/079760 A1 | 4/2019 |
| WO | WO 2019/109021 A1 | 6/2019 |
| WO | WO 2019/113089 A1 | 6/2019 |
| WO | WO 2019/113476 A1 | 6/2019 |
| WO | WO 2019/152940 A1 | 8/2019 |
| WO | WO 2019/026075 A1 | 10/2019 |
| WO | WO 2019/191620 A1 | 10/2019 |
| WO | WO 2019/195739 A1 | 10/2019 |
| WO | WO 2019/200246 A1 | 10/2019 |
| WO | WO 2020/214921 A1 | 10/2020 |
| WO | WO 2020/242935 A1 | 12/2020 |
| WO | WO 2021/030552 A1 | 2/2021 |
| WO | WO 2021/030554 A1 | 2/2021 |

OTHER PUBLICATIONS

Atzrodt J, Derdau V, Fey T, Zimmermann J. "The Renaissance of H/D Exchange" Angew. Chem. Int. Ed. 2007: 46, 7744-7765.

Atzrodt J, Derdau V, Kerr W, Reid M. "C—H functionalization for hydrogen isotope exchange" Angew. Chem. Int. Ed. 2018: 57, 3022-3047.

Belikov, V.G., (2007) *Farmatsevticheskaya khimiya (Pharmaceutical Chemistry)*, Moscow: MEDpress- inform, pp. 27-29.

Bhattacharya, S. et al. (2009) Polymorphism in Pharmaceutical Solids: Thermoanalytical and Crystallographic Methods (Brittain H. ed., 2d ed. Informa Healthcare USA, Inc. 2009) 318-335.

Borhade, S.R. et al. (2013) "Synthesis of Novel Aryl and Heteroaryl Acyl Sulfonimidamides via Pd-Catalyzed Carbonylation Using a Nongaseous Precursor" *Organic Lett,* 15(5):1056-1059.

Boyle, M. "A CFTR corrector (lumacaftor) and a CFTR potentiator (ivacaftor) for treatment of patients with cystic fibrosis who have a phe508del CFTR mutation: a phase 2 randomised controlled trial," The Lancet Respiratory Medicine (Jul. 1, 2014) Retrieved from the Internet: https://www-clinicalkeycom-ez03.infotrieve.com/#!/content/playContent/1-s2.0S2213260014701328?returnurl=null&referrer=null.

Braman, V.; Liu, J. F.; Harbeson, S.; Uttamsingh, V.; Bridson, G.; Wu, L.; Shipley, J. E. "Preliminary Clinical Outcomes for CTP-354, a Novel Subtype-Selective GABA(A) Modulator" Presented at the American Neurological Association (ANA) 2014 Annual Meeting, Baltimore, MD, Oct. 12-14, 2014.

Brown et al. (2006) "On scaffolds and hopping in medicinal Chemistry," Mini-reviews in medicinal chemistry, vol. 6, 11(13), 1217-1229.

Byrn, S. et al. (1995) "Pharmaceutical solids: A strategic approach to regulatory considerations," (12): 945-954.

Caira, M. R. (1998) "Crystalline Polymorphism of Organic Compounds," *Topics in Current Chemistry,* 163-208.

(56) References Cited

OTHER PUBLICATIONS

Cargnin S, Serafini M, Pirali T. "A primer of deuterium in drug design" Future Med. Chem. 2019; 11(16): 2039-2042.
Chemical Abstracts Service, CAS Registry No. 204017-11-8. CA Index Name: 1H-Indole-2-carboxamide, 1-[[2,4-bis(trifluoromethyl)phenyl]methyl]-2,3-dihydro-N-(phenylsulfonyl)-. Entered STN: Apr. 12, 1998.
Chemical Abstracts Service, CAS Registry No. 220678-97-7. CA Index Name: 1H-Indole-2-carboxamide, 1-[(3,4-dichlorophenyl)methyl]-N-(phenylsulfonyl)-. Entered STN: Mar. 24, 1999.
Chemical Abstracts Service, CAS Registry No. 220678-99-9. CA Index Name: 1H-Indole-2-carboxamide, 1-[(3,4-dichlorophenyl)methyl]-N-[(3,5-dimethyl-4-isoxazolyl)sulfonyl]-. Entered STN: Mar. 24, 1999.
Chemical Abstracts Service, CAS Registry No. 412005-98-2. CA Index Name: 1H-Indole-2-carboxamide, 3-(4-methoxyphenyl)-N-(phenylsulfonyl)-1-[[3-(trifluoromethyl)phenyl]methyl]-. Entered STN: May 7, 2002.
Chemical Abstracts Service, CAS Registry No. 895575-67-4. CA Index Name: 1H-Indole-2-carboxamide, 1-[(3-chlorophenyl) methyl]-4-nitro-N-(2-thienylsulfonyl)-. Jun. 30, 2006.
Chemical Abstracts Service, CAS Registry No. 895575-68-5. CA Index Name: 1H-Indole-2-carboxamide, 4-amino-1-[(3-chlorophenyl)methyl]-N-(2-thienylsulfonyl)-. Jul. 23, 2006.
Chen, Y. (Jan. 2, 20166) "N-Monoacylation of Sulfonimidamides" *Synthesis*, 48(7):1019-1028.
Czeskis B, Elmore, CS, Haight A, Hesk D, Maxwell BD, Miller SA, Raglione T, Schildknegt K, Traverse JF, Wang P. "Deuterated active pharmaceutical ingredients: A science-based proposal for synthesis, analysis, and control. Part 1: Framing the problem" J. Label. Compd. Radiopharm. 2019, 62: 690-694. DOI: 10.1002/jlcr.3743.
Dao HT, Li C, Michaudel Q, Maxwell BD, Baran PS. J. Am. Chem. Soc. 2015; 137, 8046-8049.
Database CAPLUS, Accession No. 1965:51408. Abstract of French Patent No. FR M2868, filed Nov. 23, 1964, by Roussel-UCLAF [online]. Retrieved Jan. 6, 2017 (1 page).
Database CAPLUS, Accession No. 1965:51409. Abstract of German Patent No. DE 1182243, filed Nov. 26, 1964, by Badische Anilin & Soda-Fabrik A.G. [online]. Retrieved Jan. 6, 2017 (2 pages).
Database ChemSpider, CSID:17283620 (CAS: RN 1026625-71-7), http://www.chemspider.com/Chemical-Structure.17283620.html (accessed 16:40, Mar. 30, 2023).
Database PUBCHEM, CID: 44419393. Compound Summary, CHEMBL374189. NIH, U.S. National Library of Medicine, National Center for Biotechnology Information; Modify Date: Jan. 16, 2016. [online]. Retrieved from https://pubchem.ncbi.nlm.nih.gov/compound/44419393, on Jan. 22, 2016 (11 pages).
Database PUBCHEM, CID: 49774135. Compound Summary, SCHEMBL13395127. NIH, U.S. National Library of Medicine, National Center for Biotechnology Information; Modify Date: Jan. 16, 2016 [online]. Retrieved from https://pubchem.ncbi.nlm.nih.gov/compound/49774135, on Jan. 22, 2016 (10 pages).
Database PUBCHEM, CID: 58132855. Compound Summary, SCHEMBL831192. NIH, U.S. National Library of Medicine, National Center for Biotechnology Information, PubChem Open Chemistry Database; Modify Date: Jan. 16, 2016 [online]. Retrieved from: https://pubchem.ncbi.nlm.nih.gov/compound/58132855, on Jan. 22, 2016 (10 pages).
Database PUBCHEM, CID: 20050716. Compound Summary, 1-[2-[[2-[(2-Amino-3-methylbutanoyl)amino]-3-methylpentanoyl]amino]-3-phenylpropanoyl]pyrrolidine-2-carboxylic acid. NIH, U.S. National Library of Medicine, National Center for Biotechnology Information; Modify Date: Nov. 30, 2019. [online]. Retrieved from https://pubchem.ncbi.nlm.nih.gov/compound/20050716, on Dec. 3, 2019 (7 pages).
Database PUBCHEM, CID: 20091118. Compound Summary, [4-(5-Hexylpyrimidin-2-yl)phenyl] 2-methoxypropanoate. NIH, U.S. National Library of Medicine, National Center for Biotechnology Information; Modify Date: Nov. 30, 2019. [online]. Retrieved from https://pubchem.ncbi.nlm.nih.gov/compound/20091118, on Dec. 3, 2019 (9 pages).
Database PUBCHEM, CID: 20120819. Compound Summary, 4-(Cyclopentyloxy)-3-fluorobenzene-1-sulfonyl chloride. NIH, U.S. National Library of Medicine, National Center for Biotechnology Information; Modify Date: Nov. 30, 2019. [online]. Retrieved from https://pubchem.ncbi.nlm.nih.gov/compound/20120819, on Dec. 3, 2019 (8 pages).
Database PUBCHEM, CID: 2545578. Compound Summary, T5339296. NIH, U.S. National Library of Medicine, National Center for Biotechnology Information; Modify Date: Jan. 16, 2016. [online]. Retrieved from https://pubchem.ncbi.nlm.nih.gov/compound/2545578, on Jan. 22, 2016 (9 pages).
Dorwald, F. A. (2006) "Side Reactions in Organic Synthesis" Wiley: VCH, Weinheim p. IX of Preface p. 1-15.
European Patent Application No. 15849396.5 (Patent No. 3203840): Notice of Opposition by Elkington and Fife, LLP, May 5, 2021 (19 pages).
Gant TG. "Using Deuterium in Drug Discovery: Leaving the Label in the Drug" J Med. Chem. 2014; 57(9): 3595-3611.
Garg, V. et al. "Pharmacokinetic and Drug-Drug Interaction Profiles of the Combination of Tezacaftor/Ivacaftor", Clinical and Translational Science—CTS, vol. 12, No. 3, Jan. 29, 2019 (Jan. 29, 2019), pp. 267-275, XP055719490, US ISSN: 1752-8054, DOI: 10.1111/cts.12610.
Ghose et al. (1999) Knowledge-based approach in designing combinatorial or medicinal chemistry libraries for drug discovery—qualitive and quantitative characterization of known drug databases, *J. Comb. Chem.* 1(1), 55-68.
Halford B. "The deuterium switcheroo" Chemical & Engineering News 2016; 94(27), 32-36.
Hopkins, C.R. et al. (2006) "Design and synthesis of novel N-sulfonyl-2-indole carboxamides as potent PPAR-gamma binding agents with potential application to the treatment of osteoporosis" Bioorganic & Medicinal Chemistry Letters, 16(21):5659-5663.
International Patent Application No. PCT/US2015/54316: International Search Report and Written Opinion, mailed Feb. 5, 2016 (11 pages).
International Patent Application No. PCT/US2017/025381: International Search Report and Written Opinion, mailed Jun. 6, 2017 (11 pages).
International Patent Application No. PCT/US2017/054611: International Search Report and Written Opinion, mailed Jan. 3, 2018 (10 pages).
International Patent Application No. PCT/US2017/065425: International Search Report and Written Opinion, mailed Feb. 27, 2018 (10 pages).
International Patent Application No. PCT/US2018/036610: International Search Report and Written Opinion, mailed Sep. 19, 2018 (9 pages).
International Patent Application No. PCT/US2018/040427: International Search Report and Written Opinion, mailed Oct. 9, 2018 (15 pages).
International Patent Application No. PCT/US2018/042415: International Search Report and Written Opinion, mailed Oct. 31, 2018 (12 pages).
International Patent Application No. PCT/US2018/042486: International Search Report and Written Opinion, mailed Nov. 7, 2018 (13 pages).
International Patent Application No. PCT/US2018/044963: International Search Report and Written Opinion, mailed Sep. 25, 2018 (15 pages).
International Patent Application No. PCT/US2018/056772: International Search Report and Written Opinion, mailed Jan. 29, 2019 (13 pages).
International Patent Application No. PCT/US2018/063871: International Search Report and Written Opinion, mailed Feb. 25, 2019 (16 pages).
International Patent Application No. PCT/US2018/064522: International Search Report and Written Opinion, mailed Jun. 25, 2019 (21 pages).

(56) References Cited

OTHER PUBLICATIONS

International Patent Application No. PCT/US2019/016537: International Search Report and Written Opinion, mailed Apr. 23, 2019 (13 pages).
International Patent Application No. PCT/US2019/018042: International Search Report and Written Opinion, mailed Apr. 17, 2019 (10 pages).
International Patent Application No. PCT/US2019/024890: International Search Report and Written Opinion, mailed Jun. 17, 2019 (13 pages).
International Patent Application No. PCT/US2019/026075: International Search Report and Written Opinion, mailed Jun. 17, 2019 (13 pages).
International Patent Application No. PCT/US2019/027202: International Search Report and Written Opinion, mailed Jun. 17, 2019 (10 pages).
International Patent Application No. PCT/US2020/028699: International Search Report and Written Opinion, mailed Jul. 20, 2020 (9 pages).
International Patent Application No. PCT/US2020/034199: International Search Report and Written Opinion, mailed Aug. 11, 2020 (15 pages).
Ivanisevic, I. (2011) "Uses of X-Ray Powder Diffraction in the Pharmaceutical Industry," Pharm. Form. Qual. 30-33.
Jain, B.C. et al. (1947) "Studies in Sulphanilamides. Part XIII. Reaction With Dicarboxylic Acids. Some New N1- and N4-Acyl and Heterocyclic Derivatives" *Journal of the Indian Chemical Society*, 24:173-176.
Kettle, J.G. et al. (2004) "N-Benzylindole-2-carboxylic acids: potent functional antagonists of the CCR2b chemokine receptor" *Bioorganic & Medicinal Chemistry Letters*, 14(2): 405-408.
Kieltsch, I. et al. Laureates: Awards and Honors SCS Fall Meeting 2007 260 Recent Advances in Electrophilic CF 3-Transfer Using Hypervalent Iodine(III) Reagents 11, A Chimia Chimia Schweizerische Chemische Gesellschaft ISSN, vol. 62, No. 62, Jan. 1, 2008 (Jan. 1, 2008), pp. 260-263, XP055591571, DOI: 10.2533/chimia.2008.260.
Kholodov, L.E. et al., Klinicheskaya farmakokinetika (Clinical Pharmacokinetics), M., Meditsina, 1985, pp. 83-98, 134-138, 160, 378-380.
Kola et al. (2004) "Can the pharmaceutical industry reduce attrition rates?" Nature Reviews Drug Discovery, 3(8), 711-715.
Kratkiy kurs molekulyarnoy biologii (A Concise Course in Molecular Biology), edited by P.V. Sergeev, M., 1975, p. 10.
Lai, J.T. et al. (1980) "Rearrangement of 2,2,6,6-tetramethyl-4-piperidone in phase-transfer catalyzed reactions," *Journal of Organic Chemistry*, 45(8):1513-1514.
Liu, J. F. et al. "CTP-354: A Novel Deuterated Subtype-Selective GABA(A) Modulator for Treatment of Neuropathic Pain, Spasticity and Anxiety Disorders" Presented at the American College of Neuropsychopharmacology (ACNP) 51st Annual Meeting, Hollywood, FL, Dec. 2-6, 2012.
Matter, H. et al. (2002) "Design and Quantitative Structure-Activity Relationship of 3-Amidinobenzyl-1H-indole-2-carboxamides as Potent, Nonchiral, and Selective Inhibitors of Blood Coagulation Factor Xa" *Journal of Medicinal Chemistry*, 45(13):2749-2769.
Maxwell BD, Tran SB, Lago M, Li J, and Bonacorsi Jr SJ. "The syntheses of [14C]BMS-823778 for use in a human ADME clinical study and of [13CD313CD2]BMT-094817, a stable-isotope labeled standard of a newly detected human metabolite" J. Label. Compd. Radiopharm. 2016; 59, 255-259.
Montemayor, Kristina et al. "Unmasking catamenial hemoptysis in the era of CFTR modulator therapy", Journal of Cystic Fibrosis, Elsevier, NL, vol. 19, No. 4, Jan. 24, 2020 (Jan. 24, 2020), XP086202454, ISSN: 1569-1993, DOI: 10.1016/J.JCF.2020.01.005 [retrieved on Jan. 24, 2020].
NCT03029455 "A Study to Evaluate Safety and Pharmacokinetics of VX-659 in Healthy Subjects and in Adults With Cystic Fibrosis". Vertex Pharmaceuticals Incorporated, Retrieved from the Internet: https://clinicaltrials.gov/ct2/show/study/NCT03029455.
Norman, P. (2014) "Novel picolinamide-based cystic fibrosis transmembrane regulator modulators: evaluation of WO2013038373, WO2013038376, WO2013038381, WO2013038386, and WO2013038390," *Expert Opinion on Therapeutic Patents*, 24(7):829-837.
Notman, N. (2016) "2Heavy drugs gaining momentum" [online] Retrieved from the internet: https://www.chemistryworld.com/features/2heavy-drugs-gaining-momentum/1010186.article, on Oct. 7, 2019.
Passarella, D. et al. (2001) "Cyclodimerization of indol-2-ylacetylenes. An example of intermolecular enyne-alkyne cycloaddition" *Journal of the Chemical Society, Perkin Transactions 1*, 127-129.
Pham, P. et al. (2011) "Photoredox Catalysis: A Mild, Operationally Simple Approach to the Synthesis of alpha-Trifluoromethyl Carbonyl Compounds" Angew. Chem. Int. Ed. 2011:50 6119-6122.
Pirali T, Serafini M, Cargnin S, Genazzani AA. "Applications of Deuterium in Medicinal Chemistry" J Med. Chem. 2019; 62(11): 5276-5297.
Qun, C. et al. "Synthesis of 3,3,3-trifluoro-2,2-dimethylpropionic acid", Huaxue Shiji—Chemical Reagents, Beijing : Huaxue Huaxue Shiji Keji Qingbao Zhongxinzhan, CN, vol. 38, No. 4, Jan. 1, 2016 (Jan. 1, 2016), pp. 386-388, XP009513488, ISSN: 0258-3283, DOI: 10.13822/J.CNKI.HXSJ.2016.04.026.
Rosebraugh, C.J. (2015) "Highlights of Prescribing Information for Orkambi," [online] Retrieved from the Internet: https://www.accessdata.fda.gov/drugsatfda_docs/label/2015/206038Orig1s000lbl.pdf, on Aug. 24, 2017.
Schmidt C. "First deuterated drug approved" Nat. Biotechnol. 2017, 35, 493-494.
Shih et al. (2010) "Pyrazole compound BPR1P0034 with potent and selective anti-influenza virus activity" Journal of Biomedical Science, 17:13.
Silverman, R. (2004) The Organic Chemistry of Drug Design and Drug Action, Elsevier, pp. 29-32.
Soloducho, J. (1989) "Synthesis of Some Pyrido [2,3-c][1,2,6]triazinone Derivatives" *Journal für Pracktische Chemie*, 331(3):503-506.
Soloducho, J. et al. "Synthesis of Some Pyrido[3,2g][1,2,5]triazocine Derivatives," *Polish Journal of Chemistry*, vol. 59, No. 10-12, Jan. 1, 1985, pp. 1115-1120.
Table 2 : List of the mutations or SNP tested in this study (https://www.jmdjournal.org/cms/10.2353/jmoldx.2008.080056/attachment/2286a276-d0b2-4a8a-83f8-8273bef9a761/mmc1.doc). Accessed Jan. 25, 2021.
Tsong-Long H. et al. "Synthesis and pharmacological characterization of 2-aminobenzaldehyde oxime analogs as dual inhibitors of neutrophil elastase and proteinase 3", Bioorganic & Medicinal Chemistry, vol. 23, No. 5, Jan. 16, 2015, pp. 1123-1134, XP029199003.
Tullis, E. et al. (2018) "Preliminary safety and efficacy of triple-combination CFTR modulator regimens," *Respirology*, 23(51):33.
Uttamsingh, V. et al. (2016) "WS13.6 CTP-656 tablet confirmed superiority of pharmacokinetic profile relative to Kalydeco in Phase I clinical studies" *Journal of Cystic Fibrosis*, 15:S22.
Venkatesh, S. et al. (2000) "Role of the development scientist in compound lead selection and optimization" *J. Pharm. Sci.* 89(2), 145-154.
Verado, G. et al. (1999) "Reductive One Batch Synthesis of N-Substituted Pyrrolidines from Primary Amines and 2,5-Dimethoxytetrahydrofuran" *Synthesis*, (1):74-79.
Vertex Pharmaceuticals, Inc. (Jul. 18, 2017) "Vertex Announces Positive Phase 1 & Phase 2 Data from Three Different Triple Combination Regimens in People with Cystic Fibrosis Who Have One F508del Mutation and One Minimal Function Mutation (F508del/Min)", Retrieved from the Internet: URL: http://investors.vrtx.com/news-releases/news-release-details/vertex/announces-positive-phase-1-phase-2-data-three-different [retrieved on Mar. 27, 2019].
Vertex Pharmaceuticals, Inc. (Mar. 28, 2017) "Two Phase 3 Studies of the Tezacaftor/Ivacaftor Combination Treatment Met Primary Endpoints with Statistically Significant Improvements in Lung Function (FEV1) in People With Cystic Fibrosis" [online] Retrieved from the Internet: http://investors.vrtx.com/static-files/f15217ac-4a8b-436a-9215-79144ec2e59b, on Oct. 10, 2019.

(56) References Cited

OTHER PUBLICATIONS

Vertex Pharmaceuticals, Inc. (Nov. 3, 2017) "Vertex announces presentations of data at North American Cystic Fibrosis Conference that Demonstrate Important Progress Toward Goal of Helping All People with CF," Health and Medicine Week, vol. 3, p. 196.
"Vertex Provides Update on Ongoing Phase 3 Program for VX-661 in Combination with Ivacaftor for the Treatment of Cystic Fibrosis" (Aug. 15, 2016) Retrieved from the Internet: https://www.businesswire.com/news/home/20160815006099/en/Vertex-Update-Ongoing-Phase-3-Program-VX-661.
Vodak, D. (2014) "Design and Development of HPMCAS-Based Spray-Dried Dispersions," 303-322.
Wainwright, C.E. et al. (2015) "Lumacaftor-Ivacaftor in Patients with Cystic Fibrosis Homozygous for Phe508del CFTR," *The New England Journal of Medicine,* 373(3):220-231.
Walters et al. (2002) "Prediction of 'drug-likeness'," Advanced Drug Delivery Reviews, 54(3), 255-271.
Willson T. M. et al. (1996) "Bone targeted drugs 2. Synthesis of estrogens with hydroxyapatite affinity," Bioorg. & Med. Chem. Lett., (6):1047-1050.
Winn, M. et al. (1993) "2-(Alkylamino)nicotinic Acid and Analogs. Potent Angiotensin II Antagonists" *Journal of Medicinal Chemistry,* 36(18):2676-2688.
Yarnell AT. "Heavy-Hydrogen Drugs Turn Heads, Again" Chemical & Engineering News 2009; 87(25), 36-39.
Anonymous: "Highlights of Prescribing Information—TRIKAFTA," Jun. 1, 2021, pp. 1-18, Retrieved from the internet: URL:https://www.accessdata.fda.gov/drugsat fda_docs/label/2021/212273s004lbl.pdf [retrieved on Nov. 13, 2023].
Bartlett, P.A. and Entzeroth, M. (2006) "Exploiting Chemical Diversity for Drug Discovery," The Royal Society of Chemistry, pp. 113-118.
Bhujbal, Sonal et al. (2021) "Pharmaceutical amorphous solid dispersion: A review of manufacturing strategies," Acta Pharmaceutica Sinica B, vol. 11, No. 8, pp. 2505-2536.
Chou, Ting-Chao, Drug Combination Studies and Their Synergy Quantification Using the Chou-Talalay Method, Cancer Res; 70(2), 2010, pp. 440-446).
Dyson G., May P., Khimiya sinteticheskikh lekarstvennykh veshchestv (Chemistry of Synthetic Drugs), translation from English—M.: Mir, 1964, pp. 12-19).
"Find ETDs Home » Thesis Resources » Find ETDs" Online: "https://ndltd.org/thesis-resources/find-etds/" Accessed Jan. 31, 2023.
Grootenhuis, P. et al. Vertex Pharmaceuticals Incorporated, Boston, MA, USA, Discovery and Biological Profile of Next-Generation CFTR Correctors, 188, Pediatr Pulmonol. Oct. 2016; 51 (Suppl 45):S194-S485, Published online Sep. 21, 2016. doi: https://www.ncbi.nlm.nih.gov/pmc/articles/PMC7159391/.
Irwin, J. J. and Shoichet, B. K. (2005) "ZINC—A Free Database of Commercially Available Compounds for Virtual Screening," *J. Chem. Inf. Model.* 45, 177-182.

Kharkevich, D.A. Farmakologiya (Pharmacology)/ Textbook, 10th edition, pp. 72-82).
Kim, S. et al. (2021) "PubChem in 2021: new data content and improved web interfaces," Nucleic Acids Research, 49, D1388-D1395.
Masjhkovskiy, M.D. Lekarstvennye sredstva (Medicaments), Moscow, Meditsina, 1993, part 1, p. 8).
Meoli, A et al. State of the Art on Approved Cystic Fibrosis Transmembrane Conductance Regulator (CFTR) Modulators and Triple-Combination Therapy, Pharmaceuticals 2021, 14(9), 928; https://doi.org/10.3390/ph14090928, Published: Sep. 15, 2021, https://www.mdpi.com/1424-8247/14/9/928#sec4-pharmaceuticals-14-00928.
Notice of Allowance and Fee(s) Due for U.S. Appl. No. 17/865,220, mailed Apr. 19, 2024.
Patel, Kaushika et al. (2022) "Solid dispersion technology as a formulation strategy for the fabrication of modified release dosage forms: A comprehensive review," Daru Journal of Pharmaceutical Sciences, Biomed Central Ltd, London, UK, vol. 30, No. 1, pp. 165-189.
Pedemonte, N. et al. (2005) "Phenylglycine and Sulfonamide Correctors of Defective F508del and G551D Cystic Fibrosis Transmembrane Conductance Regulator Chloride-Channel Gating" Molecular Pharmacology vol. 67, No. 5, 1797-1807.
PubChem-44419393 Create Date: Nov. 19, 2009.
PubChem-58132855 Create Date: Aug. 19, 2012.
PubChem-2545578 Create Date Jul. 16, 2005.
PubChem-49774135 Create Date Dec. 2, 2010.
Registry/ZRegistry (CAS RegistrySM), Sep. 2016, 2 pages.
Rossiiskii terapeuticheskii spravochnik [Russian therapeutic reference book], second edition, ed. Acad. RAMS A.G. Chuchalina, M. 2008, p. 144.
Vertex Pharmaceuticals, Inc. (Jul. 18, 2017) "A Study Evaluating the Safety and Efficacy of VX-659 Combination Therapy in Subjects with Cystic Fibrosis," Study NCT03224351, ClininalTrials.gov.
Anonymous: "Highlights of Prescribing Information—TRIKAFTA," Aug. 3, 2023, pp. 1-19, Retrieved from internet: URL: https://www.accessdata.fda.gov/drugsatfda_docs/label/2023/212273s011,217660s002lbl.pdf [retrieved on Dec. 16, 2024].
Dwivedi, G. et al. (2010) "Evergreening: A deceptive device in patent rights," Technology in Society, 32: 324-330.
Feldman, R. (2022) "Understanding 'Evergreening': Making Minor Modifications of Existing Medications to Extend Protections, Health Affairs" 41:(6), 801-804.
Maharramov, A. M. et al. (2016) "Activation of Covalent Bonds Through Non-Covalent Interactions," Non-covalent Interactions in the Synthesis and Design of New Compounds, Chapter 1, pp. 1-20, John Wiley & Sons, Inc.
Verkman, A.S. et al. (2006) "CFTR Chloride Channel Drug Discovery—Inhibitors as Antidiarrheals and Activators for Therapy of Cystic Fibrosis," 12(18): 2235-2247.

FIG. 6

| Mutation cDNA Name | Mutation Protein Name | Mutation Legacy Name |
|---|---|---|
| c.1A>G | p.? (unknown) | M1V |
| c.54-5940_273+10250del21kb | p.Ser18ArgfsX16 | CFTRdele2,3 |
| c.91C>T | p.Arg31Cys | R31C |
| c.115C>T | p.Gln39X | Q39X |
| c.137C>A | p.Ala46Asp | A46D |
| c.165-1G>A | No protein name | 297-1G->A |
| c.166G>A | p.Glu56Lys | E56K |
| c.174_175insA | p.Arg59LysfsX10 | 306insA |
| c.178G>T | p.Glu60X | E60X |
| c.200C>T | p.Pro67leu | P67L |
| c.220C>T | p.Arg74Trp | R74W |
| c.223C>T | p.Arg75X | R75X |
| c.224G>A | p.Arg75Gln | R75Q |
| c.254G>A | p.Gly85Glu | G85E |
| c.262_263delTT | p.Leu88IlefsX22 | 394delTT |
| c.273+1G>A | No protein name | 405+1G->A |
| c.274-1G>A | No protein name | 406-1G->A |
| c.274G>A | p.Glu92Lys | E92K |
| c.274G>T | p.Glu92X | E92X |
| c.292C>T | p.Gln98X | Q98X |
| c.313delA | p.Ile105SerfsX2 | 444delA |
| c.325_327delTATinsG | p.Tyr109GlyfsX4 | 457TAT->G |
| c.328G>C | p.Asp110His | D110H |
| c.349C>T | p.Arg117Cys | R117C |
| c.350G>A | p.Arg117His | R117H |
| c.366T>A | p.Tyr122X | Y122X |
| c.442delA | p.Ile148LeufsX5 | 574delA |
| c.443T>C | p.Ile148Thr | I148T |

FIG. 6 (continued)

| Mutation cDNA Name | Mutation Protein Name | Mutation Legacy Name |
|---|---|---|
| c.489+1G>T | No protein name | 621+1G->T |
| c.531delT | p.Ile177MetfsX12 | 663delT |
| c.532G>A | p.Gly178Glu | G178R |
| c.543_546delTAGT | p.Leu183PhefsX5 | 675del4 |
| c.579+1G>T | No protein name | 711+1G->T |
| c.579+3A>G | No protein name | 711+3A->G |
| c.579+5G>A | No protein name | 711+5G->A |
| c.580-1G>T | No protein name | 712-1G->T |
| c.595QT | p.His199Tyr | H199Y |
| c.613CM | p.Pro205Ser | P205S |
| c.617T>G | p.Leu206Trp | L206W |
| c.658QT | p.Gln220X | Q220X |
| c.680T>G | p.Leu227Arg | L227R |
| c.720_741delAGGGAGAATGATGATGAAGTAC | p.Gly241GlufsX13 | 852del22 |
| c.828C>A | p.Cys276X | C276X |
| c.948delT | p.Phe316LeufsX12 | 1078delT |
| c.988G>T | p.Gly330X | G330X |
| c.1000C>T | p.Arg334Trp | R334W |
| c.1007T>A | p.Ile336Lys | I336K |
| c.1013C>T | p.Thr338Ile | T338I |
| c.1021T>C | p.Ser341Pro | S341P |
| c.1022_1023insTC | p.Phe342HisfsX28 | 1154insTC |
| c.1040G>A | p.Arg347His | R347H |
| c.1040G>C | p.Arg347Pro | R347P |
| c.1055G>A | p.Arg352Gln | R352Q |
| c.[1075C>A; 1079C>A] | p.[Gln359Lys;Thr360Lys] | Q359K/T360K |
| c.1081delT | p.Trp361GlyfsX8 | 1213delT |
| c.1116+1G>A | No protein name | 1248+1G->A |
| c.1127_1128insA | p.Gln378AlafsX4 | 1259insA |
| c.1153_1154insAT | p.Asn386IlefsX3 | 1288insTA |

FIG. 6 (continued)

| Mutation cDNA Name | Mutation Protein Name | Mutation Legacy Name |
|---|---|---|
| c.1202G>A or c.1203G>A | p.Trp401X | W401X |
| c.1209+1G>A | No protein name | 1341+1G->A |
| c.1210-12[5] | No protein name | 5T |
| c.1210-12[7] | No protein name | 7T |
| c.1240C>T | p.Gln414X | Q414X |
| c.1329_1330insAGAT | p.Ile444ArgfsX3 | 1461ins4 |
| c.1340delA | p.Lys447ArgfsX2 | 1471delA |
| c.1364C>A | p.Ala455Glu | A455E |
| c.1393-1G>A | No protein name | 1525-1G->A |
| c.1397C>A or c.1397C>G | p.Ser466X | S466X |
| c.1400T>C | p.Leu467Pro | L467P |
| c.1408A>G | p.Met470Val | M470V |
| c.1418delG | p.Gly473GlufsX54 | 1548delG |
| c.1466C>A | p.Ser489X | S489X |
| c.1475C>T | p.Ser492Phe | S492F |
| c.1477C>T | p.Gln493X | Q493X |
| c.1519_1521delATC | p.Ile507del | I507del |
| c.1521_1523delCTT | p.Phe508del | F508del |
| c.1545_1546delTA | p.Tyr515X | 1677delTA |
| c.1558G>T | p.Val520Phe | V520F |
| c.1573C>T | p.Gln525X | Q525X |
| c.1585-8G>A | No protein name | 1717-8G->A |
| c.1585-1G>A | No protein name | 1717-1G->A |
| c.1624G>T | p.Gly542X | G542X |
| c.1645A>C or c.1647T>G | p.Ser549Arg | S549R |
| c.1646G>A | p.Ser549Asn | S549N |
| c.1650delA | p.Gly551ValfsX8 | 1782delA |
| c.1651G>A | p.Gly551Ser | G551S |

FIG. 6 (continued)

| Mutation cDNA Name | Mutation Protein Name | Mutation Legacy Name |
|---|---|---|
| c.1652G>A | p.Gly551Asp | G551D |
| c.1654C>T | p.Gln552X | Q552X |
| c.1657C>T | p.Arg553X | R553X |
| c.1673T>C | p.Leu558Ser | L558S |
| c.1675G>A | p.Ala559Thr | A559T |
| c.1679G>A | p.Arg560Lys | R560K |
| c.1679G>C | p.Arg560Thr | R560T |
| c.1679+1G>C | No protein name | 1811+1G->C |
| c.1679+1.6kbA>G | No protein name | 1811+1.6kbA->G |
| c.1680-1G>A | No protein name | 1812-1G->A |
| c.1682C>A | p.Ala561Glu | A561E |
| c.1692delA | p.Asp565MetfsX7 | 1824delA |
| c.1705T>G | p.Tyr569Asp | Y569D |
| c.1727G>C | p.Gly576Ala | G576A |
| c.1736A>G | p.Asp579Gly | D579G |
| c.1753G>T | p.Glu585X | E585X |
| c.1766+1G>A | No protein name | 1898+1G->A |
| c.1766+1G>C | No protein name | 1898+1G->C |
| c.1766+3A>G | No protein name | 1898+3A->G |
| c.1841A>G | p.Asp614Gly | D614G |
| c.1923_1931del9ins | pSer641ArgfsX5 | 2055del9->A |
| c.1973_1985del13insAGAAA | p.Arg658 LysfsX4 | 2105-2117del13insAGAAA |
| c.1986_1989delAACT | p.Thr663ArgfsX8 | 2118del4 |
| c.2002C>T | p.Arg668Cys | R668C |
| c.2012delT | p.Leu671X | 2143delT |
| c.2051_2052delAAinsG | p.Lys684SerfsX38 | 2183AA->G+ |
| c.2051_2052delAAinsG | p.Lys684SerfsX38 | 2183delAA->G# |

FIG. 6 (continued)

| Mutation cDNA Name | Mutation Protein Name | Mutation Legacy Name |
|---|---|---|
| c.2052_2053insA | p.Gln685Thrfsx4 | 2184insA |
| c.2052delA | p.Lys684AsnfsX38 | 2184delA |
| c.2125C>T | p.Arg709X | R709X |
| c.2128A>T | p.Lys710X | K710X |
| c.2175_2176insA | p.Glu726ArgfsX4 | 2307insA |
| c.2195T>G | p.Leu732X | L732X |
| c.2215delG | p.Val739TyrfsX16 | 2347delG |
| c.2260G>A | p.Val754Met | V754M |
| c.2290C>T | p.Arg764X | R764X |
| c.2353C>T | p.Arg785X | R785X |
| c.2374C>T | p.Arg792X | R792X |
| c.2424_2425insAT | p.Ser809IlefsX13 | 2556insAT |
| c.2453delT | p.Leu818TrpfsX3 | 2585delT |
| c.2462_2463delGT | p.Ser821ArgfsX4 | No legacy name |
| c.2464G>T | p.Glu822X | E822X |
| c.2490+1G>A | No protein name | 2622+1G->A |
| c.2491G>T | p.Glu831X | E831X |
| c.2537G>A or c.2538G>A | p.Trp846X | W846X |
| c.2547C>A | p.Tyr849X | Y849X |
| c.2551C>T | p.Arg851X | R851X |
| c.2583delT | p.Phe861LeufsX3 | 2711delT |
| c.2657+2_2657+3insA | No protein name | 2789+2insA |
| c.2657+5G>A | No protein name | 2789+5G->A |
| c.2658-1G>C | No protein name | 2790-1G->C |
| c.2668C>T | p.Gln890X | Q890X |
| c.2735C>A | p.Ser912X | S912X |
| c.2737_2738insG |  | 2869insG |
| c.2739T>A | p.Tyr913X | Y913X |
| c.2764_2765insAG | p.Val922GlufsX2 | 2896insAG |
| c.2780T>C | p.Leu927Pro | L927P |
| c.2834C>T | p.Ser945Leu | S945L |

FIG. 6 (continued)

| Mutation cDNA Name | Mutation Protein Name | Mutation Legacy Name |
|---|---|---|
| c.2875delG | p.Ala959HisfsX9 | 3007delG |
| c.2908G>C | p.Gly970Arg | G970R |
| c.2930C>T | p.Ser977Phe | S977F |
| c.2988G>A | No protein name | 3120G->A |
| c.2988+1G>A | No protein name | 3120+1G->A |
| c.2989-977_3367+248del | No protein name | 3121-977_3499+248del2515 |
| c.2989-1G>A | No protein name | 3121-1G->A |
| c.2991G>C | p.Leu997Phe | L997F |
| c.3002_3003delTG | p.Val1001AspfsX45 | 3132delTG |
| c.3080T>C | p.Ile1027Thr | I1027T |
| c.3140-26A>G | No protein name | 3272-26A->G |
| c.3154T>G | p.Phe1052Val | F1052V |
| c.3160C>G | p.His1054Asp | H1054D |
| c.3181G>C | p.Gly1061Arg | G1061R |
| c.3194T>C | p.Leu1065Pro | L1065P |
| c.3196C>T | p.Arg1066Cys | R1066C |
| c.3197G>A | p.Arg1066His | R1066H |
| c.3205G>A | p.Gly1069Arg | G1069R |
| c.3208C>T | p.Arg1070Trp | R1070W |
| c.3209G>A | p.Arg1070Gln | R1070Q |
| c.3222T>A | p.Phe1074Leu | F1074L |
| c.3230T>C | p.Leu1077Pro | L1077P |
| c.3266G>A | p.Trp1089X | W1089X |
| c.3276C>A or c.3276C>G | p.Tyr1092X | Y1092X |
| c.3302T>A | p.Met1101Lys | M1101K |
| c.3310G>T | p.Glu1104X | E1104X |
| c.3454G>C | p.Asp1152His | D1152H |
| c.3472C>T | p.Arg1158X | R1158X |
| c.3484C>T | p.Arg1162X | R1162X |

FIG. 6 (continued)

| Mutation cDNA Name | Mutation Protein Name | Mutation Legacy Name |
|---|---|---|
| c.3485G>T | p.Arg1162Leu | R1162L |
| c.3528delC | p.Lys1177SerfsX15 | 3659delC |
| c.3535_3536insTCAA | p.Thr1179IlefsX17 | 3667ins4 |
| c.3587C>G | p.Ser1196X | S1196X |
| c.3605delA | p.Asp1202AlafsX9 | 3737delA |
| c.3611G>A or c.3612G>A | p.Trp1204X | W1204X |
| c.3659delC | p.Thr1220LysfsX8 | 3791delC |
| c.3691delT | p.Ser1231ProfsX4 | 3821delT |
| c.3700A>G | p.Ile1234Val | I1234V |
| c.3705T>G | p.Ser1235Arg | S1235R |
| c.3717+12191C>T | No protein name | 3849+10kbC->T |
| c.3718-1G>A | No protein name | 3850-1G->A |
| c.3731G>A | p.Gly1244Glu | G1244E |
| c.3744delA | p.Lys1250ArgfsX9 | 3876delA |
| c.3752G>A | p.Ser1251Asn | S1251N |
| c.3763T>C | p.Ser1255Pro | S1255P |
| c.3764C>A | p.Ser1255X | S1255X |
| c.3773_3774insT | p.Leu1258PhefsX7 | 3905insT |
| c.3808G>A | p.Asp1270Asn | D1270N |
| c.3846G>A | p.Trp1282X | W1282X |
| c.3873+1G>A | No protein name | 4005+1G->A |
| c.3883delA | p.Ile1295PhefsX33 | 4015delA |
| c.3884_3885insT | p.Ser1297PhefsX5 | 4016insT |
| c.3909C>G | p.Asn1303Lys | N1303K |
| c.3937C>T | p.Gln1313X | Q1313X |
| c.3964-78_4242+577del | NULL | CFTRdele22,23 |

FIG. 6 (continued)

| Mutation cDNA Name | Mutation Protein Name | Mutation Legacy Name |
|---|---|---|
| c.4046G>A | p.Gly1349Asp | G1349D |
| c.4077_4080delTGTTinsAA | No protein name | 4209TGTT->AA |
| c.4111G>T | p.Glu1371X | E1371X |
| c.4196_4197delTC | p.Cys1400X | 4326delTC |
| c.4234C>T | p.Gln1412X | Q1412X |
| c.4242+1G>T | No protein name | 4374+1G->T |
| c.4251delA | p.Glu1418ArgfsX14 | 4382delA |
| c.4296_4297insGA | p.Ser1435GlyfsX14 | 4428insGA |

METHODS OF TREATMENT FOR CYSTIC FIBROSIS

The instant application claims priority to U.S. Provisional Application No. 62/533,392, filed Jul. 17, 2017; U.S. Provisional Application No. 62/562,029, filed Sep. 22, 2017; U.S. Provisional Application No. 62/623,748, filed Jan. 30, 2018; U.S. Provisional Application No. 62/633,024, filed Feb. 20, 2018; and U.S. Provisional Application No. 62/657,508, filed Apr. 13, 2018, the entire contents of each of which are expressly incorporated herein by reference in their respective entireties.

Disclosed herein is a modulator of Cystic Fibrosis Transmembrane Conductance Regulator (CFTR), pharmaceutical compositions containing the modulator, methods of treatment of cystic fibrosis, and a process for making the modulator.

Cystic fibrosis (CF) is a recessive genetic disease that affects approximately 70,000 children and adults worldwide. Despite progress in the treatment of CF, there is no cure.

In patients with CF, mutations in CFTR endogenously expressed in respiratory epithelia lead to reduced apical anion secretion causing an imbalance in ion and fluid transport. The resulting decrease in anion transport contributes to enhanced mucus accumulation in the lung and accompanying microbial infections that ultimately cause death in CF patients. In addition to respiratory disease, CF patients typically suffer from gastrointestinal problems and pancreatic insufficiency that, if left untreated, result in death. In addition, the majority of males with cystic fibrosis are infertile, and fertility is reduced among females with cystic fibrosis.

Sequence analysis of the CFTR gene has revealed a variety of disease causing mutations (Cutting, G. R. et al. (1990) Nature 346:366-369; Dean, M. et al. (1990) Cell 61:863:870; and Kerem, B-S. et al. (1989) Science 245: 1073-1080; Kerem, B-S et al. (1990) Proc. Natl. Acad. Sci. USA 87:8447-8451). To date, greater than 2000 mutations in the CF gene have been identified; currently, the CFTR2 database contains information on only 322 of these identified mutations, with sufficient evidence to define 281 mutations as disease causing. The most prevalent disease-causing mutation is a deletion of phenylalanine at position 508 of the CFTR amino acid sequence, and is commonly referred to as the F508del mutation. This mutation occurs in approximately 70% of the cases of cystic fibrosis and is associated with severe disease.

The deletion of residue 508 in CFTR prevents the nascent protein from folding correctly. This results in the inability of the mutant protein to exit the endoplasmic reticulum (ER) and traffic to the plasma membrane. As a result, the number of CFTR channels for anion transport present in the membrane is far less than observed in cells expressing wild-type CFTR, i.e., CFTR having no mutations. In addition to impaired trafficking, the mutation results in defective channel gating. Together, the reduced number of channels in the membrane and the defective gating lead to reduced anion and fluid transport across epithelia. (Quinton, P. M. (1990), FASEB J. 4: 2709-2727). The channels that are defective because of the F508del mutation are still functional, albeit less functional than wild-type CFTR channels. (Dalemans et al. (1991), Nature Lond. 354: 526-528; Pasyk and Foskett (1995), J. Cell. Biochem. 270: 12347-50). In addition to F508del, other disease causing mutations in CFTR that result in defective trafficking, synthesis, and/or channel gating could be up- or down-regulated to alter anion secretion and modify disease progression and/or severity.

CFTR is a cAMP/ATP-mediated anion channel that is expressed in a variety of cell types, including absorptive and secretory epithelia cells, where it regulates anion flux across the membrane, as well as the activity of other ion channels and proteins. In epithelial cells, normal functioning of CFTR is critical for the maintenance of electrolyte transport throughout the body, including respiratory and digestive tissue. CFTR is composed of approximately 1480 amino acids that encode a protein which is made up of a tandem repeat of transmembrane domains, each containing six transmembrane helices and a nucleotide binding domain. The two transmembrane domains are linked by a large, polar, regulatory (R)-domain with multiple phosphorylation sites that regulate channel activity and cellular trafficking.

Chloride transport takes place by the coordinated activity of ENaC and CFTR present on the apical membrane and the $Na^+$-$K^+$-ATPase pump and Cl-channels expressed on the basolateral surface of the cell. Secondary active transport of chloride from the luminal side leads to the accumulation of intracellular chloride, which can then passively leave the cell via $Cl^-$ channels, resulting in a vectorial transport. Arrangement of $Na^+/2Cl^-/K^+$ co-transporter, $Na^+$-$K^+$-ATPase pump and the basolateral membrane $K^+$ channels on the basolateral surface and CFTR on the luminal side coordinate the secretion of chloride via CFTR on the luminal side. Because water is probably never actively transported itself, its flow across epithelia depends on tiny transepithelial osmotic gradients generated by the bulk flow of sodium and chloride.

Accordingly, there is a need for novel treatments of CFTR mediated diseases.

Disclosed herein is Compound I and pharmaceutically acceptable salts thereof. Compound I can be depicted as having the following structure:

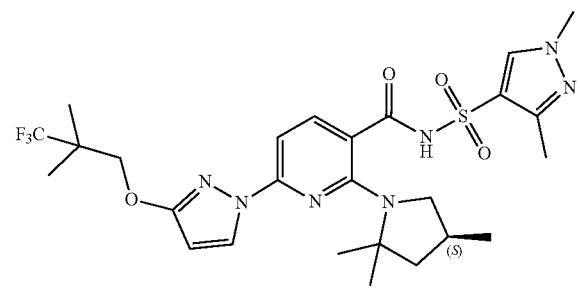

A chemical name for Compound I is N-(1,3-dimethylpyrazol-4-yl)sulfonyl-6-[3-(3,3,3-trifluoro-2,2-dimethylpropoxy)pyrazol-1-yl]-2-[(4S)-2,2,4-trimethylpyrrolidin-1-yl]pyridine-3-carboxamide.

Also disclosed herein are pharmaceutical compositions comprising Compound I and/or at least one pharmaceutically acceptable salt thereof, which compositions may further include at least one additional active pharmaceutical ingredient and/or at least one carrier. Also disclosed are methods of treating the CFTR-mediated disease cystic fibrosis comprising administering Compound I and/or at least one pharmaceutically acceptable salt thereof, optionally as part of a pharmaceutical composition comprising at least one additional component, to a subject in need thereof. A process of making Compound I and/or pharmaceutically acceptable salts thereof is also disclosed.

BRIEF DESCRIPTION OF THE DRAWINGS

FIG. 6 is a representative list of CFTR genetic mutations.

DEFINITIONS

Figure 1:
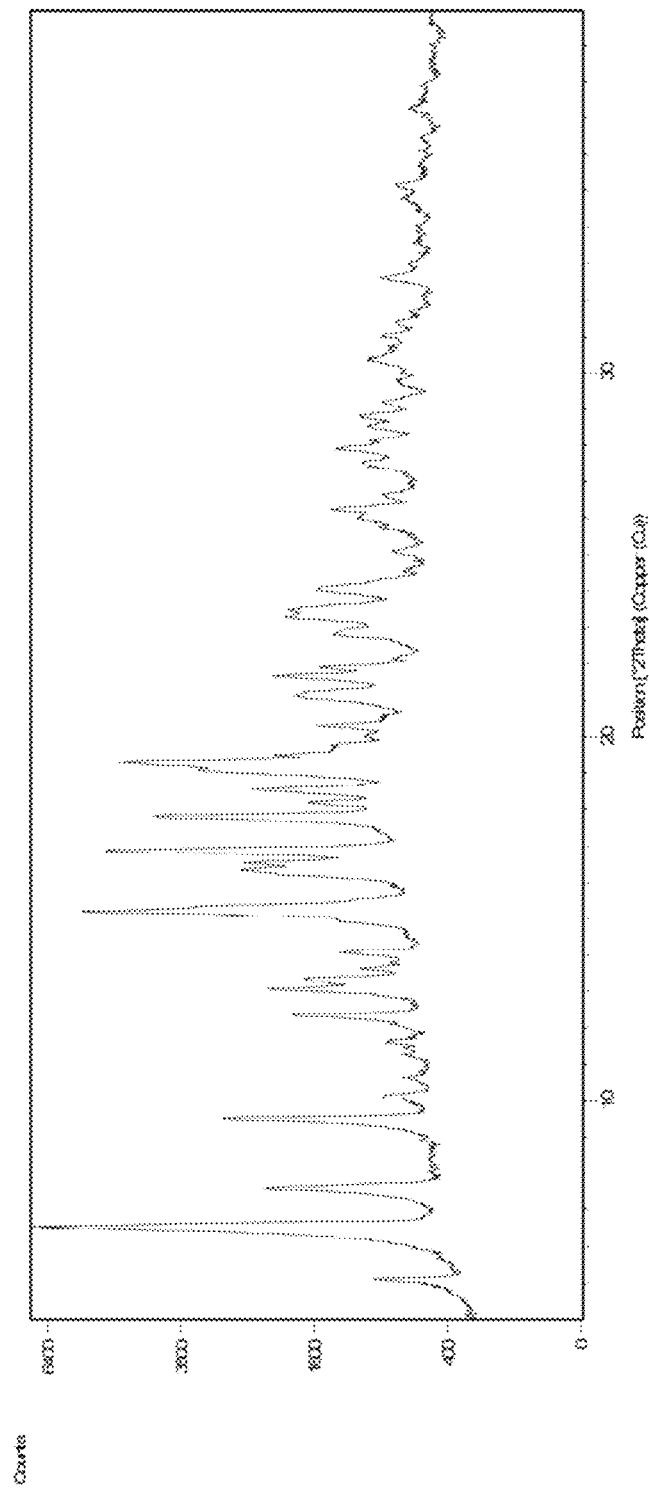
FIG. 1 is an XRPD of Form A of Compound I.

As used herein, "CFTR" means cystic fibrosis transmembrane conductance regulator.

As used herein, "mutations" can refer to mutations in the CFTR gene or the CFTR protein. A "CFTR gene mutation" refers to a mutation in the CFTR gene, and a "CFTR protein mutation" refers to a mutation in the CFTR protein. A genetic defect or mutation, or a change in the nucleotides in a gene in general results in a mutation in the CFTR protein translated from that gene, or a frame shift(s).

The term "F508del" refers to a mutant CFTR protein which is lacking the amino acid phenylalanine at position 508.

As used herein, a patient who is "homozygous" for a particular gene mutation has the same mutation on each allele.

As used herein, a patient who is "heterozygous" for a particular gene mutation has this mutation on one allele, and a different mutation on the other allele.

As used herein, the term "modulator" refers to a compound that increases the activity of a biological compound such as a protein. For example, a CFTR modulator is a compound that increases the activity of CFTR. The increase in activity resulting from a CFTR modulator includes but is not limited to compounds that correct, potentiate, stabilize and/or amplify CFTR.

As used herein, the term "CFTR corrector" refers to a compound that facilitates the processing and trafficking of CFTR to increase the amount of CFTR at the cell surface. Compounds I and II disclosed herein are CFTR correctors.

As used herein, the term "CFTR potentiator" refers to a compound that increases the channel activity of CFTR protein located at the cell surface, resulting in enhanced ion transport. Compound III and III-d disclosed herein are CFTR potentiators.

As used herein, the term "active pharmaceutical ingredient" or "therapeutic agent" ("API") refers to a biologically active compound.

As used herein, the term "pharmaceutically acceptable salt" refers to a salt form of a compound of this disclosure wherein the salt is nontoxic. Pharmaceutically acceptable salts of the compounds of this disclosure include those derived from suitable inorganic and organic acids and bases. Pharmaceutically acceptable salts are well known in the art. For example, S. M. Berge, et al. describes pharmaceutically acceptable salts in detail in *J. Pharmaceutical Sciences*, 1977, 66, 1-19.

As used herein, the term "amorphous" refers to a solid material having no long range order in the position of its molecules. Amorphous solids are generally supercooled liquids in which the molecules are arranged in a random manner so that there is no well-defined arrangement, e.g., molecular packing, and no long range order. Amorphous solids are generally isotropic, i.e. exhibit similar properties in all directions and do not have definite melting points. For example, an amorphous material is a solid material having no sharp characteristic crystalline peak(s) in its X-ray power diffraction (XRPD) pattern (i.e., is not crystalline as determined by XRPD). Instead, one or several broad peaks (e.g., halos) appear in its XRPD pattern. Broad peaks are characteristic of an amorphous solid. See, US 2004/0006237 for a comparison of XRPDs of an amorphous material and crystalline material. In some embodiments, a solid material may comprise an amorphous compound, and the material may, for example, be characterized by a lack of sharp characteristic crystalline peak(s) in its XRPD spectrum (i.e. the material is not crystalline, but is amorphous, as determined by XRPD). Instead, one or several broad peaks (e.g. halos) may appear in the XRPD pattern of the material. See US 2004/0006237 for a comparison of XRPDs of an amorphous material and crystalline material. A solid material, comprising an amorphous compound, may be characterized by, for example, a wider temperature range for the melting of the solid material, as compared to the range for the melting of a pure crystalline solid. Other techniques, such as, for example, Raman spectroscopy, infrared spectroscopy, and solid state NMR may be used to characterize crystalline or amorphous forms.

In some embodiments, a solid material may comprise a mixture of crystalline solids and amorphous solids. A solid material prepared to comprise an amorphous compound may also, for example, contain up to 30% of a crystalline solid. In some embodiments, a solid material prepared to comprise an amorphous compound may also, for example, contain up to 25%, 20%, 15%, 10%, 5%, or 2% of a crystalline solid. In embodiments wherein the solid material contains a mixture of crystalline solids and amorphous solids, the characterizing data, such as XRPD, may contain indicators of both crystalline and amorphous solids. As used herein, the term "substantially amorphous" refers to a solid material having little or no long range order in the position of its molecules. For example, substantially amorphous materials have less than 15% crystallinity (e.g., less than 10% crystallinity or less than 5% crystallinity). It is also noted that the term 'amorphous' includes the descriptor, 'amorphous', which refers to materials having no (0%) crystallinity.

As used herein, the term "dispersion" refers to a disperse system in which one substance, the dispersed phase, is distributed, in discrete units, throughout a second substance (the continuous phase or vehicle). The size of the dispersed phase can vary considerably (e.g. colloidal particles of nanometer dimension, to multiple microns in size). In general, the dispersed phases can be solids, liquids, or gases. In the case of a solid dispersion, the dispersed and continuous phases are both solids. In pharmaceutical applications, a solid dispersion can include a crystalline drug (dispersed phase) in an amorphous polymer (continuous phase); or alternatively, an amorphous drug (dispersed phase) in an amorphous polymer (continuous phase). In some embodiments, a solid dispersion includes the polymer constituting the dispersed phase and the drug constitute the continuous phase. Or, a solid dispersion includes the drug constituting the dispersed phase, and the polymer constituting the continuous phase.

The terms "patient" and "subject" are used interchangeably and refer to an animal including humans.

The terms "effective dose" and "effective amount" are used interchangeably herein and refer to that amount of a compound that produces the desired effect for which it is administered (e.g., improvement in CF or a symptom of CF, or lessening the severity of CF or a symptom of CF). The exact amount of an effective dose will depend on the purpose of the treatment, and will be ascertainable by one skilled in the art using known techniques (see, e.g., Lloyd (1999) The Art, Science and Technology of Pharmaceutical Compounding).

One of ordinary skill in the art would recognize that, when an amount of "a compound or a pharmaceutically acceptable salt thereof" is disclosed, the amount of the pharmaceutically acceptable salt form of the compound is the amount equivalent to the concentration of the free base of the compound. It is noted that the disclosed amounts of the compounds or their pharmaceutically acceptable salts thereof herein are based upon their free base form. For example, "100 mg of Compound I or its pharmaceutically acceptable salt" includes 100 mg of Compound I and a concentration of a pharmaceutically acceptable salt of Compound I equivalent to 100 mg of Compound I.

As used herein, the terms "treatment," "treating," and the like generally mean the improvement of CF or its symptoms or lessening the severity of CF or its symptoms in a subject. "Treatment," as used herein, includes, but is not limited to, the following: increased growth of the subject, increased weight gain, reduction of mucus in the lungs, improved pancreatic and/or liver function, reduction of chest infections, and/or reductions in coughing or shortness of breath. Improvements in or lessening the severity of any of these symptoms can be readily assessed according to standard methods and techniques known in the art.

As used herein, the term "in combination with," when referring to two or more compounds, agents, or additional active pharmaceutical ingredients, means the administration of two or more compounds, agents, or active pharmaceutical ingredients to the patient prior to, concurrent with, or subsequent to each other.

The term "approximately", when used in connection with doses, amounts, or weight percent of ingredients of a composition or a dosage form, include the value of a specified dose, amount, or weight percent or a range of the dose, amount, or weight percent that is recognized by one of ordinary skill in the art to provide a pharmacological effect equivalent to that obtained from the specified dose, amount, or weight percent.

As stated above, disclosed herein is Compound I, which can be depicted as having the following structure:

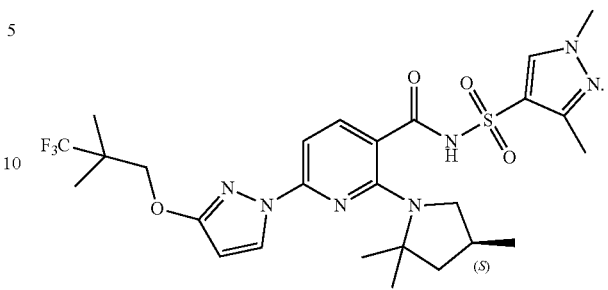

A chemical name for Compound I is N-(1,3-dimethylpyrazol-4-yl)sulfonyl-6-[3-(3,3,3-trifluoro-2,2-dimethylpropoxy)pyrazol-1-yl]-2-[(4S)-2,2,4-trimethylpyrrolidin-1-yl]pyridine-3-carboxamide. Compound I may be in the form of a pharmaceutically acceptable salt thereof.

In some embodiments, Compound I (and/or at least one pharmaceutically acceptable salt thereof) can be administered in combination with at least one additional active pharmaceutical ingredient. In some embodiments, the at least one additional active pharmaceutical ingredient is chosen from:

(a) Compound II:

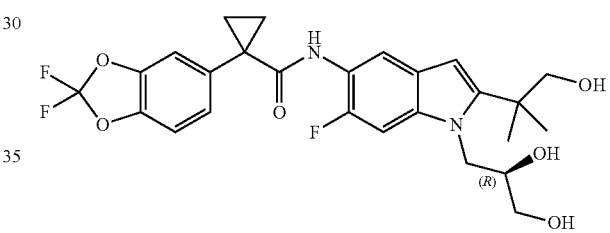

and pharmaceutically acceptable salts thereof.

A chemical name for Compound II is (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide;

(b) Compound III or Compound III-d:

(Compound III)

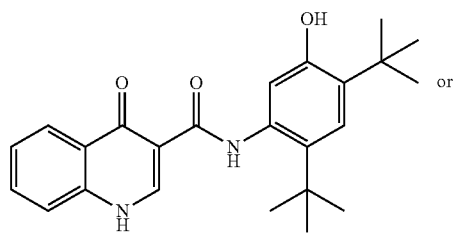

or (Compound III-d)

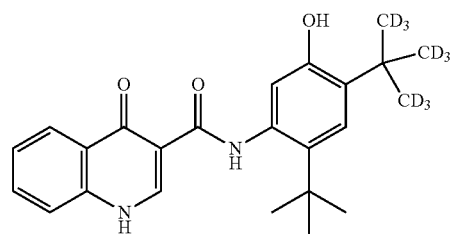

and pharmaceutically acceptable salts thereof.

A chemical name for Compound III is N-(5-hydroxy-2,4-di-tert-butyl-phenyl)-4-oxo-1H-quinoline-3-carboxamide, and a chemical name for Compound III-d is N-(2-(tert-butyl)-5-hydroxy-4-(2-(methyl-d3)propan-2-yl-1,1,1,3,3,3-d6)phenyl)-4-oxo-1,4-dihydroquinoline-3-carboxamide; and (c) Compound IV:

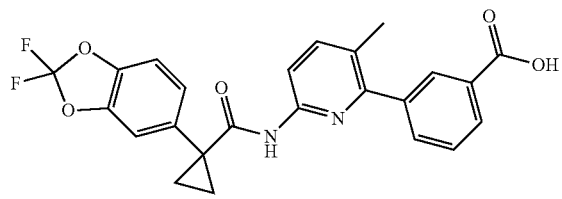 [SMILES: Cc1ccc(NC(=O)C2(c3ccc4c(c3)OC(F)(F)O4)CC2)nc1-c1cccc(C(=O)O)c1]

and pharmaceutically acceptable salts thereof.

A chemical name for Compound IV is 3-(6-(1-(2,2-difluorobenzo[d][1,3]dioxol-5-yl)cyclopropanecarboxamido)-3-methylpyridin-2-yl)benzoic acid.

Suitable pharmaceutically acceptable salts are, for example, those disclosed in S. M. Berge, et al. *J. Pharmaceutical Sciences*, 1977, 66, 1-19. For example, Table 1 of that article provides the following pharmaceutically acceptable salts:

TABLE 1

| | | |
|---|---|---|
| Acetate | Iodide | Benzathine |
| Benzenesulfonate | Isethionate | Chloroprocaine |
| Benzoate | Lactate | Choline |
| Bicarbonate | Lactobionate | Diethanolamine |
| Bitartrate | Malate | Ethylenediamine |
| Bromide | Maleate | Meglumine |
| Calcium edetate | Mandelate | Procaine |
| Camsylate | Mesylate | Aluminum |
| Carbonate | Methylbromide | Calcium |
| Chloride | Methylnitrate | Lithium |
| Citrate | Methylsulfate | Magnesium |
| Dihydrochloride | Mucate | Potassium |
| Edetate | Napsylate | Sodium |
| Edisylate | Nitrate | Zinc |
| Estolate | Pamoate (Embonate) | |
| Esylate | Pantothenate | |
| Fumarate | Phosphate/diphosphate | |
| Gluceptate | Polygalacturonate | |
| Gluconate | Salicylate | |
| Glutamate | Stearate | |
| Glycollylarsanilate | Subacetate | |
| Hexylresorcinate | Succinate | |
| Hydrabamine | Sulfate | |
| Hydrobromide | Tannate | |
| Hydrochloride | Tartrate | |
| Hydroxynaphthoate | Teociate | |
| | Triethiodide | |

Non-limiting examples of pharmaceutically acceptable acid addition salts include: salts formed with inorganic acids, such as hydrochloric acid, hydrobromic acid, phosphoric acid, sulfuric acid, or perchloric acid; salts formed with organic acids, such as acetic acid, oxalic acid, maleic acid, tartaric acid, citric acid, succinic acid or malonic acid; and salts formed by using other methods used in the art, such as ion exchange. Non-limiting examples of pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate salts. Pharmaceutically acceptable salts derived from appropriate bases include alkali metal, alkaline earth metal, ammonium, and $N^{+}(C_{1-4}alkyl)_4$ salts. This disclosure also envisions the quaternization of any basic nitrogen-containing groups of the compounds disclosed herein. Suitable non-limiting examples of alkali and alkaline earth metal salts include sodium, lithium, potassium, calcium, and magnesium. Further non-limiting examples of pharmaceutically acceptable salts include ammonium, quaternary ammonium, and amine cations formed using counterions such as halide, hydroxide, carboxylate, sulfate, phosphate, nitrate, lower alkyl sulfonate and aryl sulfonate. Other suitable, non-limiting examples of pharmaceutically acceptable salts include besylate and glucosamine salts.

In some embodiments, at least one compound chosen from Compound I and pharmaceutically acceptable salts thereof is administered in combination with at least one compound chosen from Compound II and pharmaceutically acceptable salts thereof. In some embodiments, at least one compound chosen from Compound I and pharmaceutically acceptable salts thereof is administered in combination with at least one compound chosen from Compound III and pharmaceutically acceptable salts thereof. In some embodiments, at least one compound chosen from Compound I and pharmaceutically acceptable salts thereof is administered in combination with at least one compound chosen from Compound IV and pharmaceutically acceptable salts thereof. In some embodiments, at least one compound chosen from Compound I and pharmaceutically acceptable salts thereof is administered in combination with Compounds II or a pharmaceutically acceptable salt thereof and at least one compound chosen from Compound III and pharmaceutically acceptable salts thereof. In some embodiments, at least one compound chosen from Compound I and pharmaceutically acceptable salts thereof is administered in combination with at least one compound chosen from Compound III and pharmaceutically acceptable salts thereof and at least one compound chosen from Compound IV and pharmaceutically acceptable salts thereof. In some embodiments, at least one compound chosen from Compound I and pharmaceutically acceptable salts thereof is administered in combination with at least one compound chosen from Compound III-d and pharmaceutically acceptable salts thereof. In some embodiments, at least one compound chosen from Compound I and pharmaceutically acceptable salts thereof is administered in combination with at least one compound chosen from Compound IV and pharmaceutically acceptable salts thereof. In some embodiments, at least one compound chosen from Compound I and pharmaceutically acceptable salts thereof is administered in combination with Compounds II or a pharmaceutically acceptable salt thereof and at least one compound chosen from Compound III-d and pharmaceutically acceptable salts thereof. In some embodiments, at least one compound chosen from Compound I and pharmaceutically acceptable salts thereof is administered in combination with at least one compound chosen from Compound III-d and pharmaceutically acceptable salts thereof and at least one compound chosen from Compound IV and pharmaceutically acceptable salts thereof.

Each of Compounds I, II, III, III-d, and IV and their pharmaceutically acceptable salts thereof independently can be administered once daily, twice daily, or three times daily. The term "daily" means per day. For example, 100 mg of Compound I is administered daily means total of 100 mg of Compound I per day is administered, which can be administered, for example, once daily, twice daily, or three times daily. For example, 100 mg of Compound I is administered once daily (qd) means 100 mg of Compound I per dosing is administered once per day. For example, 50 mg of Compound I is administered twice daily (bid) means 50 mg of Compound I per dosing is administered twice per day. In some embodiments, at least one compound chosen from Compound I and pharmaceutically acceptable salts thereof is administered once daily. In some embodiments, at least one compound chosen from Compound I and pharmaceutically acceptable salts thereof is administered twice daily. In some embodiments, Compound II or its pharmaceutically acceptable salts thereof are administered once daily. In some embodiments, Compound II or its pharmaceutically acceptable salts thereof are administered twice daily. In some embodiments, Compound III or its pharmaceutically acceptable salts thereof are administered once daily. In some embodiments, Compound III or its pharmaceutically acceptable salts thereof are administered twice daily. In some embodiments, Compound III-d or its pharmaceutically acceptable salts thereof are administered once daily. In some embodiments, Compound III-d or its pharmaceutically acceptable salts thereof are administered twice daily. In some embodiments, Compound IV or its pharmaceutically acceptable salts thereof are administered once daily. In some embodiments, Compound IV or its pharmaceutically acceptable salts thereof are administered twice daily.

In some embodiments, at least one compound chosen from Compound I and pharmaceutically acceptable salts thereof is administered in an amount 10 mg to 900 mg, 20 mg to 800 mg, 80 mg to 800 mg, 30 mg to 720 mg, 40 mg to 600 mg, 60 mg to 100 mg, 60 mg to 500 mg, 80 mg to 400 mg, 120 mg to 240 mg, 120 mg to 360 mg, 160 mg to 320 mg, 240 mg to 400 mg, 320 mg to 480 mg, 360 mg to 640 mg, daily. In some embodiments, at least one compound chosen from Compound I and pharmaceutically acceptable salts thereof is administered in an amount 40 mg to 600 mg, 40 mg to 500 mg, 40 mg to 400 mg, 40 mg to 300 mg, 50 mg to 360 mg, or 80 mg to 360 mg, daily. In some embodiments, at least one compound chosen from Compound I and pharmaceutically acceptable salts thereof is administered in an amount of 80 mg, 120 mg, 160 mg, 240 mg, 250 mg, 320 mg, 400 mg, 480 mg, 560 mg, 640 mg, or 720 mg once daily. In some embodiments, at least one compound chosen from Compound I and pharmaceutically acceptable salts thereof is administered in an amount of 80 mg, 120 mg, 160 mg, 250 mg, 320 mg, or 400 mg twice daily. In some embodiments, at least one compound chosen from Compound I and pharmaceutically acceptable salts thereof is administered in an amount of 20 mg daily, 60 mg daily, 120 mg daily, 200 mg daily, 240 mg daily, 250 mg daily, 300 mg daily, 350 mg daily, 400 mg daily, 450 mg daily, 480 mg daily, 500 mg daily, 550 mg daily, 600 mg daily, or 800 mg daily. In some embodiments, at least one compound chosen from Compound I and pharmaceutically acceptable salts thereof is administered in an amount of 20 mg daily, 60 mg daily, 120 mg daily, 200 mg daily, 240 mg daily, 250 mg daily, 300 mg daily, 350 mg daily, 400 mg daily, 450 mg daily, 480 mg daily, 500 mg daily, 550 mg daily, 600 mg daily, or 800 mg daily. In some embodiments, at least one compound chosen from Compound I and pharmaceutically acceptable salts thereof is administered in an amount of 50 mg, 60 mg, 100 mg, 120 mg, 150 mg, 200 mg, 240 mg, 250 mg, 300 mg, 350 mg, 400 mg, 450 mg, 500 mg, 550 mg, 600 mg, 650 mg, 700 mg, or 800 mg, once daily.

In some embodiments, the disclosure features a pharmaceutical composition comprising at least one compound chosen from Compound I and pharmaceutically acceptable salts thereof, and at least one pharmaceutically acceptable carrier.

In some embodiments, the disclosure features a pharmaceutical composition comprising at least one compound chosen from Compound I and pharmaceutically acceptable salts thereof, at least one compound chosen from Compound II and pharmaceutically acceptable salts thereof, and at least one pharmaceutically acceptable carrier.

In some embodiments, the disclosure features a pharmaceutical composition comprising at least one compound chosen from Compound I and pharmaceutically acceptable salts thereof, at least one compound chosen from Compound III and pharmaceutically acceptable salts thereof, and at least one pharmaceutically acceptable carrier.

In some embodiments, the disclosure features a pharmaceutical composition comprising at least one compound chosen from Compound I and pharmaceutically acceptable salts thereof, at least one compound chosen from Compound II and pharmaceutically acceptable salts thereof, at least one compound chosen from Compound III and pharmaceutically acceptable salts thereof, and at least one pharmaceutically acceptable carrier.

In some embodiments, the disclosure features a pharmaceutical composition comprising at least one compound chosen from Compound I and pharmaceutically acceptable salts thereof, at least one compound chosen from Compound III and pharmaceutically acceptable salts thereof, at least one compound chosen from Compound IV and pharmaceutically acceptable salts thereof, and at least one pharmaceutically acceptable carrier.

Compounds I, II, III, and/or IV and their pharmaceutically acceptable salts thereof can be comprised in a single pharmaceutical composition or separate pharmaceutical compositions. Such pharmaceutical compositions can be administered once daily or multiple times daily, such as twice daily.

In some embodiments, at least one compound chosen from Compound I and pharmaceutically acceptable salts thereof is comprised in a first pharmaceutical composition, at least one compound chosen from Compound II and pharmaceutically acceptable salts thereof is comprised in a second pharmaceutical composition, and at least one compound chosen from Compound III and pharmaceutically acceptable salts thereof is comprised in a third pharmaceutical composition.

In some embodiments, at least one compound chosen from Compound I and pharmaceutically acceptable salts thereof is comprised in a first pharmaceutical composition, and at least one compound chosen from Compound II and pharmaceutically acceptable salts thereof and at least one compound chosen from Compound III and pharmaceutically acceptable salts thereof are comprised in a second pharmaceutical composition. In some embodiments, the second pharmaceutical composition comprises a half of the daily dose of said at least one compound chosen from Compound III and pharmaceutically acceptable salts thereof, and the other half of the daily dose of said at least one compound chosen from Compound III and pharmaceutically acceptable salts thereof is administered in a third pharmaceutical composition.

In some embodiments, at least one compound chosen from Compound I and pharmaceutically acceptable salts thereof is comprised in a first pharmaceutical composition, at least one compound chosen from Compound II and pharmaceutically acceptable salts thereof is comprised in a second pharmaceutical composition, and at least one compound chosen from Compound III and pharmaceutically acceptable salts thereof is comprised in the first pharmaceutical composition. In some embodiments, the first pharmaceutical composition is administered to the patient twice daily.

In some embodiments, the disclosure features a pharmaceutical composition comprising at least one compound chosen from Compound I and pharmaceutically acceptable salts thereof, at least one compound chosen from Compound III-d and pharmaceutically acceptable salts thereof, and at least one pharmaceutically acceptable carrier.

In some embodiments, the disclosure features a pharmaceutical composition comprising at least one compound chosen from Compound I and pharmaceutically acceptable salts thereof, at least one compound chosen from Compound II and pharmaceutically acceptable salts thereof, at least one compound chosen from Compound III-d and pharmaceutically acceptable salts thereof, and at least one pharmaceutically acceptable carrier.

In some embodiments, the disclosure features a pharmaceutical composition comprising at least one compound chosen from Compound I and pharmaceutically acceptable salts thereof, at least one compound chosen from Compound III-d and pharmaceutically acceptable salts thereof, at least one compound chosen from Compound IV and pharmaceutically acceptable salts thereof, and at least one pharmaceutically acceptable carrier.

Compounds I, II, III-d, and/or IV and their pharmaceutically acceptable salts thereof can be comprised in a single pharmaceutical composition or separate pharmaceutical compositions. Such pharmaceutical compositions can be administered once daily or multiple times daily, such as twice daily.

In some embodiments, at least one compound chosen from Compound I and pharmaceutically acceptable salts thereof is comprised in a first pharmaceutical composition, at least one compound chosen from Compound II and pharmaceutically acceptable salts thereof is comprised in a second pharmaceutical composition, and at least one compound chosen from Compound III-d and pharmaceutically acceptable salts thereof is comprised in a third pharmaceutical composition.

In some embodiments, at least one compound chosen from Compound I and pharmaceutically acceptable salts thereof is comprised in a first pharmaceutical composition, and at least one compound chosen from Compound II and pharmaceutically acceptable salts thereof and at least one compound chosen from Compound III-d and pharmaceutically acceptable salts thereof are comprised in a second pharmaceutical composition. In some embodiments, the second pharmaceutical composition comprises a half of the daily dose of said at least one compound chosen from Compound III-d and pharmaceutically acceptable salts thereof, and the other half of the daily dose of said at least one compound chosen from Compound III-d and pharmaceutically acceptable salts thereof is administered in a third pharmaceutical composition.

In some embodiments, at least one compound chosen from Compound I and pharmaceutically acceptable salts thereof is comprised in a first pharmaceutical composition, at least one compound chosen from Compound II and pharmaceutically acceptable salts thereof is comprised in a second pharmaceutical composition, and at least one compound chosen from Compound III-d and pharmaceutically acceptable salts thereof is comprised in the first pharmaceutical composition. In some embodiments, the first pharmaceutical composition is administered to the patient twice daily.

In some embodiments, pharmaceutical compositions disclosed herein comprise at least one additional active pharmaceutical ingredient. In some embodiments, the at least one additional active pharmaceutical ingredient is a CFTR modulator. In some embodiments, the at least one additional active pharmaceutical ingredient is a CFTR corrector. In some embodiments, the at least one additional active pharmaceutical ingredient is a CFTR potentiator. In some embodiments, the pharmaceutical composition comprises Compound I and at least two additional active pharmaceutical ingredients, one of which is a CFTR corrector and one of which is a CFTR potentiator.

In some embodiments, at least one additional active pharmaceutical ingredient is selected from mucolytic agents, bronchodilators, antibiotics, anti-infective agents, and anti-inflammatory agents.

A pharmaceutical composition may further comprise at least one pharmaceutically acceptable carrier. In some embodiments, the at least one pharmaceutically acceptable carrier is chosen from pharmaceutically acceptable vehicles and pharmaceutically acceptable adjuvants. In some embodiments, the at least one pharmaceutically acceptable is chosen from pharmaceutically acceptable fillers, disintegrants, surfactants, binders, lubricants.

It will also be appreciated that a pharmaceutical composition of this disclosure, including a pharmaceutical composition comprising combinations described previously, can be employed in combination therapies; that is, the compositions can be administered concurrently with, prior to, or subsequent to, at least one additional active pharmaceutical ingredient or medical procedures.

Pharmaceutical compositions comprising these combinations are useful for treating cystic fibrosis.

In some embodiments, a pharmaceutical composition disclosed herein comprises at least one compound chosen from Compound I and pharmaceutically acceptable salts thereof, and at least one pharmaceutically acceptable carrier. In some embodiments, the pharmaceutically acceptable carrier is a polymer. In some embodiments, the pharmaceutically acceptable carrier is HPMCAS. In some embodiments, the pharmaceutically acceptable carrier is HPMCAS-HG. In some embodiments, the pharmaceutical composition comprises a solid dispersion of compound I in HPMCAS-HG. In some embodiments, the solid dispersion comprises compound I in HPMCAS-HG in a 1:1 weight ratio. In some embodiments, the solid dispersion comprises substantially amorphous compound I.

As described above, pharmaceutical compositions disclosed herein may optionally further comprise at least one pharmaceutically acceptable carrier. The at least one pharmaceutically acceptable carrier may be chosen from adjuvants and vehicles. The at least one pharmaceutically acceptable carrier, as used herein, includes any and all solvents, diluents, other liquid vehicles, dispersion aids, suspension aids, surface active agents, isotonic agents, thickening agents, emulsifying agents, preservatives, solid binders, and lubricants, as suited to the particular dosage form desired. Remington: *The Science and Practice of Pharmacy*, 21st edition, 2005, ed. D. B. Troy, Lippincott Williams & Wilkins, Philadelphia, and *Encyclopedia of Pharmaceutical*

Technology, eds. J. Swarbrick and J. C. Boylan, 1988-1999, Marcel Dekker, New York discloses various carriers used in formulating pharmaceutical compositions and known techniques for the preparation thereof. Except insofar as any conventional carrier is incompatible with the compounds of this disclosure, such as by producing any undesirable biological effect or otherwise interacting in a deleterious manner with any other component(s) of the pharmaceutical composition, its use is contemplated to be within the scope of this disclosure. Non-limiting examples of suitable pharmaceutically acceptable carriers include, but are not limited to, ion exchangers, alumina, aluminum stearate, lecithin, serum proteins (such as human serum albumin), buffer substances (such as phosphates, glycine, sorbic acid, and potassium sorbate), partial glyceride mixtures of saturated vegetable fatty acids, water, salts, and electrolytes (such as protamine sulfate, disodium hydrogen phosphate, potassium hydrogen phosphate, sodium chloride, and zinc salts), colloidal silica, magnesium trisilicate, polyvinyl pyrrolidone, polyacrylates, waxes, polyethylene-polyoxypropylene-block polymers, wool fat, sugars (such as lactose, glucose and sucrose), starches (such as corn starch and potato starch), cellulose and its derivatives (such as sodium carboxymethyl cellulose, ethyl cellulose and cellulose acetate), powdered tragacanth, malt, gelatin, talc, excipients (such as cocoa butter and suppository waxes), oils (such as peanut oil, cottonseed oil, safflower oil, sesame oil, olive oil, corn oil and soybean oil), glycols (such as propylene glycol and polyethylene glycol), esters (such as ethyl oleate and ethyl laurate), agar, buffering agents (such as magnesium hydroxide and aluminum hydroxide), alginic acid, pyrogen-free water, isotonic saline, Ringer's solution, ethyl alcohol, phosphate buffer solutions, non-toxic compatible lubricants (such as sodium lauryl sulfate and magnesium stearate), coloring agents, releasing agents, coating agents, sweetening agents, flavoring agents, perfuming agents, preservatives, and antioxidants.

It will also be appreciated that a pharmaceutical composition of this disclosure, including a pharmaceutical composition comprising any of the combinations described previously, can be employed in combination therapies; that is, the compositions can be administered concurrently with, prior to, or subsequent to, at least one active pharmaceutical ingredients or medical procedures.

In some embodiments, the methods of the disclosure employ administering to a patient in need thereof at least one compound chosen from Compound I and pharmaceutically acceptable salts thereof, and at least one selected from Compound II, Compound III, Compound III-d, Compound IV, and pharmaceutically acceptable salts thereof.

Any suitable pharmaceutical compositions known in the art can be used for Compound I, Compound II, Compound III, Compound III-d, Compound IV, and pharmaceutically acceptable salts thereof. Some exemplary pharmaceutical compositions for Compound I and its pharmaceutically acceptable salts are described in the Examples. Some exemplary pharmaceutical compositions for Compound II and its pharmaceutically acceptable salts can be found in WO 2011/119984 and WO 2014/015841, all of which are incorporated herein by reference. Some exemplary pharmaceutical compositions for Compound III and its pharmaceutically acceptable salts can be found in WO 2007/134279, WO 2010/019239, WO 2011/019413, WO 2012/027731, and WO 2013/130669, all of which are incorporated herein by reference. Some exemplary pharmaceutical compositions for Compound III-d and its pharmaceutically acceptable salts can be found in U.S. Pat. Nos. 8,865,902, 9,181,192, and 9,512,079, all of which are incorporated herein by reference. Some exemplary pharmaceutical compositions for Compound IV and its pharmaceutically acceptable salts can be found in WO 2010/037066, WO 2011/127241, WO 2013/112804, and WO 2014/071122, all of which are incorporated herein by reference.

In some embodiments, a pharmaceutical composition comprising at least one compound chosen from Compound I and pharmaceutically acceptable salts thereof is administered with a pharmaceutical composition comprising Compound II and Compound III. Pharmaceutical compositions comprising Compound II and Compound III are disclosed in PCT Publication No. WO 2015/160787, incorporated herein by reference. An exemplary embodiment is shown in the following Table:

TABLE 2

Exemplary Tablet Comprising 100 mg of Compound II and 150 mg of Compound III.

| | Ingredient | Amount per tablet (mg) |
|---|---|---|
| Intra-granular | Compound II SDD (spray dried dispersion) (80 wt % Compound IL 20 wt % HPMC) | 125 |
| | Compound III SDD (80 wt % Compound III, 19.5 wt % HPMCAS-HG; 0.5 wt % sodium lauryl sulfate) | 187.5 |
| | Microcrystalline cellulose | 131.4 |
| | Croscarmellose Sodium | 29.6 |
| | Total | 473.5 |
| Extra-granular | Microcrystalline cellulose | 112.5 |
| | Magnesium Stearate | 5.9 |
| | Total | 118.4 |
| Total uncoated Tablet | | 591.9 |
| Film coat | Opadry | 17.7 |
| Total coated Tablet | | 609.6 |

In some embodiments, a pharmaceutical composition comprising Compound I is administered with a pharmaceutical composition comprising Compound III Pharmaceutical compositions comprising Compound III are disclosed in PCT Publication No. WO 2010/019239, incorporated herein by reference. An exemplary embodiment is shown in the following Table:

TABLE 3

Ingredients for Exemplary Tablet of Compound III.

| Tablet Formulation | Percent Dose % Wt./Wt. | Dose (mg) | Batch (g) |
|---|---|---|---|
| Compound III SDD (80 wt % Compound III, 19.5 wt % HPMCAS-HG; 0.5 wt % sodium lauryl sulfate) | 34.09% | 187.5 | 23.86 |
| Microcrystalline cellulose | 30.51% | 167.8 | 21.36 |
| Lactose | 30.40% | 167.2 | 21.28 |
| Sodium croscarmellose | 3.000% | 16.50 | 2.100 |
| SLS | 0.500% | 2.750 | 0.3500 |
| Colloidal silicon dioxide | 0.500% | 2.750 | 0.3500 |
| Magnesium stearate | 1.000% | 5.500 | 0.7000 |
| Total | 100% | 550 | 70 |

Additional pharmaceutical compositions comprising Compound III are disclosed in PCT Publication No. WO 2013/130669, incorporated herein by reference. Exemplary mini-tablets (~2 mm diameter, ~2 mm thickness, each mini-tablet weighing approximately 6.9 mg) was formulated to have approximately 50 mg of Compound III per 26 mini-tablets and approximately 75 mg of Compound III per 39 mini-tablets using the amounts of ingredients recited in Table 4, below.

TABLE 4

Ingredients for mini-tablets for 50 mg and 75 mg potency

| Tablet Formulation | Percent Dose % Wt./Wt. | Dose (mg) 50 mg potency | Dose (mg) 75 mg potency | Batch (g) |
|---|---|---|---|---|
| Compound III SDD (80 wt % Compound III, 19.5 wt % HPMCAS-HG; 0.5 wt % sodium lauryl sulfate) | 35 | 62.5 | 93.8 | 1753.4 |
| Mannitol | 13.5 | 24.1 | 36.2 | 675.2 |
| Lactose | 41 | 73.2 | 109.8 | 2050.2 |
| Sucralose | 2.0 | 3.6 | 5.4 | 100.06 |
| Croscarmellose sodium | 6.0 | 10.7 | 16.1 | 300.1 |
| Colloidal silicon dioxide | 1.0 | 1.8 | 2.7 | 50.0 |
| Magnesium stearate | 1.5 | 2.7 | 4.0 | 74.19 |
| Total | 100 | 178.6 | 268 | 5003.15 |

In some embodiments, a pharmaceutical composition comprising Compound I is administered with a pharmaceutical composition comprising Compound III-d.

In some embodiments, the pharmaceutical compositions are a tablet. In some embodiments, the tablets are suitable for oral administration.

These combinations are useful for treating cystic fibrosis.

A CFTR mutation may affect the CFTR quantity, i.e., the number of CFTR channels at the cell surface, or it may impact CFTR function, i.e., the functional ability of each channel to open and transport ions. Mutations affecting CFTR quantity include mutations that cause defective synthesis (Class I defect), mutations that cause defective processing and trafficking (Class II defect), mutations that cause reduced synthesis of CFTR (Class V defect), and mutations that reduce the surface stability of CFTR (Class VI defect). Mutations that affect CFTR function include mutations that cause defective gating (Class III defect) and mutations that cause defective conductance (Class IV defect).

In some embodiments, disclosed herein methods of treating, lessening the severity of, or symptomatically treating cystic fibrosis in a patient comprising administering an effective amount of a compound, pharmaceutically acceptable salt thereof, or a deuterated analog of any of the foregoing; or a pharmaceutical composition, of this disclosure to a patient, such as a human, wherein said patient has cystic fibrosis. In some embodiments, the patient has F508del/minimal function (MF) genotypes, F508del/F508del genotypes, F508del/gating genotypes, or F508del/residual function (RF) genotypes.

As used herein, "minimal function (MF) mutations" refer to CFTR gene mutations associated with minimal CFTR function (little-to-no functioning CFTR protein) and include, for example, mutations associated with severe defects in ability of the CFTR channel to open and close, known as defective channel gating or "gating mutations"; mutations associated with severe defects in the cellular processing of CFTR and its delivery to the cell surface; mutations associated with no (or minimal) CFTR synthesis; and mutations associated with severe defects in channel conductance. Table C below includes a non-exclusive list of CFTR minimal function mutations, which are detectable by an FDA-cleared genotyping assay. In some embodiments, a mutation is considered a MF mutation if it meets at least 1 of the following 2 criteria:

(1) biological plausibility of no translated protein (genetic sequence predicts the complete absence of CFTR protein), or (2) in vitro testing that supports lack of responsiveness to Compound II, Compound III or the combination of Compound II and Compound III, and evidence of clinical severity on a population basis (as reported in large patient registries).

In some embodiments, the minimal function mutations are those that result in little-to-no functioning CFTR protein and are not responsive in vitro to Compound II, Compound III, or the combination of Compound II and Compound III.

In some embodiments, the minimal function mutations are those that are not responsive in vitro to Compound II, Compound III, or the combination of Compound II and Compound III. In some embodiments, the minimal function mutations are mutations based on in vitro testing met the following criteria in in vitro experiments:

baseline chloride transport that was <10% of wildtype CFTR, and an increase in chloride transport of <10% over baseline following the addition of TEZ, IVA, or TEZ/IVA in the assay.

In some embodiments, patients with at least one minimal function mutation exhibit evidence of clinical severity as defined as:

average sweat chloride>86 mmol/L, and prevalence of pancreatic insufficiency (PI)>50%.

Patients with an F508del/minimal function genotype are defined as patients that are heterozygous F508del-CFTR with a second CFTR allele containing a minimal function mutation. In some embodiments, patients with an F508del/minimal function genotype are patients that are heterozygous F508del-CFTR with a second CFTR allele containing a mutation that results in a CFTR protein with minimal CFTR function (little-to-no functioning CFTR protein) and that is not responsive in vitro to Compound II, Compound III, or the combination of Compound II and Compound III.

In some embodiments, minimal function mutations can be determined using 3 major sources:

biological plausibility for the mutation to respond (i.e., mutation class)

evidence of clinical severity on a population basis (per CFTR2 patient registry; accessed on 15 Feb. 2016)

average sweat chloride>86 mmol/L, and prevalence of pancreatic insufficiency (PI)>50% in vitro testing mutations resulting in baseline chloride transport<10% of wild-type CFTR were considered minimal function mutations resulting in chloride transport<10% of wild-type CFTR following the addition of Compound II and/or Compound III were considered nonresponsive.

As used herein, a "residual function mutations" refer to are Class II through V mutations that have some residual chloride transport and result in a less severe clinical phenotype. Residual function mutations are mutation in the CFTR gene that result in reduced protein quantity or function at the cell surface which can produce partial CFTR activity.

Non-limiting examples of CFTR gene mutations known to result in a residual function phenotype include a CFTR residual function mutation selected from 2789+5G→A, 3849+1 OkbC→T, 3272-26A→G, 711+3A→G, E56K, P67L, R74W, D110E, D1 10H, R117C, L206W, R347H, R352Q, A455E, D579G, E831X, S945L, S977F, F1052V, R1070W, F1074L, Dl 152H, D1270N, E193K, and K1060T. For example, CFTR mutations that cause defective mRNA splicing, such as 2789+507 A, result in reduced protein synthesis, but deliver some functional CFTR to the surface of the cell to provide residual function. Other CFTR mutations that reduce conductance and/or gating, such as Rl 17H, result in a normal quantity of CFTR channels at the surface of the cell, but the functional level is low, resulting in residual function. In some embodiments, the CFTR residual function mutation is selected from R117H, S1235R, I1027T, R668C, G576A, M470V, L997F, R75Q, R1070Q, R31C, D614G, G1069R, R1162L, E56K, A1067T, E193K, and K1060T. In some embodiments, the CFTR residual function mutation is selected from R117H, S1235R, I1027T, R668C, G576A, M470V, L997F, R75Q, R1070Q, R31C, D614G, G1069R, R1162L, E56K, and A1067T.

Residual CFTR function can be characterized at the cellular (in vitro) level using cell based assays, such as an FRT assay (Van Goar, F. et al. (2009) PNAS Vol. 106, No. 44, 18825-18830; and Van Goor, F. et al. (2011) PNAS Vol. 108, No. 46, 18843-18846), to measure the amount of chloride transport through the mutated CFTR channels. Residual function mutations result in a reduction but not complete elimination of CFTR dependent ion transport. In some embodiments, residual function mutations result in at least about 10% reduction of CFTR activity in an FRT assay. In some embodiments, the residual function mutations result in up to about 90% reduction in CFTR activity in an FRT assay.

Patients with an F508del/residual function genotype are defined as patients that are heterozygous F508del-CFTR with a second CFTR allele that contains a mutation that results in reduced protein quantity or function at the cell surface which can produce partial CFTR activity.

Patients with an F508del/gating mutation genotype are defined as patients that are heterozygous F508del-CFTR with a second CFTR allele that contains a mutation associated with a gating defect and clinically demonstrated to be responsive to Compound III. Examples of such mutations include: G178R, S549N, S549R, G551D, G551S, G1244E, S1251N, S1255P, and G1349D.

In some embodiments, the methods of treating, lessening the severity of, or symptomatically treating cystic fibrosis disclosed herein are each independently produces an increase in chloride transport above the baseline chloride transport of the patient.

In some embodiments, in the methods of treating, lessening the severity of, or symptomatically treating cystic fibrosis disclosed herein, the patient is heterozygous for F508del, and the other CFTR genetic mutation is any CF-causing mutation. In some embodiments, the patient is heterozygous for F508del, and the other CFTR genetic mutation is any CF-causing mutation, and is expected to be and/or is responsive to any of the novel compounds disclosed herein, such as Compound 1, Compound II, Compound III and/or Compound IV genotypes based on in vitro and/or clinical data. In some embodiments, the patient is heterozygous for F508del, and the other CFTR genetic mutation is any CF-causing mutation, and is expected to be and/or is responsive to any combinations of (i) the novel compounds disclosed herein, such as Compound 1, and (ii) Compound II, and/or Compound III and/or Compound IV genotypes based on in vitro and/or clinical data.

In some embodiments, in the methods of treating, lessening the severity of, or symptomatically treating cystic fibrosis disclosed herein, the patient possesses a CFTR genetic mutation selected from any of the mutations listed in Table A.

TABLE A

| CF Mutations |
| --- |
| 078delT |
| 1078delT |
| I1234V |
| 1154insTC |
| 1161delC |
| 1213delT |
| 1248 + 1G→A |
| 1249 − 1G→A |
| 124del23bp |
| 1259insA |
| 1288insTA |
| 1341 + 1G->A |
| 1342 − 2A->C |
| 1461ins4 |
| 1471delA |
| 1497delGG |
| 1507del |
| 1525 − 1G→A |
| 1525 − 2A→G |
| 1548delG |
| 1577delTA |
| 1609del CA |
| 1677delTA |
| 1716G/A |
| 1717 − 1G→A |
| 1717 − 8G→A |
| 1782delA |
| 1811 + 1.6 kbA->G |
| 1811 + 1G->C |
| 1811 + 1.6 kbA→G |
| 1811 + 1G→C |
| 1812 − 1G->A |
| 1898 + 1G->A |
| 1812 − 1G→A |
| 1824delA |
| 182delT |
| 1119delA |
| 185 + 1G→T |
| 1898 + 1G->T |
| 1898 + 1G→A |
| 1898 + 1G→C |
| 1898 + 3A->G |
| 1898 + 5G->T |
| 1924del7 |
| 1949del84 |
| 2043delG |
| 2055del9→A |
| 2105-2117del13insAGAAA |
| 2118del14 |
| 2143delT |
| 2183AA->G+ |
| 2183AA→G |
| 2183AA→G$^a$ |
| 2183delAA->G# |
| 2183delAA→G |
| 2184delA |
| 2184insA |
| 2307insA |
| 2347delG |
| 2556insAT |
| 2585delT |
| 2594delGT |
| 2622 + 1G->A |
| 2622 + IG->A |
| 2659delC |
| 2711delT |
| 271delT |

TABLE A-continued

CF Mutations

| | |
|---|---|
| 2721del11 | 1548delG |
| 2732insA | 675del4 |
| 2789 + 2insA | 711 + 1G->T |
| 2789 + 5G→A | 711 + 3A->G |
| 2790 – 1G→C | 711 + 1G→T |
| 2790 – IG->C | 711 + 3A→G |
| 2869insG | 711 + 5G→A |
| 2896insAG | 712 – 1G->T |
| 2942insT | 7T |
| 2957delT | 852del22 |
| 296 + 1G→A | 935delA |
| 2991del32 | 991del5 |
| 3007delG | A1006E |
| 3028delA | A120T |
| 3040G→C | A234D |
| 306insA | A349V |
| 306insA | A455E |
| 1138insG | A613T |
| 3120G→A | A46D |
| 3121 – 1G→A | A46Db |
| 3121 – 2A→G | A559T |
| 3121 – 977_3499 + 248 del2515 | A559Tb |
| | A561E |
| 3132delTG | C276X |
| 3141del9 | C524R |
| 3171delC | C524X |
| 3195del6 | CFTRdel2, 3 |
| 3199del6 | CFTRdele22-23 |
| 3272 – 26A->G | D110E |
| 3500 – 2A→G | D110H |
| 3600 + 2insT | D1152H |
| 365-366insT | D1270N |
| 3659delC | D192G |
| 3667ins4 | D443Y |
| 3737delA | D513G |
| 3791delC | D579G |
| 3821delT | D614G |
| 3849 + 10 kbC→T | D836Y |
| 3849 + IO kbC->T | D924N |
| 3850 – 1G→A | D979V |
| 3850 – 3T->G | E1104X |
| 3850 – IG->A | E116K |
| 3876delA | E1371X |
| 3878delG | E193K |
| 3905InsT | E193X |
| 3905insT | E403D |
| 394delTT | E474K |
| 4005 + 1G->A | E56K |
| 4005 + 2T->C | E585X |
| 4005 + 1G→A | E588V |
| 4005 + IG->A | E60K |
| 4010del4 | E822K |
| 4015delA | E822X |
| 4016insT | E831X |
| 4021dupT | E92K |
| 4040delA | E92X |
| 405 + 1G→A | F10165 |
| 405 + 3A→C | F1052V |
| 405 + IG->A | F1074L |
| 406 – 1G→A | F1099L |
| 406 – IG->A | F191V |
| 4209TGTT->A | F311del |
| 4209TGTT→AA | F311L |
| 4279insA | F508C |
| 4326delTC | F508del |
| 4374 + 1G→T | F575Y |
| 4374 + IG->T | G1061R |
| 4382delA | G1069R |
| 4428insGA | G1244E |
| 442delA | G1249R |
| 457TAT→G | G126D |
| 541delC | G1349D |
| 574delA | G149R |
| 5T | G178R |
| 621 + 1G→T | G194R |
| 621 + 3A->G | G194V |
| 663delT | G27R |
| 663delT | G27X |

TABLE A-continued

CF Mutations

| |
|---|
| G314E |
| G330X |
| G458V |
| G463V |
| G480C |
| G542X |
| G550X |
| G551D |
| G551S |
| G576A |
| G622D |
| G628R |
| G628R(G->A) |
| G970D |
| G673X |
| G85E |
| G91R |
| G970R |
| G970R |
| H1054D |
| H1085P |
| H1085R |
| H1375P |
| H139R |
| H199R |
| H199Y |
| H609R |
| H939R |
| I1005R |
| I1027T |
| I1234V |
| I1269N |
| I1366N |
| I148T |
| I175V |
| I3336K |
| I502T |
| I506S |
| I506T |
| I507del |
| I507del |
| I601F |
| I618T |
| I807M |
| I980K |
| IVS14b + 5G->A |
| K710X |
| K710X |
| K710X |
| L102R |
| L1065P |
| L1077P |
| L1077Pb |
| L1254X |
| L1324P |
| L1335P |
| L138ins |
| L1480P |
| L15P |
| L165S |
| L206W |
| L218X |
| L227R |
| L320V |
| L346P |
| L453S |
| L467P |
| L467Pb |
| L558S |
| L571S |
| L732X |
| L927P |
| L967S |
| L997F |
| M1101K |
| M1101R |
| M152V |
| M1T |

TABLE A-continued

CF Mutations

| |
|---|
| M1V |
| M265R |
| M470V |
| M952I |
| M952T |
| N1303K |
| P205S |
| P574H |
| P5L |
| P67L |
| P750L |
| P99L |
| Q1100P |
| Q1291H |
| Q1291R |
| Q1313X |
| Q1382X |
| Q1411X |
| Q1412X |
| Q220X |
| Q237E |
| Q237H |
| Q452P |
| Q290X |
| Q359K/T360K |
| Q39X |
| Q414 |
| Q414X |
| E585X |
| Q493X |
| Q525X |
| Q552X |
| Q685X |
| Q890X |
| Q890X |
| Q98R |
| Q98X |
| R1066C |
| R1066H |
| R1066M |
| R1070Q |
| R1070W |
| R1102X |
| R1158X |
| R1162L |
| R1162X |
| R117C |
| R117G |
| R117H |
| R117L |
| R117P |
| R1283M |
| R1283S |
| R170H |
| R258G |
| R31C |
| R31L |
| R334L |
| R334Q |
| R334W |
| R347H |
| R347L |
| R347P |
| R352Q |
| R352W |
| R516G |
| R553Q |
| R553X |
| R560K |
| R560S |
| R560T |
| R668C |
| R709X |
| R74W |
| R751L |
| R75Q |
| R75X |
| R764X |

TABLE A-continued

CF Mutations

R792G
R792X
R851X
R933G
S1118F
S1159F
S1159P
S1196X
S1235R
S1251N
S1255P
S1255X
S13F
S341P
S434X
S466X
S489X
S492F
S4X
S549N
S549R
S549R(A->C)
S549R(T->G)
S589N
S737F
S912L
S912X
S945L
S977F
T1036N
T1053I
T1246I
T338I
T604I
V1153E
V1240G
V1293G
V201M
V232D
V456A
V456F
V520F
V562I
V754M
W1089X
W1098C
W1098R
W1098X
W1204X
W1282R
W1282X
W361R
W401X
W496X
W57G
W57R
W57X
W846X
Y1014C
Y1032C
Y1092X
Y109N
Y122X
Y161D
Y161S
Y563D
Y563N
Y569C
Y569D
Y569Db
Y849X
Y913C
Y913X

In some embodiments, in the methods of treating, lessening the severity of, or symptomatically treating cystic fibrosis disclosed herein, the patient possesses a CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, 621+3A→G, 1949del84, 3141del9, 3195del6, 3199del6, 3905InsT, 4209TGTT→A, A1006E, A120T, A234D, A349V, A613T, C524R, D192G, D443Y, D513G, D836Y, D924N, D979V, E116K, E403D, E474K, E588V, E60K, E822K, F1016S, F1099L, F191V, F311del, F311L, F508C, F575Y, G1061R, G1249R, G126D, G149R, G194R, G194V, G27R, G314E, G458V, G463V, G480C, G622D, G628R, G628R(G→A), G91R, G970D, H1054D, H1085P, H1085R, H1375P, H139R, H199R, H609R, H939R, I1005R, I1234V, I1269N, I1366N, I175V, I502T, I506S, I506T, I601F, I618T, I807M, I980K, L102R, L1324P, L1335P, L138ins, L1480P, L15P, L165S, L320V, L346P, L453S, L571S, L967S, M1101R, M152V, MIT, M1V, M265R, M952I, M952T, P574H, P5L, P750L, P99L, Q1100P, Q1291H, Q1291R, Q237E, Q237H, Q452P, Q98R, R1066C, R1066H, R117G, R117L, R117P, R1283M, R1283S, R170H, R258G, R31L, R334L, R334Q, R347L, R352R, R516G, R553Q, R751L, R792G, R933G, S1118F, S1159F, S1159P, S13F, S549R(A→C), S549R(T→G), S589N, S737F, S912L, T1036N, T1053I, T1246I, T604I, V1153E, V1240G, V1293G, V201M, V232D, V456A, V456F, V562I, W1098C, W1098R, W1282R, W361R, W57G, W57R, Y1014C, Y1032C, Y109N, Y161D, Y161S, Y563D, Y563N, Y569C, and Y913C.

In some embodiments, the patient has at least one combination mutation chosen from: G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, and 621+3A→G.

In some embodiments, the patient has at least one combination mutation chosen from: 1949del84, 3141del9, 3195del6, 3199del6, 3905InsT, 4209TGTT→A, A1006E, A120T, A234D, A349V, A613T, C524R, D192G, D443Y, D513G, D836Y, D924N, D979V, E116K, E403D, E474K, E588V, E60K, E822K, F1016S, F1099L, F191V, F311del, F311L, F508C, F575Y, G1061R, G1249R, G126D, G149R, G194R, G194V, G27R, G314E, G458V, G463V, G480C, G622D, G628R, G628R(G→A), G91R, G970D, H1054D, H1085P, H1085R, H1375P, H139R, H199R, H609R, H939R, I1005R, I1234V, I1269N, I1366N, I175V, I502T, I506S, I506T, I601F, I618T, I807M, I980K, L102R, L1324P, L1335P, L138ins, L1480P, L15P, L165S, L320V, L346P, L453S, L571S, L967S, M1101R, M152V, MIT, M1V, M265R, M952I, M952T, P574H, P5L, P750L, P99L, Q1100P, Q1291H, Q1291R, Q237E, Q237H, Q452P, Q98R, R1066C, R1066H, R117G, R117L, R117P, R1283M, R1283S, R170H, R258G, R31L, R334L, R334Q, R347L, R352W, R516G, R553Q, R751L, R792G, R933G, S1118F, S1159F, S1159P, S13F, S549R(A→C), S549R(T→G), S589N, S737F, S912L, T1036N, T1053I, T1246I, T604I, V1153E, V1240G, V1293G, V201M, V232D, V456A, V456F, V562I, W1098C, W1098R, W1282R, W361R, W57G, W57R, Y1014C, Y1032C, Y109N, Y161D, Y161S, Y563D, Y563N, Y569C, and Y913C.

In some embodiments, in the methods of treating, lessening the severity of, or symptomatically treating cystic fibrosis disclosed herein, the patient possesses a CFTR genetic mutation G551D. In some embodiments, the patient is homozygous for the G551D genetic mutation. In some embodiments, the patient is heterozygous for the G551D genetic mutation. In some embodiments, the patient is heterozygous for the G551D genetic mutation, having the G551D mutation on one allele and any other CF-causing mutation on the other allele. In some embodiments, the patient is heterozygous for the G551D genetic mutation on one allele and the other CF-causing genetic mutation on the other allele is any one of F508del, G542X, N1303K, W1282X, R117H, R553X, 1717-1G→A, 621+1G→T, 2789+5G→A, 3849+10kbC→T, R1162X, G85E, 3120+1G→A, ΔI507, 1898+1G→A, 3659delC, R347P, R560T, R334W, A455E, 2184delA, or 711+1G→T. In some embodiments, the patient is heterozygous for the G551D genetic mutation, and the other CFTR genetic mutation is F508del. In some embodiments, the patient is heterozygous for the G551D genetic mutation, and the other CFTR genetic mutation is R117H.

In some embodiments, in the methods of treating, lessening the severity of, or symptomatically treating cystic fibrosis disclosed herein, the patient possesses a CFTR genetic mutation F508del. In some embodiments, the patient is homozygous for the F508del genetic mutation. In some embodiments, the patient is heterozygous for the F508del genetic mutation wherein the patient has the F508del genetic mutation on one allele and any CF-causing genetic mutation on the other allele. In some embodiments, the patient is heterozygous for F508del, and the other CFTR genetic mutation is any CF-causing mutation, including, but not limited to G551D, G542X, N1303K, W1282X, R117H, R553X, 1717-1G→A, 621+1G→T, 2789+5G→A, 3849+10kbC→T, R1162X, G85E, 3120+1G→A, ΔI507, 1898+1G→A, 3659delC, R347P, R560T, R334W, A455E, 2184delA, or 711+1G→T. In some embodiments, the patient is heterozygous for F508del, and the other CFTR genetic mutation is G551D. In some embodiments, the patient is heterozygous for F508del, and the other CFTR genetic mutation is R117H.

In some embodiments, the patient has at least one combination mutation chosen from:
D443Y;G576A;R668C,
F508C;S1251N,
G576A; R668C,
G970R; M470V,
R74W;D1270N,
R74W;V201M, and
R74W;V201M;D1270N.

In some embodiments, in the methods of treating, lessening the severity of, or symptomatically treating cystic fibrosis disclosed herein, the patient possesses a CFTR genetic mutation selected from G178R, G551S, G970R, G1244E, S1255P, G1349D, S549N, S549R, S1251N, E193K, F1052V and G1069R. In some embodiments, the patient possesses a CFTR genetic mutation selected from G178R, G551S, G970R, G1244E, S1255P, G1349D, S549N, S549R and S1251N. In some embodiments, the patient possesses a CFTR genetic mutation selected from E193K, F1052V and G1069R. In some embodiments, the method produces an increase in chloride transport relative to baseline chloride transport of the patient of the patient.

In some embodiments, in the methods of treating, lessening the severity of, or symptomatically treating cystic fibrosis disclosed herein, the patient possesses a CFTR genetic mutation selected from R117C, D110H, R347H, R352Q, E56K, P67L, L206W, A455E, D579G, S1235R, S945L, R1070W, F1074L, D110E, D1270N and D1152H.

In some embodiments, the patient possesses a CFTR genetic mutation selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G. In some embodiments, the patient possesses a CFTR genetic mutation selected from 1717-1G→A, 1811+1.6kbA→G, 2789+5G→A, 3272-26A→G and 3849+10kbC→T. In some embodiments, the patient possesses a CFTR genetic mutation selected from 2789+5G→A and 3272-26A→G.

In some embodiments, in the methods of treating, lessening the severity of, or symptomatically treating cystic fibrosis disclosed herein, the patient possesses a CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and human CFTR mutations selected from F508del, R117H, and G551D.

In some embodiments, in the methods of treating, lessening the severity of, or symptomatically treating cystic fibrosis disclosed herein, the patient possesses a CFTR genetic mutation selected from G178R, G551S, G970R, G1244E, S1255P, G1349D, S549N, S549R, S1251N, E193K, F1052V, G1069R, R117C, D110H, R347H, R352Q, E56K, P67L, L206W, A455E, D579G, S1235R, S945L, R1070W, F1074L, D110E, D1270N, D1152H, 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C, 621+3A→G, and a CFTR mutation selected from F508del, R117H, and G551D; and a CFTR mutations selected from F508del, R117H, and G551D.

In some embodiments, the patient possesses a CFTR genetic mutation selected from G178R, G551S, G970R, G1244E, S1255P, G1349D, S549N, S549R, S1251N, E193K, F1052V and G1069R, and a human CFTR mutation selected from F508del, R117H, and G551D. In some embodiments, the patient possesses a CFTR genetic mutation selected from G178R, G551S, G970R, G1244E, S1255P, G1349D, S549N, S549R and S1251N, and a human CFTR mutation selected from F508del, R117H, and G551D. In some embodiments, the patient possesses a CFTR genetic mutation selected from E193K, F1052V and G1069R, and a human CFTR mutation selected from F508del, R117H, and G551D.

In some embodiments, the patient possesses a CFTR genetic mutation selected from R117C, D110H, R347H, R352Q, E56K, P67L, L206W, A455E, D579G, S1235R, S945L, R1070W, F1074L, D110E, D1270N and D1152H, and a human CFTR mutation selected from F508del, R117H, and G551D.

In some embodiments, the patient possesses a CFTR genetic mutation selected from 1717-1G→A, 621+1G→T, 3120+1G→A, 1898+1G→A, 711+1G→T, 2622+1G→A, 405+1G→A, 406-1G→A, 4005+1G→A, 1812-1G→A, 1525-1G→A, 712-1G→T, 1248+1G→A, 1341+1G→A, 3121-1G→A, 4374+1G→T, 3850-1G→A, 2789+5G→A, 3849+10kbC→T, 3272-26A→G, 711+5G→A, 3120G→A, 1811+1.6kbA→G, 711+3A→G, 1898+3A→G, 1717-8G→A, 1342-2A→C, 405+3A→C, 1716G/A, 1811+1G→C, 1898+5G→T, 3850-3T→G, IVS14b+5G→A, 1898+1G→T, 4005+2T→C and 621+3A→G, and a human CFTR mutation selected from F508del, R117H, and G551D. In some embodiments, the patient possesses a CFTR genetic mutation selected from 1717-1G→A, 1811+1.6kbA→G, 2789+5G→A, 3272-26A→G and 3849+10kbC→T, and a human CFTR mutation selected from F508del, R117H, and G551D. In some embodiments, the patient possesses a CFTR genetic mutation selected from 2789+5G→A and 3272-26A→G, and a human CFTR mutation selected from F508del, R117H.

In some embodiments, the patient is heterozygous having a CF-causing mutation on one allele and a CF-causing mutation on the other allele. In some embodiments, the patient is heterozygous for F508del, and the other CFTR genetic mutation is any CF-causing mutation, including, but not limited to F508del on one CFTR allele and a CFTR mutation on the second CFTR allele that is associated with minimal CFTR function, residual CFTR function, or a defect in CFTR channel gating activity.

In some embodiments, the CF-causing mutation is selected from Table A. In some embodiments, the CF-causing mutation is selected from Table B. In some embodiments, the CF-causing mutation is selected from Table C. In some embodiments, the CF-causing mutation is selected from FIG. 1. In some embodiments, the patient is heterozygous having a CF-causing mutation on one CFTR allele selected from the mutations listed in the table from FIG. 1 and a CF-causing mutation on the other CFTR allele is selected from the CFTR mutations listed in Table B:

TABLE B

| CFTR Mutations | | | |
|---|---|---|---|
| Q39X | 712 – 1G→T | | T338I |
| W57X | 405 + 1G→A | | R347P |
| E60X | 405 + 3A→C | | L927P |
| R75X | 406 – 1G→A | | G85E |
| E92X | 621 + 1G→T | | S341P |
| Q98X | 1248 + 1G→A | | L467P |
| Y122X | 1341 + 1G→A | | I507del |
| L218X | 1717 – 1G→A | | V520F |
| Q220X | 1811 + 1.6 kbA→G | | A559T |
| C276X | 1811 + 1G→C | | R560T |
| Q290X | 1812 – 1G→A | | R560S |
| G330X | 1898 + 1G→A | | A561E |
| W401X | 2622 + 1G→A | | Y569D |
| Q414X | 3120 + 1G→A | | L1065P |
| S434X | 3120G→A | | R1066C |
| S466X | 3850 – 1G→A | | R1066M |
| S489X | 4005 + 1G→A | | L1077P |
| Q493X | 4374 + 1G→T | | H1085R |
| W496X | 663delT | | M1101K |
| Q525X | 2183AA→G | | N1303K |
| G542X | CFTRdel2,3 | | 3849 + 10 kbC→T |
| Q552X | 3659delC | | 3272 – 26A→G |
| R553X | 394delTT | | 711 + 3A→G |
| E585X | 2184insA | | E56K |
| G673X | 3905insT | | P67L |
| R709X | 2184delA | | R74W |
| K710X | 1078delT | | D110E |
| L732X | 1154insTC | | D110H |
| R764X | 2183delAA→G | | R117C |
| R785X | 2143delT | | L206W |
| R792X | 1677delTA | | R347H |
| E822X | 3876delA | | R352Q |
| W846X | 2307insA | | A455E |
| R851X | 4382delA | | D579G |
| Q890X | 4016insT | | E831X |
| S912X | 2347delG | | S945L |
| W1089X | 3007delG | | S977F |
| Y1092X | 574delA | | F1052V |
| E1104X | 2711delT | | R1070W |
| R1158X | 3791delC | | F1074L |
| R1162X | CFTRdele22-23 | | D1152H |
| S1196X | 457TAT→G | | D1270N |
| W1204X | 2043delG | | G178R |
| S1255X | 2869insG | | S549N |
| W1282X | 3600 + 2insT | | S549R |
| Q1313X | 3737delA | | G551D |
| 621 + 1G→T | 4040delA | | G551S |
| 711 + 1G→T | 541delC | | G1244E |
| 711 + 5G→A | A46D | | S1251N |
| S1255P | | | |
| G1349D | | | |

TABLE C

| Criteria | Mutation | | | | |
|---|---|---|---|---|---|
| Truncation mutations or nonsense mutations % PI > 50% and/or | Q2X S4X W19X | L218X Q220X Y275X | Q525X G542X G550X | R792X E822X W882X | E1104X W1145X R1158X |

TABLE C-continued

CFTR Mutations

| Criteria | Mutation | | | | |
|---|---|---|---|---|---|
| SwCl⁻ > 86 mmol/L<br>No full-length<br>protein | G27X<br>Q39X<br>W57X<br>E60X<br>R75X<br>L88X<br>E92X<br>Q98X<br>Y122X<br>E193X<br>W216X | C276X<br>Q290X<br>G330X<br>W401X<br>Q414X<br>S434X<br>S466X<br>S489X<br>Q493X<br>W496X<br>C524X | Q552X<br>R553X<br>E585X<br>G673X<br>Q685X<br>R709X<br>K710X<br>Q715X<br>L732X<br>R764X<br>R785X | W846X<br>Y849X<br>R851X<br>Q890X<br>S912X<br>Y913X<br>Q1042X<br>W1089X<br>Y1092X<br>W1098X<br>R1102X | R1162X<br>S1196X<br>W1204X<br>L1254X<br>S1255X<br>W1282X<br>Q1313X<br>Q1330X<br>E1371X<br>Q1382X<br>Q1411X |
| Splice mutations or<br>Carnonical splic<br>mutations<br>% PI > 50% and/or<br>SwCl⁻ > 86 mmol/L<br>No or little mature<br>mRNA | 185 + 1G→T<br>296 + 1G→A<br>296 + 1G→T<br>405 + 1G→A<br>405 + 3A→C<br>406 − 1G→A<br>621 + 1G→T<br>711 + 1G→T | 711 + 5G→A<br>712 − 1G→T<br>1248 + 1G→A<br>1249 − 1G→A<br>1341 + 1G→A<br>1525 − 2A→G<br>1525 − 1G→A | 1717 − 8G→A<br>1717 − 1G→A<br>1811 + 1G→C<br>1811 + 1.6kbA→G<br>1811 + 1643G→T<br>1812 − 1G→A<br>1898 + 1G→A<br>1898 + 1G→C | 2622 + 1G→A<br>2790 − 1G→C<br>3040G→C<br>(G970R)<br>3120G→A<br>3120 + 1G→A<br>3121 − 2A→G | 3121 − 1G→A<br>3500 − 2A→G<br>3600 + 2insT<br>3850 − 1G→A<br>4005 + 1G→A<br>4374 + 1G→T |
| Small (≤3 nucleotide)<br>insertion/deletion<br>(ins/del) frameshift<br>mutations<br>% PI > 50% and/or<br>SwCl⁻ > 86 mmol/L<br>Garbled and/or<br>truncated protein | 182delT<br>306insA<br>306delTAGA<br>365-366insT<br>394delTT<br>442delA<br>444delA<br>457TAT→G<br>541delC<br>574delA<br>663delT<br>849delG<br>935delA | 1078delT<br>1119delA<br>1138insG<br>1154insTC<br>1161delC<br>1213delT<br>1259insA<br>1288insTA<br>1343delG<br>1471delA<br>1497delGG<br>1548delG<br>1609del CA | 1677delTA<br>1782delA<br>1824delA<br>1833delT<br>2043delG<br>2143delT<br>2183AA→Gᵃ<br>2184delA<br>2184insA<br>2307insA<br>2347delG<br>2585delT<br>2594delGT | 2711delT<br>2732insA<br>2869insG<br>2896insAG<br>2942insT<br>2957delT<br>3007delG<br>3028delA<br>3171delC<br>3171insC<br>3271delGG<br>3349insT<br>3659delC | 3737delA<br>3791delC<br>3821delT<br>3876delA<br>3878delG<br>3905insT<br>4016insT<br>4021dupT<br>4022insT<br>4040delA<br>4279insA<br>4326delTC |
| Non-small (>3<br>nucleotide)<br>insertion/deletion<br>(ins/del) frameshift<br>mutations<br>% PI > 50% and/or<br>SwCl⁻ > 86 mmol/L<br>Garbled and/or<br>truncated protein | CFTRdele1<br>CFTRdele2<br>CFTRdele2,3<br>CFTRdele2-4<br>CFTRdele3-10,14b-16<br>CFTRdele4-7<br>CFTRdele4-11<br>CFTR50kbdel<br>CFTRdup6b-10<br>CFTRdele11<br>CFTRdele13,14a<br>CFTRdele14b-17b | | CFTRdele16-17b<br>CFTRdele17a,17b<br>CFTRdele17a-18<br>CFTRdele19<br>CFTRdele19-21<br>CFTRdele21<br>CFTRdele22-24<br>CFTRdele22,23<br>124del23bp<br>602del14<br>852del22<br>991del5 | 1461ins4<br>1924del7<br>2055del9→A<br>2105-2117del13insAGAAA<br>2372del8<br>2721del11<br>2991del32<br>3121 − 977_3499 + 248del2515<br>3667ins4<br>4010del4<br>4209TGTT→AA | |
| Class II, III, IV<br>mutations not<br>responsive to<br>Compound II<br>Compound III, or<br>Compound<br>II/Compound III/or<br>Missense muatations<br>that:<br>% PI > 50% and/or<br>SwCl⁻ > 86<br>mmol/L<br>AND<br>Not responsive in<br>vitro to<br>Compound II,<br>Compound III, or<br>Compound<br>II/Compound III | A46Dᵇ<br>G85E<br>R347P<br>L467Pᵇ | V520F<br>A559Tᵇ<br>R560T<br>R560S<br>A561E<br>I507del | Y569Dᵇ<br>L1065P<br>R1066C<br>L1077Pb<br>M1101K | N1303K | |

CFTR: cystic fibrosis transmembrane conductance regulator; SwCl: sweat chloride

Source: CFTR2.org [Internet]. Baltimore (MD): Clinical and functional translation of CFTR. The Clinical and Functional Translation of CFTR (CFTR2), US Cystic Fibrosis Foundation, Johns Hopkins University, the Hospital for Sick Children. Available at: http://www.cftr2.org/. Accessed 15 Feb. 2016.

Notes:

% PI: percentage of F508del-CFTR heterozygous patients in the CFTR2 patient registry who are pancreatic insufficient; SwCl: mean sweat chloride of F508del-CFTR heterozygous patients in the CFTR2 patient registry.

ᵃAlso known as 2183delAA→G.

ᵇUnpublished data.

In some embodiments, the patient is: with F508del/MF (F/MF) genotypes (heterozygous for F508del and an MF mutation not expected to respond to CFTR modulators, such as Compound III); with F508del/F508del (F/F) genotype (homozygous for F508del); and/or with F508del/gating (F/G) genotypes (heterozygous for F508del and a gating mutation known to be CFTR modulator-responsive (e.g., Compound III-responsive). In some embodiments, the patient with F508del/MF (F/MF) genotypes has a MF mutation that is not expected to respond to Compound II, Compound III, and both of Compound II and Compound III. In some embodiments, the patient with F508del/MF (F/MF) genotypes has any one of the MF mutations in Table C.

In some embodiments, the patient is heterozygous for F508del, and the other CFTR genetic mutation is any CF-causing mutation, including truncation mutations, splice mutations, small (≤3 nucleotide) insertion or deletion (ins/del) frameshift mutations; non-small (>3 nucleotide) insertion or deletion (ins/del) frameshift mutations; and Class II, III, IV mutations not responsive to Compound III alone or in combination with Compound II or Compound IV.

In some embodiments, the patient is heterozygous for F508del, and the other CFTR genetic mutation is a truncation mutation. In some specific embodiments, the truncation mutation is a truncation mutation listed in Table C.

In some embodiments, the patient is heterozygous for F508del, and the other CFTR genetic mutation is a splice mutation. In some specific embodiments, the splice mutation is a splice mutation listed in Table C.

In some embodiments, the patient is heterozygous for F508del, and the other CFTR genetic mutation is a small (≤3 nucleotide) insertion or deletion (ins/del) frameshift mutation. In some specific embodiments, the small (≤3 nucleotide) insertion or deletion (ins/del) frameshift mutation is a small (≤3 nucleotide) insertion or deletion (ins/del) frameshift mutation listed in Table C.

In some embodiments, the patient is heterozygous for F508del, and the other CFTR genetic mutation is any CF-causing mutation expected to be and/or is responsive to, based on in vitro and/or clinical data, any combination of (i) a novel compound chosen from those disclosed herein (e.g., compounds of Formula (I), (II), (III), (IV), or (V), and pharmaceutically acceptable salts thereof, and their deuterated derivatives), and (ii) Compound II, and/or Compound III, and/or Compound IV.

In some embodiments, the patient is heterozygous for F508del, and the other CFTR genetic mutation is any CF-causing mutation expected to be and/or is responsive, based on in vitro and/or clinical data, to the triple combination of a novel compound chosen from those disclosed herein (e.g., compounds of Formula (I), (II), (III), (IV), or (V), and pharmaceutically acceptable salts thereof, and their deuterated derivatives), and Compound II, and Compound III.

In some embodiments, the patient is heterozygous for F508del, and the other CFTR genetic mutation is a non-small (>3 nucleotide) insertion or deletion (ins/del) frameshift mutation. In some specific embodiments, the non-small (>3 nucleotide) insertion or deletion (ins/del) frameshift mutation is a non-small (>3 nucleotide) insertion or deletion (ins/del) frameshift mutation listed in Table 5B.

In some embodiments, the patient is heterozygous for F508del, and the other CFTR genetic mutation is a Class II, III, IV mutations not responsive to Compound III alone or in combination with Compound II or Compound IV. In some specific embodiments, the Class II, III, IV mutations not responsive to Compound III alone or in combination with Compound II or Compound IV is a Class II, III, IV mutations not responsive to Compound III alone or in combination with Compound II or Compound IV listed in Table C.

In some embodiments, the patient is heterozygous for F508del, and the other CFTR genetic mutation is any mutation listed in Table C.

In some embodiments, the patient is heterozygous for F508del, and the other CFTR genetic mutation is any mutation, but other than F508del, listed in Table A, B, C, and FIG. 1.

In some embodiments, the patient is heterozygous for F508del, and the other CFTR genetic mutation is any mutation listed in Table A. In some embodiments, the patient is heterozygous for F508del, and the other CFTR genetic mutation is any mutation listed in Table B. In some embodiments, the patient is heterozygous for F508del, and the other CFTR genetic mutation is any mutation listed in Table C. In some embodiments, the patient is heterozygous for F508del, and the other CFTR genetic mutation is any mutation listed in FIG. 1.

In some embodiments, the patient is homozygous for F508del.

In some embodiments, the patient is heterozygous having one CF-causing mutation on one CFTR allele selected from the mutations listed in the table from FIG. 1 and another CF-causing mutation on the other CFTR allele is selected from the CFTR mutations listed in Table C.

In some embodiments, the triple combinations are administered to a patient who has one F508del mutation and one minimal function mutation, and who has not taken any of said at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof.

In some embodiments, the composition disclosed herein is useful for treating, lessening the severity of, or symptomatically treating cystic fibrosis in patients who exhibit residual CFTR activity in the apical membrane of respiratory and non-respiratory epithelia. The presence of residual CFTR activity at the epithelial surface can be readily detected using methods known in the art, e.g., standard electrophysiological, biochemical, or histochemical techniques. Such methods identify CFTR activity using in vivo or ex vivo electrophysiological techniques, measurement of sweat or salivary $Cl^-$ concentrations, or ex vivo biochemical or histochemical techniques to monitor cell surface density. Using such methods, residual CFTR activity can be readily detected for patients that are heterozygous or homozygous for a variety of different mutations, including patients heterozygous for the most common mutation, F508del, as well as other mutations such as the G551D mutation, or the R117H mutation. In some embodiments, compositions disclosed herein are useful for treating, lessening the severity of, or symptomatically treating cystic fibrosis in patients who exhibit little to no residual CFTR activity. In some embodiments, compositions disclosed herein are useful for treating, lessening the severity of, or symptomatically treating cystic fibrosis in patients who exhibit little to no residual CFTR activity in the apical membrane of respiratory epithelia.

In some embodiments, the compositions disclosed herein are useful for treating or lessening the severity of cystic fibrosis in patients who exhibit residual CFTR activity using pharmacological methods. Such methods increase the amount of CFTR present at the cell surface, thereby inducing a hitherto absent CFTR activity in a patient or augmenting the existing level of residual CFTR activity in a patient.

In some embodiments, the compositions disclosed herein are useful for treating or lessening the severity of cystic fibrosis in patients with certain genotypes exhibiting residual CFTR activity.

In some embodiments, compositions disclosed herein are useful for treating, lessening the severity of, or symptomatically treating cystic fibrosis in patients within certain clinical phenotypes, e.g., a mild to moderate clinical phenotype that typically correlates with the amount of residual CFTR activity in the apical membrane of epithelia. Such phenotypes include patients exhibiting pancreatic sufficiency.

In some embodiments, the compositions disclosed herein are useful for treating, lessening the severity of, or symptomatically treating patients diagnosed with pancreatic sufficiency, idiopathic pancreatitis and congenital bilateral absence of the vas deferens, or mild lung disease wherein the patient exhibits residual CFTR activity.

In some embodiments, this disclosure relates to a method of augmenting or inducing anion channel activity in vitro or in vivo, comprising contacting the channel with a composition disclosed herein. In some embodiments, the anion channel is a chloride channel or a bicarbonate channel. In some embodiments, the anion channel is a chloride channel. In some embodiments of the methods of treating cystic fibrosis disclosed herein, the absolute change in patient's percent predicted forced expiratory volume in one second (ppFEV$_1$) after 29 days of administration of at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof ranges from 3% to 40% relative to the ppFEV1 of the patient prior to said administration. In some embodiments of the methods of treating cystic fibrosis disclosed herein, the absolute change in ppFEV$_1$ after 29 days of administration of at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof ranges from 3% to 35% relative to the ppFEV1 of the patient prior to said administration.

In some embodiments of the methods of treating cystic fibrosis disclosed herein, the absolute change in ppFEV$_1$ after 29 days of administration of at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof ranges from 7% to 40% relative to the ppFEV1 of the patient prior to said administration, such as from 8% to 40%, and further such as 11% to 40%.

In some embodiments of the methods of treating cystic fibrosis disclosed herein, the absolute change in ppFEV$_1$ after 29 days of administration of at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof ranges from 9% to 40% relative to the ppFEV1 of the patient prior to said administration, such as from 10% to 40%, and further such as 12% to 40%.

In some embodiments of the methods of treating cystic fibrosis disclosed herein, the absolute change in the patient's sweat chloride after 29 days of administration of at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof ranges from −6 to −65 mmol/L from baseline, i.e., relative to the sweat chloride of the patient prior to said administration. In some embodiments, the absolute change in sweat chloride of said patient ranges from −8 to −65 mmol/L. In some embodiments, the absolute change in sweat chloride of said patient ranges from −9 to −65 mmol/L. In some embodiments, the absolute change in sweat chloride of said patient ranges from −10 to −65 mmol/L. In some embodiments, the absolute change in sweat chloride of said patient ranges from −11 to −65 mmol/L. In some embodiments, the absolute change in sweat chloride of said patient ranges from −22 to −65 mmol/L. In some embodiments, the absolute change in sweat chloride of said patient ranges from −28 to −65 mmol/L. In some embodiments, the absolute change in sweat chloride of said patient ranges from −33 to −65 mmol/L.

In some embodiments, the absolute change in a patient's ppFEV$_1$ relative to the ppFEV1 of the patient prior to such administration of the triple combinations can be calculated as (postbaseline value−baseline value). The baseline value is defined as the most recent non-missing measurement collected before the first dose of study drug in the Treatment Period (Day 1).

The exact amount of a pharmaceutical composition required will vary from subject to subject, depending on the species, age, and general condition of the subject, the severity of the disease, the particular agent, its mode of administration, and the like. The compounds of this disclosure may be formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of this disclosure will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, such as a mammal, and even further such as a human.

In some embodiments, the disclosure also is directed to methods of treatment using isotope-labelled compounds of the afore-mentioned compounds, which, in some embodiments, are referred to as Compound I', Compound II', Compound III', Compound III-d' or Compound IV'. In some embodiments, Compound I', Compound II', Compound III', Compound III-d', Compound IV', or pharmaceutically acceptable salts thereof, wherein the formula and variables of such compounds and salts are each and independently as described above or any other embodiments described above, provided that one or more atoms therein have been replaced by an atom or atoms having an atomic mass or mass number which differs from the atomic mass or mass number of the atom which usually occurs naturally (isotope labelled). Examples of isotopes which are commercially available and suitable for the disclosure include isotopes of hydrogen, carbon, nitrogen, oxygen, phosphorus, fluorine and chlorine, for example $^2$H, $^3$H, $^{13}$C, $^{14}$C $^{15}$N, $^{18}$O, $^{17}$O, $^{31}$P, $^{32}$P $^{35}$S, $^{18}$F and $^{36}$Cl, respectively.

The isotope-labelled compounds and salts can be used in a number of beneficial ways. They can be suitable for medicaments and/or various types of assays, such as substrate tissue distribution assays. For example, tritium (3H)- and/or carbon-14 ($^{14}$C)-labelled compounds are particularly useful for various types of assays, such as substrate tissue distribution assays, due to relatively simple preparation and excellent detectability. For example, deuterium ($^2$H)-labelled ones are therapeutically useful with potential therapeutic advantages over the non-$^2$H-labelled compounds. In general, deuterium ($^2$H)-labelled compounds and salts can have higher metabolic stability as compared to those that are not isotope-labelled owing to the kinetic isotope effect described below. Higher metabolic stability translates directly into an increased in vivo half-life or lower dosages, which could be desired. The isotope-labelled compounds and salts can usually be prepared by carrying out the procedures disclosed in the synthesis schemes and the related description, in the example part and in the preparation part in the present text, replacing a non-isotope-labelled reactant by a readily available isotope-labelled reactant.

In some embodiments, the isotope-labelled compounds and salts are deuterium ($^2$H)-labelled ones. In some specific embodiments, the isotope-labelled compounds and salts are deuterium ($^2$H)-labelled, wherein one or more hydrogen atoms therein have been replaced by deuterium. In chemical structures, deuterium is represented as "D."

The deuterium ($^2$H)-labelled compounds and salts can manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_m/k_D$=2-7 are typical. For a further discussion, see S. L. Harbeson and R. D. Tung, *Deuterium In Drug Discovery and Development*, Ann. Rep. Med. Chem. 2011, 46, 403-417, incorporated in its entirety herein by reference.

The concentration of the isotope(s) (e.g., deuterium) incorporated into the isotope-labelled compounds and salt of the disclosure may be defined by the isotopic enrichment factor. The term "isotopic enrichment factor" as used herein means the ratio between the isotopic abundance and the natural abundance of a specified isotope. In some embodiments, if a substituent in a compound of the disclosure is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

When discovering and developing therapeutic agents, the person skilled in the art attempts to optimize pharmacokinetic parameters while retaining desirable in vitro properties. It may be reasonable to assume that many compounds with poor pharmacokinetic profiles are susceptible to oxidative metabolism.

Exemplary embodiments of the disclosure include:

1. A method of treating cystic fibrosis comprising administering to a patient in need thereof:

(A) 10 mg to 900 mg of at least one compound chosen from Compound I:

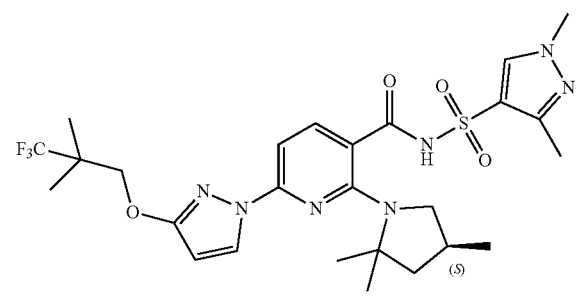

and pharmaceutically acceptable salts thereof daily; and (B) at least one compound chosen from (i) Compound II:

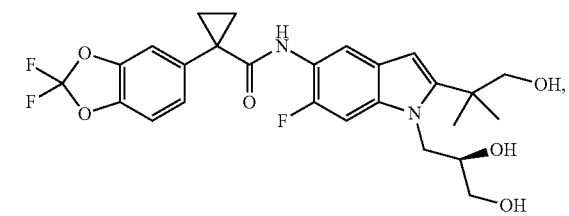 [SMILES: CC(C)(CO)c1cc2cc(NC(=O)C3(c4ccc5c(c4)OC(F)(F)O5)CC3)c(F)cc2n1C[C@@H](O)CO]

(ii) Compound III or Compound III-d:

(Compound III)

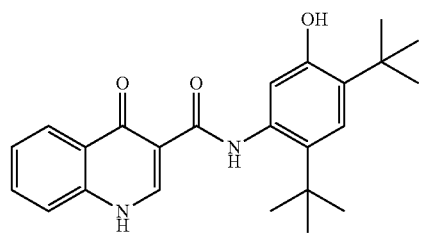

(Compound III-d)

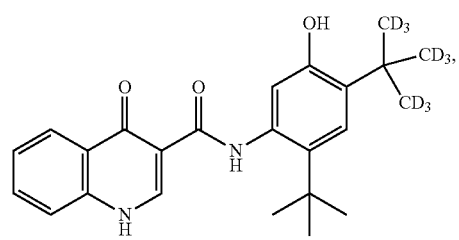

and
(iii) Compound IV:

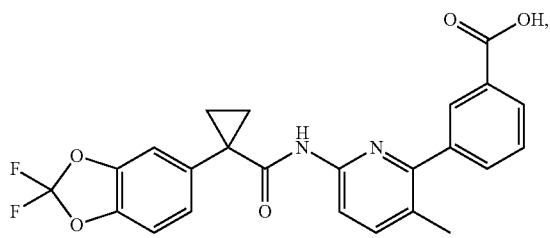 [SMILES: Cc1ccc(NC(=O)C2(c3ccc4c(c3)OC(F)(F)O4)CC2)nc1-c1cccc(C(=O)O)c1]

and
pharmaceutically acceptable salts of any of the foregoing.

2. The method according to embodiment 1, comprising administering to said patient: (a) at least one compound chosen from Compound I and pharmaceutically acceptable salts thereof, (b) at least one compound chosen from Compound II and pharmaceutically acceptable salts thereof, (c) and at least one compound chosen from (i) Compound III and pharmaceutically acceptable salts thereof, or (ii) Compound III-d and pharmaceutically acceptable salts thereof.

3. The method according to embodiment 1, comprising administering to said patient: (a) at least one compound chosen from Compound I and pharmaceutically acceptable salts thereof, (b) at least one compound chosen from Compound II and pharmaceutically acceptable salts thereof, and (c) at least one compound chosen from Compound IV and pharmaceutically acceptable salts thereof.

4. The method according to embodiment 1, comprising administering to said patient: (a) at least one compound chosen from Compound I and pharmaceutically acceptable salts thereof, (b) at least one compound chosen from (i) Compound III and pharmaceutically acceptable salts thereof, or (ii) Compound III-d and pharmaceutically acceptable salts thereof, and (c) at least one compound chosen from Compound IV and pharmaceutically acceptable salts thereof.

5. The method of according to embodiment 1, comprising administering to said patient: (i) at least one compound chosen from Compound I and pharmaceutically acceptable salts thereof, and at least one compound chosen from Compound II and pharmaceutically acceptable salts thereof, (ii) at least one compound chosen from Compound I and pharmaceutically acceptable salts thereof, and at least one compound chosen from Compound III and pharmaceutically acceptable salts thereof, (iii) at least one compound chosen from Compound I and pharmaceutically acceptable salts thereof, and at least one compound chosen from Compound III-d and pharmaceutically acceptable salts thereof, or (iv) at least one compound chosen from Compound I and pharmaceutically acceptable salts thereof, and at least one compound chosen from Compound IV and pharmaceutically acceptable salts thereof.

6. The method according to any one of embodiments 1-5, wherein 20 mg to 800 mg of at least one compound chosen from Compound I and pharmaceutically acceptable salts thereof is administered daily.

7. The method according to any one of embodiments 1-5, wherein 30 mg to 720 mg of at least one compound chosen from Compound I and pharmaceutically acceptable salts thereof is administered daily.

8. The method according to any one of embodiments 1-5, wherein 40 mg to 600 mg of at least one compound chosen from Compound I and pharmaceutically acceptable salts thereof is administered daily.

9. The method according to any one of embodiments 1-5, wherein 40 mg to 600 mg or 40 mg to 550 mg of at least one compound chosen from Compound I and pharmaceutically acceptable salts thereof is administered daily.

10. The method according to any one of embodiments 1-5, wherein 40 mg to 500 mg of at least one compound chosen from Compound I and pharmaceutically acceptable salts thereof is administered daily.

11. The method according to any one of embodiments 1-5, wherein 40 mg to 400 mg of at least one compound chosen from Compound I and pharmaceutically acceptable salts thereof is administered daily.

12. The method according to any one of embodiments 1-5, wherein 40 mg to 300 mg of at least one compound chosen from Compound I and pharmaceutically acceptable salts thereof is administered daily.

13. The method according to any one of embodiments 1-5, wherein 50 mg to 360 mg of at least one compound chosen from Compound I and pharmaceutically acceptable salts thereof is administered daily.

14. The method according to any one of embodiments 1-5, wherein 160 mg to 320 mg of at least one compound chosen from Compound I and pharmaceutically acceptable salts thereof is administered daily.

15. The method according to any one of embodiments 1-5, wherein 240 mg to 400 mg or 160 mg to 300 mg of at least one compound chosen from Compound I and pharmaceutically acceptable salts thereof is administered daily.

16. The method according to any one of embodiments 1-5, wherein 320 mg to 480 mg or 160 mg to 400 mg of at least one compound chosen from Compound I and pharmaceutically acceptable salts thereof is administered daily.

17. The method according to any one of embodiments 1-5, wherein 360 mg to 640 mg or 180 mg to 220 mg of at least one compound chosen from Compound I and pharmaceutically acceptable salts thereof is administered daily.

18. The method according to any one of embodiments 1-5, wherein 80 mg to 360 mg of at least one compound chosen from Compound I and pharmaceutically acceptable salts thereof is administered daily.

19. The method according to any one of embodiments 1-5, wherein 50 mg of at least one compound chosen from Compound I and pharmaceutically acceptable salts thereof is administered daily.

20. The method according to any one of embodiments 1-5, wherein 100 mg of at least one compound chosen from Compound I and pharmaceutically acceptable salts thereof is administered daily.

21. The method according to any one of embodiments 1-5, wherein 250 mg or 200 mg of at least one compound chosen from Compound I and pharmaceutically acceptable salts thereof is administered daily.

22. The method according to any one of embodiments 1-5, wherein 150 mg, 200 mg, 250 mg, 300 mg, 350 mg, 400 mg, 450 mg, 500 mg, 550 mg, or 600 mg of at least one compound chosen from Compound I and pharmaceutically acceptable salts thereof is administered daily.

23. The method according to any one of embodiments 1-22, wherein at least one compound chosen from Compound I and pharmaceutically acceptable salts thereof is administered as a single dose, once daily.

24. The method according to any one of embodiments 1-22, wherein at least one compound chosen from Compound I and pharmaceutically acceptable salts thereof is administered in two doses daily.

25. The method according to any one of embodiments 1-3, and 5, wherein 25 mg to 200 mg of at least one compound chosen from Compound II and pharmaceutically acceptable salts thereof is administered daily.

26. The method according to any one of embodiments 1-3, and 5, wherein 50 mg to 150 mg of at least one compound chosen from Compound II and pharmaceutically acceptable salts thereof is administered daily.

27. The method according to any one of embodiments 1-3, and 5, wherein 75 mg to 200 mg of at least one compound chosen from Compound II and pharmaceutically acceptable salts thereof is administered daily.

28. The method according to any one of embodiments 1-3, and 5, wherein 50 mg of at least one compound chosen from Compound II and pharmaceutically acceptable salts thereof is administered daily.

29. The method according to any one of embodiments 1-3, and 5, wherein 100 mg of at least one compound chosen from Compound II and pharmaceutically acceptable salts thereof is administered daily.

30. The method according to any one of embodiments 1-3, 5, and 25-29, wherein at least one compound chosen from Compound II and pharmaceutically acceptable salts thereof is administered as a single dose, once daily.

31. The method according to any one of embodiments 1-3, 5, and 25-29, wherein at least one compound chosen from Compound II and pharmaceutically acceptable salts thereof is administered in two doses daily.

32. The method according to any one of embodiments 1, 2, 4, and 5, wherein (i) 50 mg to 600 mg of at least one compound chosen from Compound III and pharmaceutically acceptable salts thereof is administered daily; or (ii) 50 mg to 400 mg of at least one compound chosen from Compound III-d and pharmaceutically acceptable salts thereof is administered daily.

33. The method according to any one of embodiments 1, 2, 4, and 5, wherein (i) 50 mg to 450 mg of at least one compound chosen from Compound III and pharmaceutically acceptable salts thereof is administered daily; or (ii) 50 mg to 300 mg of at least one compound chosen from Compound III-d and pharmaceutically acceptable salts thereof is administered daily.

34. The method according to any one of embodiments 1, 2, 4, and 5, wherein: (i) 100 mg to 400 mg of at least one compound chosen from Compound III and pharmaceutically acceptable salts thereof is administered daily; or (ii) 100 mg to 300 mg of at least one compound chosen from Compound III-d and pharmaceutically acceptable salts thereof is administered daily.

35. The method according to any one of embodiments 1, 2, 4, and 5, wherein: (i) 125 mg to 300 mg of at least one compound chosen from Compound III and pharmaceutically acceptable salts thereof is administered daily; or (ii) 125 mg to 300 mg of at least one compound chosen from Compound III-d and pharmaceutically acceptable salts thereof is administered daily.

36. The method according to any one of embodiments 1, 2, 4, and 5, wherein: (i) 150 mg to 300 mg of at least one compound chosen from Compound III and pharmaceutically acceptable salts thereof is administered daily; or (ii) 100 mg to 200 mg of at least one compound chosen from Compound III-d and pharmaceutically acceptable salts thereof is administered daily.

37. The method according to any one of embodiments 1, 2, 4, and 5, wherein: (i) 200 mg to 250 mg of at least one compound chosen from Compound III and pharmaceutically acceptable salts thereof is administered daily; or (ii) 125 mg to 200 mg of at least one compound chosen from Compound III-d and pharmaceutically acceptable salts thereof is administered daily.

38. The method according to any one of embodiments 1, 2, 4, and 5, wherein: (i) 300 mg or 600 mg of at least one compound chosen from Compound III and pharmaceutically acceptable salts thereof is administered daily; or (ii) 150 mg, 200 mg, or 300 mg of at least one compound chosen from Compound III-d and pharmaceutically acceptable salts thereof is administered daily.

39. The method according to any one of embodiments 1, 2, 4, and 5, wherein: (i) 150 mg of at least one compound chosen from Compound III and pharmaceutically acceptable salts thereof is administered twice daily; or (ii) 150 mg of at least one compound chosen from Compound III-d and pharmaceutically acceptable salts thereof is administered once daily.

40. The method according to any one of embodiments 1, 2, 4, 5, and 32-38, wherein: (i) at least one compound chosen from Compound III and pharmaceutically acceptable salts thereof is administered as a single dose, once daily; or (ii) at least one compound chosen from Compound III-d and pharmaceutically acceptable salts thereof is administered as a single dose, once daily.

41. The method according to any one of embodiments 1, 2, 4, 5, and 32-38, wherein: (i) the dose of at least one compound chosen from Compound III and pharmaceutically acceptable salts thereof is administered in two doses daily; or (ii) the dose of at least one compound chosen from Compound III-d and pharmaceutically acceptable salts thereof is administered in two doses daily.

42. The method according to any one of embodiments 1, 3, 4, and 5, wherein 100 mg to 1,000 mg of at least one compound chosen from Compound IV and pharmaceutically acceptable salts thereof is administered daily.

43. The method according to any one of embodiments 1, 3, 4, and 5, wherein 400 mg to 1,000 mg of at least one compound chosen from Compound IV and pharmaceutically acceptable salts thereof is administered daily.

44. The method according to any one of embodiments 1, 3, 4, and 5, wherein 800 mg of at least one compound chosen from Compound IV and pharmaceutically acceptable salts thereof is administered daily.

45. The method according to any one of embodiments 1, 3, 4, 5, and 41-44, wherein 400 mg of at least one compound chosen from Compound IV and pharmaceutically acceptable salts thereof is administered twice daily.

46. The method according to any one of embodiments 1, 3, 4, 5, and 41-44, wherein the dose of at least one compound chosen from Compound IV and pharmaceutically acceptable salts thereof is administered as a single dose daily or as two doses daily.

47. The method according to embodiment 1, wherein said patient has cystic fibrosis is chosen from patients with F508del/minimal function genotypes, patients with F508del/F508del genotypes, patients with F508del/gating genotypes, and patients with F508del/residual function genotypes.

48. The method according to embodiment 1, wherein 40 mg to 600 mg of at least one compound chosen from Compound I and pharmaceutically acceptable salts thereof is administered daily.

49. The method according to embodiment 1, wherein: (i) 50 mg to 200 mg of at least one compound chosen from Compound II and pharmaceutically acceptable salts thereof is administered daily; and/or 100 mg to 225 mg of at least one compound chosen from Compound III-d and pharmaceutically acceptable salts thereof is administered daily; or (ii) 50 mg to 200 mg of at least one compound chosen from Compound II and pharmaceutically acceptable salts thereof is administered daily; and/or 150 mg to 600 mg of at least one compound chosen from Compound III and pharmaceutically acceptable salts thereof is administered daily.

50. The method according to any one of embodiments 1, 48, and 49, wherein: (i) 100 mg to 225 mg of at least one compound chosen from Compound III-d and pharmaceutically acceptable salts thereof and/or 400 mg to 1,000 mg of at least one compound chosen from Compound IV and pharmaceutically acceptable salts thereof is administered daily; (ii) 150 mg to 250 mg of at least one compound chosen from Compound III and pharmaceutically acceptable salts thereof and/or 400 mg to 1,000 mg of at least one compound chosen from Compound IV and pharmaceutically acceptable salts thereof is administered daily.

51. A method of treating cystic fibrosis comprising administering daily to a patient in need thereof a pharmaceutical composition comprising:

(A) 10 mg to 900 mg of at least one compound chosen from Compound I

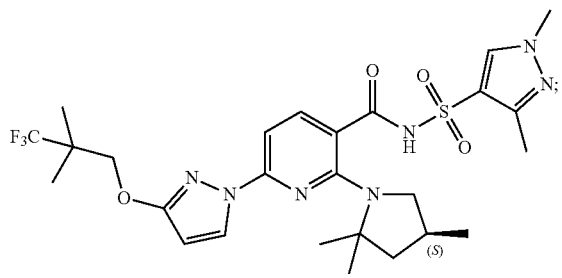

and pharmaceutically acceptable salts thereof, and (B) at least one compound chosen from: (i) Compound II:

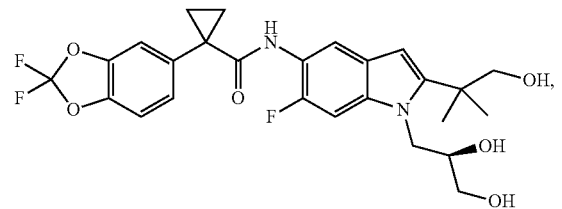 [SMILES: CC(C)(CO)c1cc2cc(NC(=O)C3(c4ccc5c(c4)OC(F)(F)O5)CC3)c(F)cc2n1C[C@@H](O)CO]

and (ii) Compound III or Compound III-d:

(Compound III)

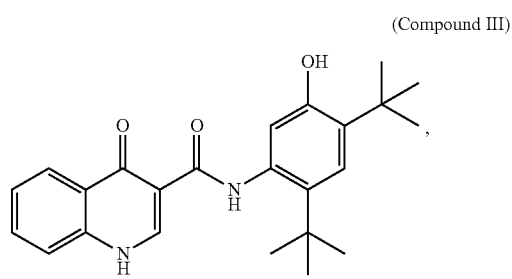

(Compuond III-d)

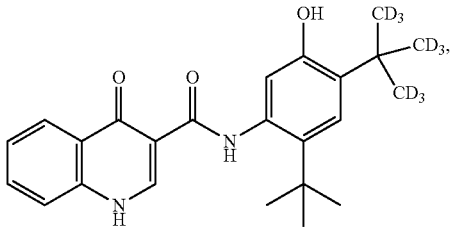

and (iii) Compound IV:

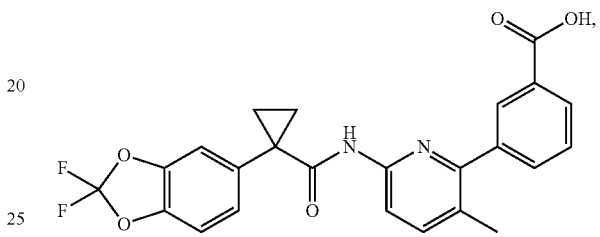

and pharmaceutically acceptable salts of any of the foregoing; and (C) a pharmaceutically acceptable carrier.

52. The method according to embodiment 51, wherein the pharmaceutical composition comprises: (i) at least one compound chosen from Compound I and pharmaceutically acceptable salts thereof, at least one compound chosen from Compound II and pharmaceutically acceptable salts thereof, and at least one compound chosen from Compound III and pharmaceutically acceptable salts thereof; or (ii) at least one compound chosen from Compound I and pharmaceutically acceptable salts thereof, at least one compound chosen from Compound II and pharmaceutically acceptable salts thereof, and at least one compound chosen from Compound III-d and pharmaceutically acceptable salts thereof.

53. The method according to embodiment 51, wherein the pharmaceutical composition comprises: at least one compound chosen from Compound I and pharmaceutically acceptable salts thereof, at least one compound chosen from Compound II and pharmaceutically acceptable salts thereof, and at least one compound chosen from Compound IV and pharmaceutically acceptable salts thereof.

54. The method according to embodiment 51, wherein: (i) the pharmaceutical composition comprises: at least one compound chosen from Compound I and pharmaceutically acceptable salts thereof, at least one compound chosen from Compound III and pharmaceutically acceptable salts thereof, and at least one compound chosen from Compound IV and pharmaceutically acceptable salts thereof, or (ii) the pharmaceutical composition comprises: at least one compound chosen from Compound I and pharmaceutically acceptable salts thereof, at least one compound chosen from Compound III-d and pharmaceutically acceptable salts thereof, and at least one compound chosen from Compound IV and pharmaceutically acceptable salts thereof.

55. The method of according to embodiment 51, wherein the pharmaceutical composition comprises: (i) at least one compound chosen from Compound I and pharmaceutically acceptable salts thereof and at least one compound chosen from Compound II and pharmaceutically acceptable salts thereof, (ii) at least one compound chosen from Compound I and pharmaceutically acceptable salts thereof and at least one compound chosen from Compound III and pharmaceutically acceptable salts thereof, (iii) at least one compound chosen from Compound I and pharmaceutically acceptable salts thereof and at least one compound chosen from Compound III-d and pharmaceutically acceptable salts thereof, or (iv) at least one compound chosen from Compound I and pharmaceutically acceptable salts thereof and at least one compound chosen from Compound IV and pharmaceutically acceptable salts thereof.

56. The method according to any one of embodiments 51-55, wherein 20 mg to 800 mg of at least one compound chosen from Compound I and pharmaceutically acceptable salts thereof is administered daily.

57. The method according to any one of embodiments 51-55, wherein 30 mg to 720 mg of at least one compound chosen from Compound I and pharmaceutically acceptable salts thereof is administered daily.

58. The method according to any one of embodiments 51-55, wherein 40 mg to 600 mg of at least one compound chosen from Compound I and pharmaceutically acceptable salts thereof is administered daily.

59. The method according to any one of embodiments 51-55, wherein 40 mg to 550 mg of at least one compound chosen from Compound I and pharmaceutically acceptable salts thereof is administered daily.

60. The method according to any one of embodiments 51-55, wherein 40 mg to 500 mg of at least one compound chosen from Compound I and pharmaceutically acceptable salts thereof is administered daily.

61. The method according to any one of embodiments 51-55, wherein 40 mg to 400 mg of at least one compound chosen from Compound I and pharmaceutically acceptable salts thereof is administered daily.

62. The method according to any one of embodiments 51-55, wherein 40 mg to 300 mg of at least one compound chosen from Compound I and pharmaceutically acceptable salts thereof is administered daily.

63. The method according to any one of embodiments 51-55, wherein 50 mg to 360 mg of at least one compound chosen from Compound I and pharmaceutically acceptable salts thereof is administered daily.

64. The method according to any one of embodiments 51-55, wherein 160 mg to 320 mg at least one compound chosen from Compound I and pharmaceutically acceptable salts thereof is administered daily.

65. The method according to any one of embodiments 51-55, wherein: (i) 240 mg to 400 mg of at least one compound chosen from Compound I and pharmaceutically acceptable salts thereof is administered daily; or (ii) 160 mg to 300 mg of at least one compound chosen from Compound I and pharmaceutically acceptable salts thereof is administered daily.

66. The method according to any one of embodiments 51-55, wherein: (i) 320 mg to 480 mg of at least one compound chosen from Compound I and pharmaceutically acceptable salts thereof is administered daily; or (ii) 160 mg to 400 mg of at least one compound chosen from Compound I and pharmaceutically acceptable salts thereof is administered daily.

67. The method according to any one of embodiments 51-55, wherein: (i) 360 mg to 640 mg of at least one compound chosen from Compound I and pharmaceutically acceptable salts thereof is administered daily; or (ii) 180 mg to 220 mg of at least one compound chosen from Compound I and pharmaceutically acceptable salts thereof is administered daily.

68. The method according to any one of embodiments 51-55, wherein 80 mg to 360 mg of at least one compound chosen from Compound I and pharmaceutically acceptable salts thereof is administered daily.

69. The method according to any one of embodiments 51-55, wherein 50 mg of at least one compound chosen from Compound I and pharmaceutically acceptable salts thereof is administered daily.

70. The method according to any one of embodiments 51-55, wherein 100 mg of at least one compound chosen from Compound I and pharmaceutically acceptable salts thereof is administered daily.

71. The method according to any one of embodiments 51-55, wherein 250 mg or 200 mg of at least one compound chosen from Compound I and pharmaceutically acceptable salts thereof is administered daily.

72. The method according to any one of embodiments 51-55, wherein 150 mg, 200 mg, 250 mg, 300 mg, 350 mg, 400 mg, 450 mg, 500 mg, 550 mg, or 600 mg of at least one compound chosen from Compound I and pharmaceutically acceptable salts thereof is administered daily.

73. The method according to any one of embodiments 51-53 and 55, wherein 25 mg to 200 mg of at least one compound chosen from Compound II and pharmaceutically acceptable salts thereof is administered daily.

74. The method according to any one of embodiments 51-53 and 55, wherein 50 mg to 150 mg of at least one compound chosen from Compound II and pharmaceutically acceptable salts thereof is administered daily.

75. The method according to any one of embodiments 51-53 and 55, wherein 75 mg to 200 mg of at least one compound chosen from Compound II and pharmaceutically acceptable salts thereof is administered daily.

76. The method according to any one of embodiments 51-53 and 55, wherein 50 mg of at least one compound chosen from Compound II and pharmaceutically acceptable salts thereof is administered daily.

77. The method according to any one of embodiments 51-53 and 55, wherein 100 mg of at least one compound chosen from Compound II and pharmaceutically acceptable salts thereof is administered daily.

78. The method according to any one of embodiments 51, 52, 54, and 55, wherein: (i) 50 mg to 600 mg of at least one compound chosen from Compound III and pharmaceutically acceptable salts thereof is administered daily; or (ii) 50 mg to 400 mg of at least one compound chosen from Compound III-d and pharmaceutically acceptable salts thereof is administered daily.

79. The method according to any one of embodiments 51, 52, 54, and 55, wherein: (i) 50 mg to 450 mg of at least one compound chosen from Compound III and pharmaceutically acceptable salts thereof is administered daily; or (ii) 50 mg to 300 mg of at least one compound chosen from Compound III-d and pharmaceutically acceptable salts thereof is administered daily.

80. The method according to any one of embodiments 51, 52, 54, and 55, wherein: (i) 100 mg to 400 mg of at least one compound chosen from Compound III and pharmaceutically acceptable salts thereof is administered daily; or (ii) 100 mg to 300 mg of at least one compound chosen from Compound III-d and pharmaceutically acceptable salts thereof is administered daily.

81. The method according to any one of embodiments 51, 52, 54, and 55, wherein: (i) 125 mg to 300 mg of at least one compound chosen from Compound III and pharmaceutically acceptable salts thereof is administered daily; or (ii) 125 mg to 300 mg of at least one compound chosen from Compound III-d and pharmaceutically acceptable salts thereof is administered daily.

82. The method according to any one of embodiments 51, 52, 54, and 55, wherein: (i) 150 mg to 300 mg of at least one compound chosen from Compound III and pharmaceutically acceptable salts thereof is administered daily; or (ii) 100 mg to 200 mg of at least one compound chosen from Compound III-d and pharmaceutically acceptable salts thereof is administered daily.

83. The method according to any one of embodiments 51, 52, 54, and 55, wherein: (i) 200 mg to 600 mg of at least one compound chosen from Compound III and pharmaceutically acceptable salts thereof is administered daily; or (ii) 125 mg to 200 mg of at least one compound chosen from Compound III-d and pharmaceutically acceptable salts thereof is administered daily.

84. The method according to any one of embodiments 51, 52, 54, and 55, wherein: (i) 300 mg or 600 mg of at least one compound chosen from Compound III and pharmaceutically acceptable salts thereof is administered daily; or (ii) 150 mg, 200 mg, or 300 mg of at least one compound chosen from Compound III-d and pharmaceutically acceptable salts thereof is administered daily.

85. The method according to any one of embodiments 51, 52, 54, and 55, wherein: (i) 150 mg of at least one compound chosen from Compound III and pharmaceutically acceptable salts thereof is administered twice daily; or 150 mg of at least one compound chosen from Compound III-d and pharmaceutically acceptable salts thereof is administered once daily.

86. The method according to any one of embodiments 51, 53, 54, and 55, wherein 100 mg to 1,000 mg of at least one compound chosen from Compound IV and pharmaceutically acceptable salts thereof is administered daily.

87. The method according to any one of embodiments 51, 53, 54, and 55, wherein 400 mg to 1,000 mg of at least one compound chosen from Compound IV and pharmaceutically acceptable salts thereof is administered daily.

88. The method according to any one of embodiments 51, 53, 54, and 55, wherein 800 mg of at least one compound chosen from Compound IV and pharmaceutically acceptable salts thereof is administered daily, or 400 mg of at least one compound chosen from Compound IV and pharmaceutically acceptable salts thereof is administered twice daily.

89. The method according to embodiment 51, wherein said patient has cystic fibrosis is chosen from patients with F508del/minimal function genotypes, patients with F508del/F508del genotypes, patients with F508del/gating genotypes, and patients with F508del/residual function genotypes.

90. The method according to embodiment 51, wherein said pharmaceutical composition comprises 40 mg to 600 mg of at least one compound chosen from Compound I and pharmaceutically acceptable salts thereof and is administered daily.

91. The method according to embodiment 90, further wherein: (i) 50 mg to 200 mg of at least one compound chosen from Compound II and pharmaceutically acceptable salts thereof is administered daily and/or 150 mg to 600 mg of at least one compound chosen from Compound III and pharmaceutically acceptable salts thereof is administered daily; or (ii) 50 mg to 200 mg of at least one compound chosen from Compound II and pharmaceutically acceptable salts thereof is administered daily and/or 100 mg to 225 mg of at least one compound chosen from Compound III-d and pharmaceutically acceptable salts thereof is administered daily.

92. The method according to any one of embodiments 51, 90, and 91, wherein: (i) 150 mg to 600 mg of at least one compound chosen from Compound III and pharmaceutically acceptable salts thereof and/or 400 mg to 1,000 mg of at least one compound chosen from Compound IV and pharmaceutically acceptable salts thereof is administered daily; or (ii) 100 mg to 225 mg of at least one compound chosen from Compound III-d and pharmaceutically acceptable salts thereof and/or 400 mg to 1,000 mg of at least one compound chosen from Compound IV and pharmaceutically acceptable salts thereof is administered daily.

93. A method of treating cystic fibrosis comprising administering to a patient in need thereof:

(A) a first pharmaceutical composition comprising 10 mg to 900 mg at least one compound chosen from Compound I

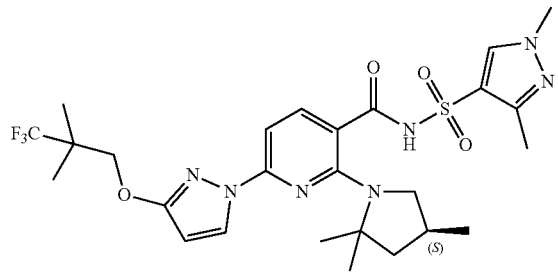

and pharmaceutically acceptable salts thereof, and a pharmaceutically acceptable carrier, wherein said first pharmaceutical composition is administered daily; and (B) a second pharmaceutical composition comprising at least one compound chosen from (i) Compound II:

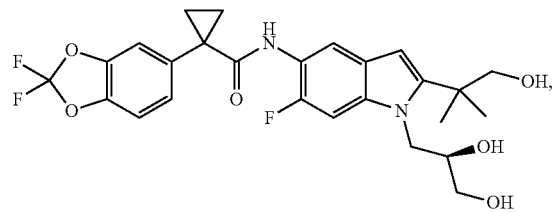 [SMILES: CC(C)(CO)c1cc2cc(NC(=O)C3(c4ccc5c(c4)OC(F)(F)O5)CC3)c(F)cc2n1C[C@@H](O)CO]

and (ii) Compound III or Compound III-d:

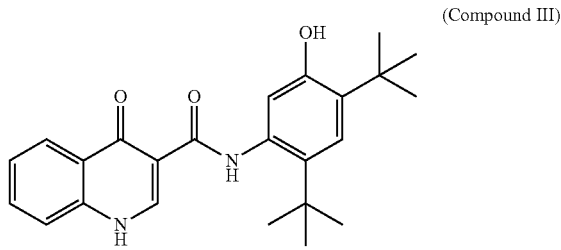

(Compound III)

-continued (Compuond III-d)

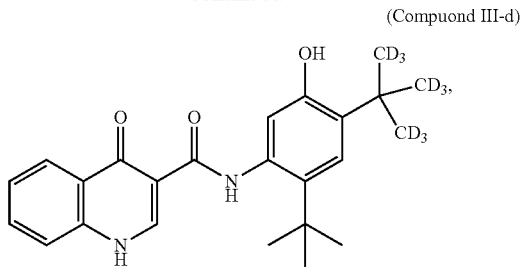

and (iii) Compound IV:

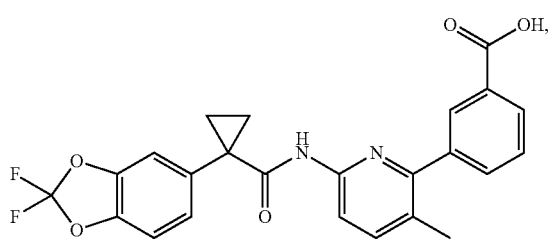 [SMILES: Cc1ccc(NC(=O)C2(c3ccc4c(c3)OC(F)(F)O4)CC2)nc1-c1cccc(C(=O)O)c1]

and pharmaceutically acceptable salts of any of the foregoing, and a pharmaceutically acceptable carrier.

94. The method according to embodiment 93, wherein: (i) the first pharmaceutical composition comprises at least one compound chosen from Compound I and pharmaceutically acceptable salts thereof, and the second pharmaceutical composition comprises at least one compound chosen from Compound II and pharmaceutically acceptable salts thereof, and at least one compound chosen from Compound III and pharmaceutically acceptable salts thereof, or (ii) the first pharmaceutical composition comprises at least one compound chosen from Compound I and pharmaceutically acceptable salts thereof, and the second pharmaceutical composition comprises at least one compound chosen from Compound II and pharmaceutically acceptable salts thereof, and at least one compound chosen from Compound III-d and pharmaceutically acceptable salts thereof.

95. The method according to embodiment 93, wherein the first pharmaceutical composition comprises: at least one compound chosen from Compound I and pharmaceutically acceptable salts thereof, and the second pharmaceutical composition comprises at least one compound chosen from Compound II and pharmaceutically acceptable salts thereof, and at least one compound chosen from Compound IV and pharmaceutically acceptable salts thereof.

96. The method according to embodiment 93, wherein: (i) the first pharmaceutical composition comprises: at least one compound chosen from Compound I and pharmaceutically acceptable salts thereof, and the second pharmaceutical composition comprises: at least one compound chosen from Compound III and pharmaceutically acceptable salts thereof and at least one compound chosen from Compound IV and pharmaceutically acceptable salts thereof, or (ii) the first pharmaceutical composition comprises: at least one compound chosen from Compound I and pharmaceutically acceptable salts thereof, and the second pharmaceutical composition comprises: at least one compound chosen from Compound III-d and pharmaceutically acceptable salts thereof and at least one compound chosen from Compound IV and pharmaceutically acceptable salts thereof.

97. The method of according to embodiment 93, wherein the first pharmaceutical composition comprises: at least one compound chosen from Compound I and pharmaceutically acceptable salts thereof, and the second pharmaceutical composition comprises: (i) at least one compound chosen from Compound II and pharmaceutically acceptable salts thereof and at least one compound chosen from Compound III and pharmaceutically acceptable salts thereof, (ii) at least one compound chosen from Compound II and pharmaceutically acceptable salts thereof and at least one compound chosen from Compound III-d and pharmaceutically acceptable salts thereof, or (ii) at least one compound chosen from Compound II and pharmaceutically acceptable salts thereof and at least one compound chosen from Compound IV and pharmaceutically acceptable salts thereof.

98. The method according to any one of embodiments 93-97, wherein 20 mg to 800 mg of at least one compound chosen from Compound I and pharmaceutically acceptable salts thereof is administered daily.

99. The method according to any one of embodiments 93-97, wherein 30 mg to 720 mg of at least one compound chosen from Compound I and pharmaceutically acceptable salts thereof is administered daily.

100. The method according to any one of embodiments 93-97, wherein 40 mg to 600 mg of at least one compound chosen from Compound I and pharmaceutically acceptable salts thereof is administered daily.

101. The method according to any one of embodiments 93-97, wherein 40 mg to 600 mg or 40 mg to 550 mg of at least one compound chosen from Compound I and pharmaceutically acceptable salts thereof is administered daily.

102. The method according to any one of embodiments 93-97, wherein 40 mg to 500 mg of at least one compound chosen from Compound I and pharmaceutically acceptable salts thereof is administered daily.

103. The method according to any one of embodiments 93-97, wherein 40 mg to 400 mg of at least one compound chosen from Compound I and pharmaceutically acceptable salts thereof is administered daily.

104. The method according to any one of embodiments 93-97, wherein 40 mg to 300 mg of at least one compound chosen from Compound I and pharmaceutically acceptable salts thereof is administered daily.

105. The method according to any one of embodiments 93-97, wherein 50 mg to 360 mg of at least one compound chosen from Compound I and pharmaceutically acceptable salts thereof is administered daily.

106. The method according to any one of embodiments 93-97, wherein 160 mg to 320 mg of at least one compound chosen from Compound I and pharmaceutically acceptable salts thereof is administered daily.

107. The method according to any one of embodiments 93-97, wherein 240 mg to 400 mg or 160 mg to 300 mg of at least one compound chosen from Compound I and pharmaceutically acceptable salts thereof is administered daily.

108. The method according to any one of embodiments 93-97, wherein 320 mg to 480 mg or 160 mg to 400 mg of at least one compound chosen from Compound I and pharmaceutically acceptable salts thereof is administered daily.

109. The method according to any one of embodiments 93-97, wherein 360 mg to 640 mg or 180 mg to 220 mg of at least one compound chosen from Compound I and pharmaceutically acceptable salts thereof is administered daily.

110. The method according to any one of embodiments 93-97, wherein 80 mg to 360 mg of at least one compound 111. The method according to any one of embodiments 93-97, wherein 50 mg of at least one compound chosen from Compound I and pharmaceutically acceptable salts thereof is administered daily.

112. The method according to any one of embodiments 93-97, wherein 100 mg of at least one compound chosen from Compound I and pharmaceutically acceptable salts thereof is administered daily.

113. The method according to any one of embodiments 93-97, wherein 250 mg or 200 mg of at least one compound chosen from Compound I and pharmaceutically acceptable salts thereof is administered daily.

114. The method according to any one of embodiments 93-97, wherein 150 mg, 200 mg, 250 mg, 300 mg, 350 mg, 400 mg, 450 mg, 500 mg, 550 mg, or 600 mg of at least one compound chosen from Compound I and pharmaceutically acceptable salts thereof is administered daily.

115. The method according to any one of embodiments 93-114, wherein at least one compound chosen from Compound I and pharmaceutically acceptable salts thereof is administered as a single dose, once daily.

116. The method according to any one of embodiments 93-114, wherein at least one compound chosen from Compound I and pharmaceutically acceptable salts thereof is administered in two doses daily.

117. The method according to any one of embodiments 93-95 and 97, wherein 25 mg to 200 mg of at least one compound chosen from Compound II and pharmaceutically acceptable salts thereof is administered daily.

118. The method according to any one of embodiments 93-95 and 97, wherein 50 mg to 150 mg of at least one compound chosen from Compound II and pharmaceutically acceptable salts thereof is administered daily.

119. The method according to any one of embodiments 93-95 and 97, wherein 75 mg to 200 mg of at least one compound chosen from Compound II and pharmaceutically acceptable salts thereof is administered daily.

120. The method according to any one of embodiments 93-95 and 97, wherein 50 mg of at least one compound chosen from Compound II and pharmaceutically acceptable salts thereof is administered daily.

121. The method according to any one of embodiments 93-95 and 97, wherein 100 mg of at least one compound chosen from Compound II and pharmaceutically acceptable salts thereof is administered daily.

122. The method according to any one of embodiments 93-95, 97, and 117-121, wherein at least one compound chosen from Compound II and pharmaceutically acceptable salts thereof is administered as a single dose, once daily.

123. The method according to any one of embodiments 93-95, 97, and 117-121, wherein at least one compound chosen from Compound II and pharmaceutically acceptable salts thereof is administered in two doses daily.

124. The method according to any one of embodiments 93, 94, 96, and 97, wherein: (i) 50 mg to 600 mg of at least one compound chosen from Compound III and pharmaceutically acceptable salts thereof is administered daily; or (ii) 50 mg to 400 mg of at least one compound chosen from Compound III-d and pharmaceutically acceptable salts thereof is administered daily.

125. The method according to any one of embodiments 93, 94, 96, and 97, wherein: (i) 50 mg to 450 mg of at least one compound chosen from Compound III and pharmaceutically acceptable salts thereof is administered daily; or (ii) 50 mg to 300 mg of at least one compound chosen from Compound III-d and pharmaceutically acceptable salts thereof is administered daily.

126. The method according to any one of embodiments 93, 94, 96, and 97, wherein: (i) 100 mg to 400 mg of at least one compound chosen from Compound III and pharmaceutically acceptable salts thereof is administered daily; or (ii) 100 mg to 300 mg of at least one compound chosen from Compound III-d and pharmaceutically acceptable salts thereof is administered daily.

127. The method according to any one of embodiments 93, 94, 96, and 97, wherein: (i) 125 mg to 300 mg of at least one compound chosen from Compound III and pharmaceutically acceptable salts thereof is administered daily; or (ii) 125 mg to 300 mg of at least one compound chosen from Compound III-d and pharmaceutically acceptable salts thereof is administered daily.

128. The method according to any one of embodiments 93, 94, 96, and 97, wherein: (i) 150 mg to 300 mg of at least one compound chosen from Compound III and pharmaceutically acceptable salts thereof is administered daily; or (ii) 100 mg to 200 mg of at least one compound chosen from Compound III-d and pharmaceutically acceptable salts thereof is administered daily.

129. The method according to any one of embodiments 93, 94, 96, and 97, wherein: (i) 200 mg to 600 mg of at least one compound chosen from Compound III and pharmaceutically acceptable salts thereof is administered daily; or (ii) 125 mg to 200 mg of at least one compound chosen from Compound III-d and pharmaceutically acceptable salts thereof is administered daily.

130. The method according to any one of embodiments 93, 94, 96, and 97, wherein: (i) 300 mg or 600 mg of at least one compound chosen from Compound III and pharmaceutically acceptable salts thereof is administered daily; or (ii) 150 mg, 200 mg, or 300 mg of at least one compound chosen from Compound III-d and pharmaceutically acceptable salts thereof per dosing is administered once daily.

131. The method according to any one of embodiments 93, 94, 96, and 97, wherein: (i) 150 mg of at least one compound chosen from Compound III and pharmaceutically acceptable salts thereof per dosing is administered twice daily; or (ii) 150 mg of at least one compound chosen from Compound III-d and pharmaceutically acceptable salts thereof per dosing is administered once daily.

132. The method according to any one of embodiments 93, 94, 96, 97, and 124-130, wherein: (i) at least one compound chosen from Compound III and pharmaceutically acceptable salts thereof is administered as a single dose, once daily; or (ii) at least one compound chosen from Compound III-d and pharmaceutically acceptable salts thereof is administered as a single dose, once daily.

133. The method according to any one of embodiments 93, 94, 96, 97, and 124-130, wherein: (i) the dose of at least one compound chosen from Compound III and pharmaceutically acceptable salts thereof is administered in twice daily; or (ii) the dose of at least one compound chosen from Compound III-d and pharmaceutically acceptable salts thereof is administered in twice daily.

134. The method according to any one of embodiments 93 and 95-97, wherein 100 mg to 1,000 mg of at least one compound chosen from Compound IV and pharmaceutically acceptable salts thereof per dosing is administered daily.

135. The method according to any one of embodiments 93 and 95-97, wherein 400 mg to 1,000 mg of at least one compound chosen from Compound IV and pharmaceutically acceptable salts thereof is administered daily.

136. The method according to any one of embodiments 93 and 95-97, wherein 400 mg to 800 mg of at least one compound chosen from Compound IV and pharmaceutically acceptable salts thereof is administered daily.

137. The method according to any one of embodiments 93, 95-97, and 133-136, wherein 800 mg of at least one compound chosen from Compound IV and pharmaceutically acceptable salts thereof per dosing is administered once daily.

138. The method according to any one of embodiments 93, 95-97, and 133-136, wherein 400 mg of at least one compound chosen from Compound IV and pharmaceutically acceptable salts thereof per dosing is administered twice daily.

139. The method according to embodiment 93, wherein said patient has cystic fibrosis is chosen from patients with F508del/minimal function genotypes, patients with F508del/F508del genotypes, patients with F508del/gating genotypes, and patients with F508del/residual function genotypes.

140. The method according to embodiment 93, wherein said first pharmaceutical composition comprises 50 mg to 600 mg of at least one compound chosen from Compound I and pharmaceutically acceptable salts thereof and is administered daily.

141. The method according to embodiment 93, wherein: (i) 50 to 200 mg of at least one compound chosen from Compound II and pharmaceutically acceptable salts thereof is administered daily and/or 150 mg to 600 mg of at least one compound chosen from Compound III and pharmaceutically acceptable salts thereof is administered daily; or (ii) 50 to 200 mg of at least one compound chosen from Compound II and pharmaceutically acceptable salts thereof is administered daily and/or 100 mg to 225 mg of at least one compound chosen from Compound III-d and pharmaceutically acceptable salts thereof is administered daily.

142. The method according to any one of embodiments 93, 140, and 141, wherein: (i) 150 mg to 600 mg of at least one compound chosen from Compound III and pharmaceutically acceptable salts thereof, and/or 400 mg to 1,000 mg of at least one compound chosen from Compound IV and pharmaceutically acceptable salts thereof is administered daily; or (ii) 100 mg to 225 mg of at least one compound chosen from Compound III-d and pharmaceutically acceptable salts thereof, and/or 400 mg to 1,000 mg of at least one compound chosen from Compound IV and pharmaceutically acceptable salts thereof is administered daily.

143. The method according to any one of embodiments 93-142, wherein said second pharmaceutical composition is administered prior to, subsequent to, or concurrently with said first pharmaceutical composition.

144. The method according to any one of embodiments 93-143, further comprising administering to said patient a third pharmaceutical composition, said composition comprising: (i) at least one compound chosen from Compound II, Compound III, Compound IV, and pharmaceutically acceptable salts thereof; or (ii) at least one compound chosen from Compound II, Compound III-d, Compound IV, and pharmaceutically acceptable salts thereof.

145. The method according to embodiment 144, wherein said third pharmaceutical composition is administered once daily.

146. The method according to any one of embodiments 1, 51, and 93, comprising administering to said patient Compound I.

147. The method according to any one of embodiments 1, 51, and 93, comprising administering to said patient a pharmaceutically acceptable salt of Compound I.

148. The method according to any one of embodiments 1, 51, and 93, comprising administering to said patient Compound II.

149. The method according to any one of embodiments 1, 51, and 93, comprising administering to said patient a pharmaceutically acceptable salt of Compound II.

150. The method according to any one of embodiments 1, 51, and 93, comprising administering to said patient Compound III or Compound III-d.

151. The method according to any one of embodiments 1, 51, and 93, comprising administering to said patient a pharmaceutically acceptable salt of Compound III or a pharmaceutically acceptable salt of Compound III-d.

152. The method according to any one of embodiments 1, 51, and 93, comprising administering to said patient Compound IV.

153. The method according to any one of embodiments 1, 51, and 93, comprising administering to said patient a pharmaceutically acceptable salt of Compound IV.

154. The method according to any one of embodiments 1, 51, and 93, comprising administering to said patient: a pharmaceutically acceptable salt of Compound I, Compound II, and Compound III-d.

155. The method according to any one of embodiments 1, 51, and 93, comprising administering to said patient: (i) Compound I, Compound II, and Compound III; or (ii) Compound I, Compound II, and Compound III-d.

156. The method according to any one of embodiments 1, 51, and 93, comprising administering to said patient: (i) Compound I, and Compound III; or (ii) Compound I, and Compound III-d.

157. The method according to any one of embodiments 1, 51, and 93, comprising administering to said patient: (i) a pharmaceutically acceptable salt of Compound I, and Compound III; or (ii) a pharmaceutically acceptable salt of Compound I, and Compound III-d.

158. The method of any one of embodiments 47, 89, or 139, wherein the patient with a F508del/minimal function genotype has a minimal function mutation selected from:

| Mutation | | | | |
|---|---|---|---|---|
| S4X | C276X | G542X | R792X | E1104X |
| G27X | Q290X | G550X | E822X | R1158X |
| Q39X | G330X | Q552X | W846X | R1162X |
| W57X | W401X | R553X | Y849X | S1196X |
| E60X | Q414X | E585X | R851X | W1204X |
| R75X | S434X | G673X | Q890X | L1254X |
| E92X | S466X | Q685X | S912X | S1255X |
| Q98X | S489X | R709X | Y913X | W1282X |
| Y122X | Q493X | K710X | W1089X | Q1313X |
| E193X | W496X | L732X | Y1092X | E1371X |
| L218X | C524X | R764X | W1098X | Q1382X |

-continued

| Mutation | | | | |
|---|---|---|---|---|
| Q220X | Q525X | R785X | R1102X | Q1411X |
| 185 + 1G→T | 711 + 5G→A | 1717 − 8G→A | 2622 + 1G→A | 3121 − 1G→A |
| 296 + 1G→A | 712 − 1G→T | 1717 − 1G→A | 2790 − 1G→C | 3500 − 2A→G |
| 405 + 1G→A | 1248 + 1G→A | 1811 + 1G→C | 3040G→C | 3600 + 2insT |
| 405 + 3A→C | 1249 − 1G→A | 1811 + 1.6 kbA→G | (G970R) | 3850 − 1G→A |
| 406 − 1G→A | 1341 + 1G→A | 1812 − 1G→A | 3120G→A | 4005 + 1G→A |
| 621 + 1G→T | 1525 − 2A→G | 1898 + 1G→A | 3120 + 1G→A | 4374 + 1G→T |
| 711 + 1G→T | 1525 − 1G→A | 1898 + 1G→C | 3121 − 2A→G | |
| 182delT | 1119delA | 1782delA | 2732insA | 3876delA |
| 306insA | 1138insG | 1824delA | 2869insG | 3878delG |
| 365-366insT | 1154insTC | 2043delG | 2896insAG | 3905insT |
| 394delTT | 1161delC | 2143delT | 2942insT | 4016insT |
| 442delA | 1213delT | 2183AA→G | 2957delT | 4021dupT |
| 444delA | 1259insA | 2184delA | 3007delG | 4040delA |
| 457TAT→G | 1288insTA | 2184insA | 3028delA | 4279insA |
| 541delC | 147delA | 2307insA | 3171delC | 4326delTC |
| 574delA | 1497delGG | 2347delG | 3659delC | |
| 663delT | 1548delG | 2585delT | 3737delA | |
| 935delA | 1609del CA | 2594delGT | 3791delC | |
| 1078delT | 1677delTA | 2711delT | 3821delT | |
| CFTRdele2, 3 | | 1461ins4 | | 2991del32 |
| CFTRdele22, 23 | | 1924del7 | | 3667ins4 |
| 124del23bp | | 2055del9→A | | 4010del4 |
| 852del22 | | 2105-2117del13insAGAAA | | 4209TGTT→AA |
| 991del5 | | 2721del11 | | |
| A46D | V520F | Y569D | | N1303K. |
| G85E | A559T | L1065P | | |
| R347P | R560T | R1066C | | |
| L467P | R560S | L1077F | | |
| I507del | A561E | M1101K | | |

159. The method of any one of embodiments 47, 89, or 139, wherein the patient with a F508del/gating genotype has a gating mutation selected from G178R, S549N, S549R, G551D, G551S, G1244E, S1251N, S1255P, and G1349D.

160. The method of any one of embodiments 47, 89, or 139, wherein the patient with a F508dell residual function genotype has a residual function mutation selected from 2789+5G→A, 3849+10kbC→T, 3272-26A→G, 711+3A→G, E56K, P67L, R74W, D110E, D110H, R117C, L206W, R347H, R352Q, A455E, D579G, E831X, S945L, S977F, F1052V, R1070W, F1074L, D1152H, D1270N, E193K, K1060T, R117H, S1235R, 11027T, R668C, G576A, M470V, L997F, R75Q, R1070Q, R31C, D614G, G1069R, R1162L, E56K, A1067T, E193K, and K1060T.

161. The method of embodiment 51 or 93, wherein the pharmaceutically acceptable carrier is HPMCAS-FIG.

162. The method according to any one of embodiments 1-5, 25-47, 49, 50, 51-55, 73-89, 91, 92, 93-97, 117-139, and 140-161, wherein 20 mg, 50 mg, 60 mg, 100 mg, 120 mg, 200 mg, 240 mg, 250 mg daily, 300 mg, 350 mg daily, 400 mg, 450 mg, 480 mg, 500 mg, 550 mg, 600 mg, or 800 mg of at least one compound chosen from Compound I and pharmaceutically acceptable salts thereof is administered daily.

163. The method according to any one of embodiments 1, 47, 51, 89, 93, 139, and 158-161, wherein said patient is administered: (i) at least one compound chosen from Compound I and pharmaceutically acceptable salts thereof, at least one compound chosen from Compound II and pharmaceutically acceptable salts thereof, and at least one compound chosen from Compound III and pharmaceutically acceptable salts thereof, and wherein 50 mg to 600 mg of at least one compound chosen from Compound I and pharmaceutically acceptable salts thereof is administered daily; 50 to 200 mg of at least one compound chosen from Compound II and pharmaceutically acceptable salts thereof is administered daily; and 150 mg to 600 mg of Compound III is administered daily; or (ii) at least one compound chosen from Compound I and pharmaceutically acceptable salts thereof, at least one compound chosen from Compound II and pharmaceutically acceptable salts thereof, and at least one compound chosen from Compound III-d and pharmaceutically acceptable salts thereof, and wherein 50 mg to 600 mg of at least one compound chosen from Compound I and pharmaceutically acceptable salts thereof is administered daily; 50 to 200 mg of at least one compound chosen from Compound II and pharmaceutically acceptable salts thereof is administered daily; and 100 mg to 200 mg of Compound III-d is administered daily.

164. The method according to any one of embodiments 1, 47, 51, 89, 93, 139, and 158-161, wherein said patient is administered: (i) at least one compound chosen from Compound I and pharmaceutically acceptable salts thereof, and at least one compound chosen from Compound III and pharmaceutically acceptable salts thereof, and wherein 50 mg to 600 mg of at least one compound chosen from Compound I and pharmaceutically acceptable salts thereof is administered daily; and 150 mg to 600 mg of Compound III is administered daily; or (ii) at least one compound chosen from Compound I and pharmaceutically acceptable salts thereof, and at least one compound chosen from Compound III-d and pharmaceutically acceptable salts thereof, and wherein 50 mg to 600 mg of at least one compound chosen from Compound I and pharmaceutically acceptable salts thereof is administered daily; and 100 mg to 200 mg of Compound III-d is administered daily.

165. The method according to any one of embodiments 1, 47, 51, 89, 93, 139, and 158-161, wherein said patient is administered: (A) (i) 50 mg to 600 mg once daily of at least one compound chosen from Compound I and pharmaceutically acceptable salts thereof, (ii) 100 mg once daily of at least one compound chosen from Compound II and pharmaceutically acceptable salts thereof or 50 mg twice daily of at least one compound chosen from Compound II and pharmaceutically acceptable salts thereof, and (iii) 150 mg once daily of at least one compound chosen from Compound III and pharmaceutically acceptable salts thereof, or (B) (i) 200 mg once daily of at least one compound chosen from Compound I and pharmaceutically acceptable salts thereof, (ii) 100 mg per dosing once daily or 50 mg per dosing twice daily of at least one compound chosen from Compound II and pharmaceutically acceptable salts thereof, and (iii) 150 mg per dosing once daily of at least one compound chosen from Compound III-d and pharmaceutically acceptable salts thereof.

166. The method according to any one of embodiments 1, 47, 51, 89, 93, 139, and 158-161, wherein said patient is administered: (i) at least one compound chosen from Compound I and pharmaceutically acceptable salts thereof, and at least one compound chosen from Compound III and pharmaceutically acceptable salts thereof, and wherein 50 mg to 600 mg of at least one compound chosen from Compound I and pharmaceutically acceptable salts thereof per dosing is administered once daily; and 150 mg or 300 mg of at least one compound chosen from Compound III and pharmaceutically acceptable salts thereof per dosing is administered twice daily; or (ii) at least one compound chosen from Compound I and pharmaceutically acceptable salts thereof, and at least one compound chosen from Compound III-d and pharmaceutically acceptable salts thereof, and wherein 50 mg to 600 mg of at least one compound chosen from Compound I and pharmaceutically acceptable salts thereof per dosing is administered once daily; and 150 mg or 300 mg of at least one compound chosen from Compound III-d and pharmaceutically acceptable salts thereof per dosing is administered once daily.

167. The method according to any one of embodiments 1, 47, 51, 89, 93, 139, and 158-161, wherein said patient is administered: (i) at least one compound chosen from Compound I and pharmaceutically acceptable salts thereof, at least one compound chosen from Compound II and pharmaceutically acceptable salts thereof, and at least one compound chosen from Compound III and pharmaceutically acceptable salts thereof, and wherein 20 mg, 60 mg, 50 mg, 100 mg, 120 mg, 150 mg, 200 mg, 240 mg, 250 mg, 300 mg, 350 mg, 400 mg, 450 mg, 480 mg, 500 mg, 550 mg, 600 mg, or 800 mg of at least one compound chosen from Compound I and pharmaceutically acceptable salts thereof per dosing is administered once daily; 100 mg of at least one compound chosen from Compound II and pharmaceutically acceptable salts thereof per dosing is administered once daily or 50 mg of at least one compound chosen from Compound II and pharmaceutically acceptable salts thereof per dosing is administered twice daily; and 150 mg or 300 mg of at least one compound chosen from Compound III and pharmaceutically acceptable salts thereof per dosing is administered twice daily; or (ii) at least one compound chosen from Compound I and pharmaceutically acceptable salts thereof, at least one compound chosen from Compound II and pharmaceutically acceptable salts thereof, and at least one compound chosen from Compound III-d and pharmaceutically acceptable salts thereof, and wherein 20 mg, 60 mg, 50 mg, 100 mg, 120 mg, 150 mg, 200 mg, 240 mg, 250 mg, 300 mg, 350 mg, 400 mg, 450 mg, 480 mg, 500 mg, 550 mg, 600 mg, or 800 mg of at least one compound chosen from Compound I and pharmaceutically acceptable salts thereof is administered per dosing once daily; 100 mg of at least one compound chosen from Compound II and pharmaceutically acceptable salts thereof per dosing is administered once daily or 50 mg of at least one compound chosen from Compound II and pharmaceutically acceptable salts thereof per dosing is administered twice daily; and 150 mg of at least one compound chosen from Compound III-d and pharmaceutically acceptable salts thereof per dosing is administered once daily.

168. The method according to any one of embodiments 1, 47, 51, 89, 93, 139, and 158-161, wherein said patient is administered: (i) at least one compound chosen from Compound I and pharmaceutically acceptable salts thereof, and at least one compound chosen from Compound III and pharmaceutically acceptable salts thereof, and wherein 20 mg, 60 mg, 50 mg, 100 mg, 120 mg, 150 mg, 200 mg, 240 mg, 250 mg, 300 mg, 350 mg, 400 mg, 450 mg, 480 mg, 500 mg, 550 mg, 600 mg, or 800 mg of at least one compound chosen from Compound I and pharmaceutically acceptable salts thereof per dosing is administered once daily; and 150 mg or 300 mg of at least one compound chosen from Compound III and pharmaceutically acceptable salts thereof per dosing is administered twice daily; or (ii) at least one compound chosen from Compound I and pharmaceutically acceptable salts thereof, and at least one compound chosen from Compound III-d and pharmaceutically acceptable salts thereof, and wherein 20 mg, 60 mg, 50 mg, 100 mg, 120 mg, 150 mg, 200 mg, 240 mg, 250 mg, 300 mg, 350 mg, 400 mg, 450 mg, 480 mg, 500 mg, 550 mg, 600 mg, or 800 mg of at least one compound chosen from Compound I and pharmaceutically acceptable salts thereof per dosing is administered once daily; and 150 mg of at least one compound chosen from Compound III-d and pharmaceutically acceptable salts thereof per dosing is administered once daily.

169. The method according to any one of embodiments 1, 47, 51, 89, 93, 139, and 158-161, wherein said patient is administered: (i) at least one compound chosen from Compound I and pharmaceutically acceptable salts thereof, at least one compound chosen from Compound II and pharmaceutically acceptable salts thereof, and at least one compound chosen from Compound III and pharmaceutically acceptable salts thereof, wherein 50 mg, 80 mg, 100 mg, 150 mg, 160 mg, 200 mg, 240 mg, 250 mg, 300 mg, or 320 mg of at least one compound chosen from Compound I and pharmaceutically acceptable salts thereof per dosing is administered twice daily; 100 mg of at least one compound chosen from Compound II and pharmaceutically acceptable salts thereof per dosing is administered once daily or 50 mg of at least one compound chosen from Compound II and pharmaceutically acceptable salts thereof per dosing is administered twice daily; and 150 mg or 300 mg of Compound III per dosing is administered twice daily; or (ii) at least one compound chosen from Compound I and pharmaceutically acceptable salts thereof, at least one compound chosen from Compound II and pharmaceutically acceptable salts thereof, and at least one compound chosen from Compound III-d and pharmaceutically acceptable salts thereof, wherein 50 mg, 80 mg, 100 mg, 150 mg, 160 mg, 200 mg, 240 mg, 250 mg, 300 mg, or 320 mg of at least one compound chosen from Compound I and pharmaceutically acceptable salts thereof per dosing is administered twice daily; 100 mg of at least one compound chosen from Compound II and pharmaceutically acceptable salts thereof per dosing is administered once daily or 50 mg of at least one compound chosen from Compound II and pharmaceutically acceptable salts thereof per dosing is administered twice daily; and 150 mg of Compound III-d per dosing is administered once daily.

170. The method according to any one of embodiments 1, 47, 51, 89, 93, 139, and 158-161, wherein said patient is administered: (i) at least one compound chosen from Compound I and pharmaceutically acceptable salts thereof, and at least one compound chosen from Compound III and pharmaceutically acceptable salts thereof, wherein 50 mg, 80 mg, 100 mg, 150 mg, 160 mg, 200 mg, 240 mg, 250 mg, 300 mg, or 320 mg of at least one compound chosen from Compound I and pharmaceutically acceptable salts thereof per dosing is administered twice daily; and 150 mg or 300 mg of Compound III is administered twice daily; or (ii) at least one compound chosen from Compound I and pharmaceutically acceptable salts thereof, and at least one compound chosen from Compound III-d and pharmaceutically acceptable salts thereof, wherein 50 mg, 80 mg, 100 mg, 150 mg, 160 mg, 200 mg, 240 mg, 250 mg, 300 mg, or 320 mg of at least one compound chosen from Compound I and pharmaceutically acceptable salts thereof per dosing is administered twice daily; and 150 mg of Compound III-d per dosing is administered once daily.

171. The method according to any one of embodiments 162-170, comprising administering to said patient Compound I.

172. The method according to any one of embodiments 162-170, comprising administering to said patient a pharmaceutically acceptable salt of Compound I.

173. The method according to embodiment 171 or 172, comprising administering said patient Compound III-d.

174. The method according to any one of embodiments 163, 165, 167, 169, comprising administering said patient Compound II.

175. The method according to any one of embodiments 163, 165, 167, 169, comprising administering to said patient: (i) Compound I, Compound II, and Compound III; or (ii) Compound I, Compound II, and Compound III-d.

176. The method according to any one of embodiments 1-175, further comprising administering at least one additional active pharmaceutical ingredient.

177. The method according to any one of embodiments 1-175, wherein at least one of Compound I, Compound II, and Compound III is isotope-labelled.

178. The method according to embodiment 177, wherein at least one of the hydrogen atoms in at least one of Compound I, Compound II, Compound III, and Compound III-d is replaced by deuterium.

179. The method according to any one of embodiments 1-50, wherein said at least one compound chosen from Compound I and pharmaceutically acceptable salts thereof is comprised in a first pharmaceutical composition, said at least one compound chosen from Compound II and pharmaceutically acceptable salts thereof is comprised in a second pharmaceutical composition, and said at least one compound chosen from Compound III and pharmaceutically acceptable salts thereof or form Compound III-d and pharmaceutically acceptable salts thereof is comprised in a third pharmaceutical composition.

180. The method according to any one of embodiments 1-50, wherein: (i) said at least one compound chosen from Compound I and pharmaceutically acceptable salts thereof is comprised in a first pharmaceutical composition, and said at least one compound chosen from Compound II and pharmaceutically acceptable salts thereof and said at least one compound chosen from Compound III and pharmaceutically acceptable salts thereof are comprised in a second pharmaceutical composition; or (ii) said at least one compound chosen from Compound I and pharmaceutically acceptable salts thereof is comprised in a first pharmaceutical composition, and said at least one compound chosen from Compound II and pharmaceutically acceptable salts thereof and said at least one compound chosen from Compound III-d and pharmaceutically acceptable salts thereof are comprised in a second pharmaceutical composition.

181. The method according to embodiment 180, wherein: (i) said second pharmaceutical composition comprises one half of the daily dose of said at least one compound chosen from Compound III and pharmaceutically acceptable salts thereof, and the other half of the daily dose of said at least one compound chosen from Compound III and pharmaceutically acceptable salts thereof is administered to said patient in a third pharmaceutical composition; or (ii) said second pharmaceutical composition comprises one half of the daily dose of said at least one compound chosen from Compound III-d and pharmaceutically acceptable salts thereof, and the other half of the daily dose of said at least one compound chosen from Compound III-d and pharmaceutically acceptable salts thereof is administered to said patient in a third pharmaceutical composition.

182. The method according to any one of embodiments 1-50, wherein: (i) said at least one compound chosen from Compound I and pharmaceutically acceptable salts thereof is comprised in a first pharmaceutical composition, said at least one compound chosen from Compound II and pharmaceutically acceptable salts thereof is comprised in a second pharmaceutical composition, and said at least one compound chosen from Compound III and pharmaceutically acceptable salts thereof is comprised in the first pharmaceutical composition; or (ii) said at least one compound chosen from Compound I and pharmaceutically acceptable salts thereof is comprised in a first pharmaceutical composition, said at least one compound chosen from Compound II and pharmaceutically acceptable salts thereof is comprised in a second pharmaceutical composition, and said at least one compound chosen from Compound III-d and pharmaceutically acceptable salts thereof is comprised in the first pharmaceutical composition.

183. The method according to embodiment 182, wherein the first pharmaceutical composition is administered to the patient twice daily.

184. The method according to any one of embodiments 1-50 and 51-178, wherein: (i) Compound I, Compound II, and Compound III are administered to said patient, and wherein Compound I, Compound II, and Compound III are comprised in a first pharmaceutical composition; or (ii) Compound I, Compound II, and Compound III-d are administered to said patient, and wherein Compound I, Compound II, and Compound III-d are comprised in a first pharmaceutical composition.

185. The method according to embodiment 184, wherein the first pharmaceutical composition is administered to the patient twice daily.

186. The method according to any one of embodiments 1-50 and 51-178, wherein: (i) Compound I, Compound II, and Compound III are administered to said patient, and wherein Compound I is comprised in a first pharmaceutical composition, Compound II is comprised in a second pharmaceutical composition, and Compound III is comprised in a third pharmaceutical composition; or (ii) Compound I, Compound II, and Compound III-d are administered to said patient, and wherein Compound I is comprised in a first pharmaceutical composition, Compound II is comprised in a second pharmaceutical composition, and Compound III-d is comprised in a third pharmaceutical composition.

187. The method according to any one of embodiments 1-50 and 51-178, wherein: (i) Compound I, Compound II, and Compound III are administered to said patient, and wherein Compound I is comprised in a first pharmaceutical composition, and Compound II and Compound III are comprised in a second pharmaceutical composition; or (ii) Compound I, Compound II, and Compound III-d are administered to said patient, and wherein Compound I is comprised in a first pharmaceutical composition, and Compound II and Compound III-d are comprised in a second pharmaceutical composition.

188. The method according to embodiment 187, wherein: (i) said second pharmaceutical composition comprises one half of the daily dose of Compound III, and the other half of the daily dose of Compound III is administered to said patient in a third pharmaceutical composition; or (ii) said second pharmaceutical composition comprises one half of the daily dose of Compound III-d, and the other half of the daily dose of Compound III-d is administered to said patient in a third pharmaceutical composition.

189. The method according to any one of embodiments 1-50 and 51-178, wherein: (i) Compound I, Compound II, and Compound III are administered to said patient, and wherein Compound I is comprised in a first pharmaceutical composition, Compound II is comprised in a second pharmaceutical composition, and Compound III is comprised in the first pharmaceutical composition; or (ii) Compound I, Compound II, and Compound III-d are administered to said patient, and wherein Compound I is comprised in a first pharmaceutical composition, Compound II is comprised in a second pharmaceutical composition, and Compound III-d is comprised in the first pharmaceutical composition.

190. The method according to embodiment 189, wherein the first pharmaceutical composition is administered to the patient twice daily.

191. The method according to any one of embodiments 1-50 and 51-178, wherein: (i) Compound I, Compound II, and Compound III are administered to said patient, and wherein Compound I, Compound II, and Compound III are comprised in a first pharmaceutical composition; or (ii) Compound I, Compound II, and Compound III-d are administered to said patient, and wherein Compound I, Compound II, and Compound III-d are comprised in a first pharmaceutical composition.

192. The method according to embodiment 191, wherein the first pharmaceutical composition is administered to the patient once daily.

193. A method of treating cystic fibrosis comprising administering to a patient in need thereof:

(a)

(A) 200 mg of at least one compound chosen from Compound I and pharmaceutically acceptable salts thereof per dosing once daily:

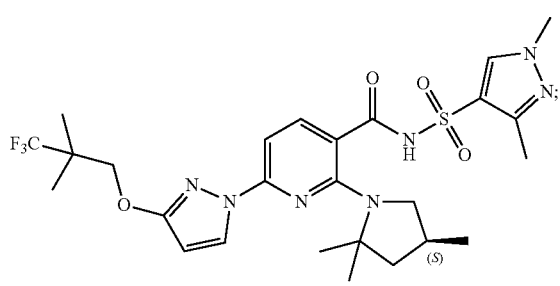

and (B) 100 mg of at least one compound chosen from Compound II and pharmaceutically acceptable salts thereof per dosing once daily:

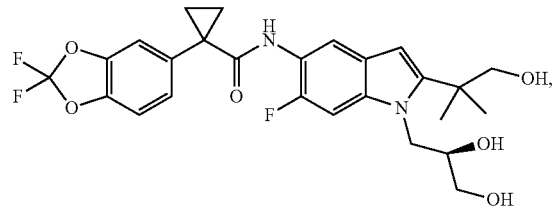 [SMILES: CC(C)(CO)c1cc2cc(NC(=O)C3(c4ccc5c(c4)OC(F)(F)O5)CC3)c(F)cc2n1C[C@@H](O)CO]

and (C) 150 mg of at least one compound chosen from Compound III and pharmaceutically acceptable salts thereof per dosing twice daily:

(Compound III)

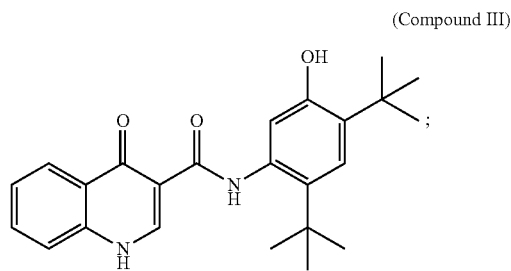 [SMILES: CC(C)(C)c1cc(C(C)(C)C)c(NC(=O)c2c[nH]c3ccccc3c2=O)cc1O]

or (b)

(A) 100 mg of at least one compound chosen from Compound I and pharmaceutically acceptable salts thereof per dosing once daily:

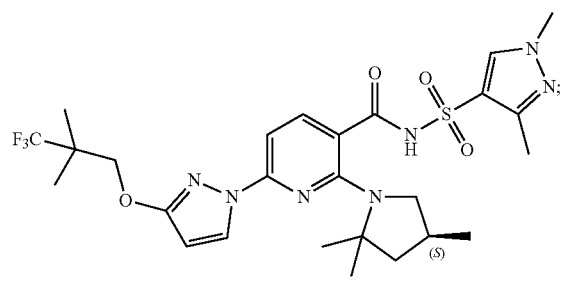

and (B) 100 mg of at least one compound chosen from Compound II and pharmaceutically acceptable salts thereof per dosing once daily:

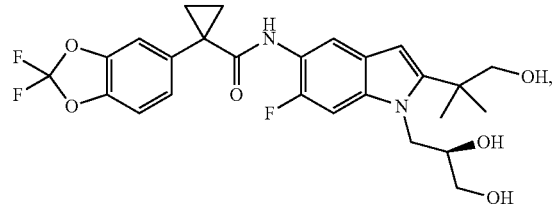 [SMILES: CC(C)(CO)c1cc2cc(NC(=O)C3(c4ccc5c(c4)OC(F)(F)O5)CC3)c(F)cc2n1C[C@@H](O)CO]

and (C) 150 mg of at least one compound chosen from Compound III and pharmaceutically acceptable salts thereof per dosing twice daily:

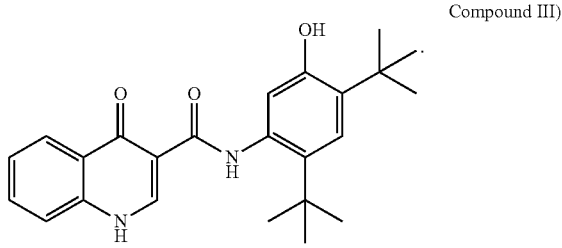 [SMILES: CC(C)(C)c1cc(C(C)(C)C)c(NC(=O)c2c[nH]c3ccccc3c2=O)cc1O]
(Compound III)

194. A method of treating cystic fibrosis comprising administering to a patient in need thereof:

(a)

(A) 200 mg of at least one compound chosen from Compound I and pharmaceutically acceptable salts thereof per dosing once daily:

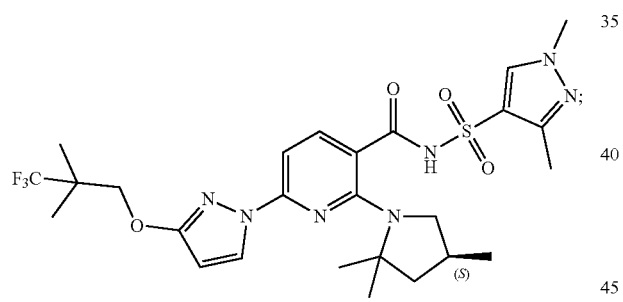

and (B) 100 mg of at least one compound chosen from Compound II and pharmaceutically acceptable salts thereof per dosing once daily:

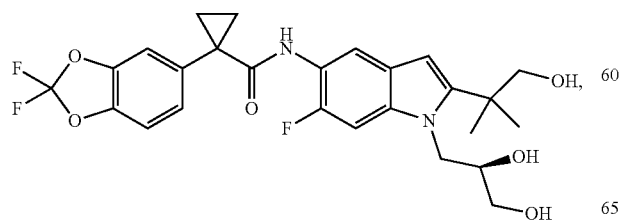

and (C) 150 mg of at least one compound chosen from Compound III-d and pharmaceutically acceptable salts thereof per dosing once daily:

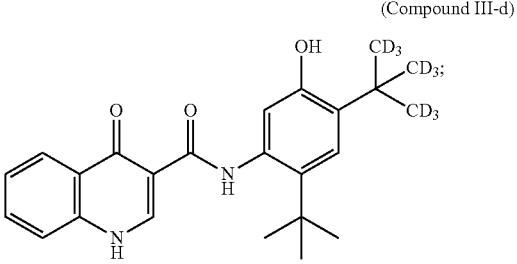 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]
(Compound III-d)

or (b)

(A) 100 mg of at least one compound chosen from Compound I and pharmaceutically acceptable salts thereof per dosing once daily:

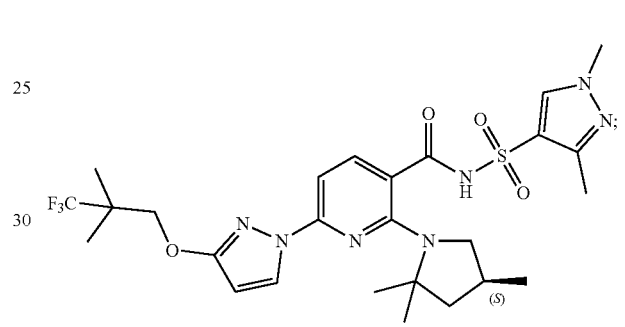

and (B) 100 mg of at least one compound chosen from Compound II and pharmaceutically acceptable salts thereof per dosing once daily:

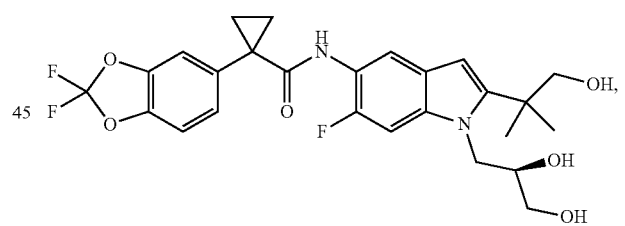

and (C) 150 mg of at least one compound chosen from Compound III-d and pharmaceutically acceptable salts thereof per dosing once daily:

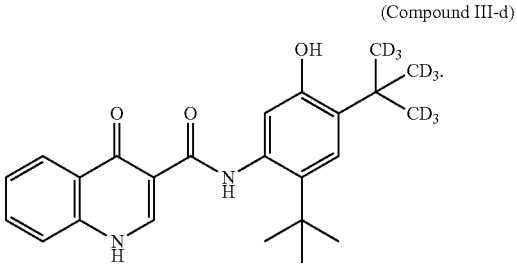 [SMILES: [2H]C([2H])([2H])C(c1cc(C(C)(C)C)c(NC(=O)c2c[nH]c3ccccc3c2=O)cc1O)(C([2H])([2H])[2H])C([2H])([2H])[2H]]
(Compound III-d)

195. A method of treating cystic fibrosis comprising administering to a patient in need thereof:

(a)

(A) 100 mg of at least one compound chosen from Compound I and pharmaceutically acceptable salts thereof per dosing twice daily:

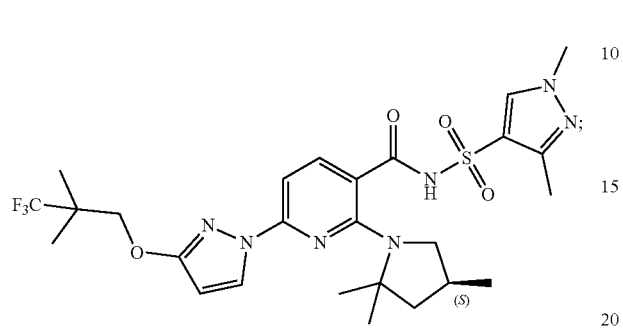

and (B) 50 mg of at least one compound chosen from Compound II and pharmaceutically acceptable salts thereof per dosing twice daily:

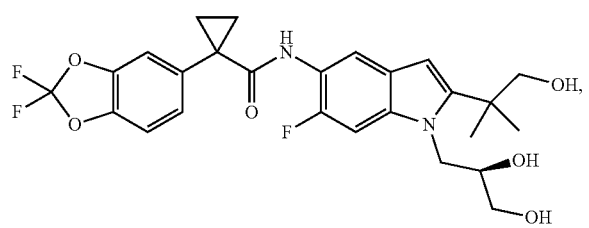 [SMILES: CC(C)(CO)c1cc2cc(NC(=O)C3(c4ccc5c(c4)OC(F)(F)O5)CC3)c(F)cc2n1C[C@@H](O)CO]

and (C) 150 mg of at least one compound chosen from Compound III and pharmaceutically acceptable salts thereof per dosing twice daily:

(Compound III)

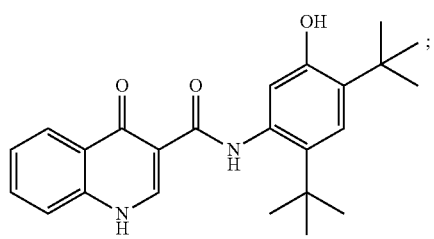

or (b)

(A) 50 mg of at least one compound chosen from Compound I and pharmaceutically acceptable salts thereof per dosing twice daily:

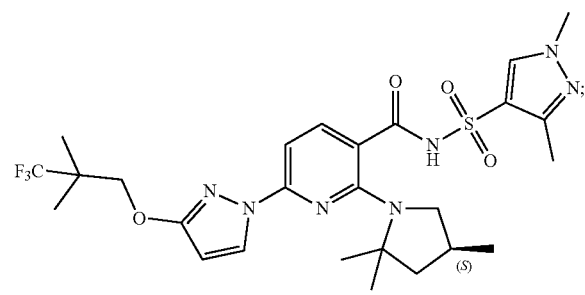

and (B) 50 mg of at least one compound chosen from Compound II and pharmaceutically acceptable salts thereof per dosing twice daily:

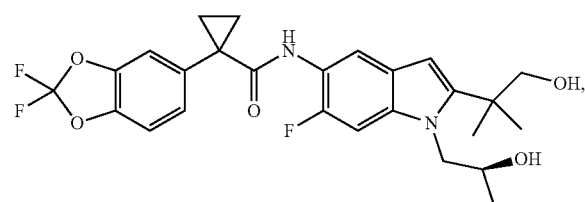

and (C) 150 mg of at least one compound chosen from Compound III and pharmaceutically acceptable salts thereof per dosing twice daily:

(Compound III)

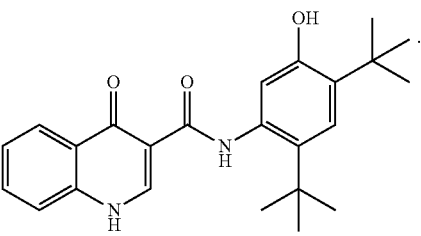

196. The method according to embodiments 193 or 194 or 195, wherein said patient has cystic fibrosis is chosen from patients with F508del/minimal function genotypes, patients with F508del/F508del genotypes, patients with F508del/gating genotypes, and patients with F508del/residual function genotypes.

197. The method according to embodiment 196, wherein the patient with a F508del/minimal function genotype has a minimal function mutation selected from:

| Mutation | | | | |
|---|---|---|---|---|
| S4X | C276X | G542X | R792X | E1104X |
| G27X | Q290X | G550X | E822X | R1158X |
| Q39X | G330X | Q552X | W846X | R1162X |
| W57X | W401X | R553X | Y849X | S1196X |
| E60X | Q414X | E585X | R851X | W1204X |
| R75X | S434X | G673X | Q890X | L1254X |

-continued

| Mutation | | | | |
|---|---|---|---|---|
| E92X | S466X | Q685X | S912X | S1255X |
| Q98X | S489X | R709X | Y913X | W1282X |
| Y122X | Q493X | K710X | W1089X | Q1313X |
| E193X | W496X | L732X | Y1092X | E1371X |
| L218X | C524X | R764X | W1098X | Q1382X |
| Q220X | Q525X | R785X | R1102X | Q1411X |
| 185 + 1G→T | 711 + 5G→A | 1717 − 8G→A | 2622 + 1G→A | 3121 − 1G→A |
| 296 + 1G→A | 712 − 1G→T | 1717 − 1G→A | 2790 − 1G→C | 3500 − 2A→G |
| 405 + 1G→A | 1248 + 1G→A | 1811 + 1G→C | 3040→C | 3600 + 2insT |
| 405 + 3A→C | 1249 − 1G→A | 1811 + 1.6 kbA→G | (G970R) | 3850 − 1G→A |
| 406 − 1G→A | 1341 + 1G→A | 1812 − 1G→A | 3120→A | 4005 + 1G→A |
| 621 + 1G→T | 1525 − 2A→G | 1898 + 1G→A | 3120 + 1G→A | 4374 + 1G→T |
| 711 + 1G→T | 1525 − 1G→A | 1898 + 1G→C | 3121 − 2A→G | |
| 182delT | 1119delA | 1782delA | 2732insA | 3876delA |
| 306insA | 1138insG | 1824delA | 2869insG | 3878delG |
| 365-366insT | 1154insTC | 2043delG | 2896insAG | 3905insT |
| 394delTT | 1161delC | 2143delT | 2942insT | 4016insT |
| 442delA | 1213delT | 2183AA→G[a] | 2957delT | 4021dupT |
| 444delA | 1259insA | 2184delA | 3007delG | 4040delA |
| 457TAT→G | 1288insTA | 2184insA | 3028delA | 4279insA |
| 541delC | 1471delA | 2307insA | 3171delC | 4326delTC |
| 574delA | 1497delGG | 2347delG | 3659delC | |
| 663delT | 1548delG | 2585delT | 3737delA | |
| 935delA | 1609delCA | 2594delGT | 3791delC | |
| 1078delT | 1677delTA | 2711delT | 3821delT | |
| CFTRdele2, 3 | | 1461ins4 | | 2991del32 |
| CFTRdele22, 23 | | 1924del7 | | 3667ins4 |
| 124del23bp | | 2055del9→A | | 4010del4 |
| 852del22 | | 2105-2117del13insAGAAA | | 4209TGTT→AA |
| 991del5 | | 2721del11 | | |
| A46D[b] | V520F | Y569D[b] | | N1303K, |
| G85E | A559T[b] | L1065P | | |
| R347P | R560T | R1066C | | |
| L467P[b] | R560S | L1077P[b] | | |
| I507del | A561E | M1101K | | |
| Q2X | L218X | Q525X | R792X | E1104X |
| S4X | Q220X | G542X | E822X | W1145X |
| W19X | Y275X | G550X | W882X | R1158X |
| G27X | C276X | Q552X | W846X | R1162X |
| Q39X | Q290X | R553X | Y849X | S1196X |
| W57X | G330X | E585X | R851X | W1204X |
| E60X | W401X | G673X | Q890X | L1254X |
| R75X | Q414X | Q685X | S912X | S1255X |
| L88X | S434X | R709X | Y913X | W1282X |
| E92X | S466X | K710X | Q1042X | Q1313X |
| Q98X | S489X | Q715X | W1089X | Q1330X |
| Y122X | Q493X | L732X | Y1092X | E1371X |
| E193X | W496X | R764X | W1098X | Q1382X |
| W216X | C524X | R785X | R1102X | Q1411X |
| 185 + 1G→T | 711 + 5G→A | 1717 − 8G→A | 2622 + 1G→A | 3121 − 1G→A |
| 296 + 1G→A | 712 − 1G→T | 1717 − 1G→A | 2790 − 1G→C | 3500 − 2A→G |
| 296 + 1G→T | 1248 + 1G→A | 1811 + 1G→C | 3040G→C | 3600 + 2insT |
| 405 + 1G→A | 1249 − 1G→A | 1811 + 1.6 kbA→G | (G970R) | 3850 − 1G→A |
| 405 + 3A→C | 1341 + 1G→A | 1811 + 1643G→T | 3120 − 1G→A | 4005 + 1G→A |
| 406 − 1G→A | 1525 − 2A→G | 1812 − 1G→A | 3120 + 1G→A | 4374 + 1G→T |
| 621 + 1G→T | 1525 − 1G→A | 1898 + 1G→A | 3121 − 2A→G | |
| 711 + 1G→T | | 1898 + 1G→C | | |
| 182delT | 1078delT | 1677delTA | 2711delT | 3737delA |
| 306insA | 1119delA | 1782delA | 2732insA | 3791delC |
| 306delTAGA | 1138insG | 1824delA | 2869insG | 3821delT |
| 365-366insT | 1154insTC | 1833delT | 2896insAG | 3876delA |
| 394delTT | 1161delC | 2043delG | 2942insT | 3878delG |
| 442delA | 1213delT | 2143delT | 2957delT | 3905insT |
| 444delA | 1259insA | 2183AA→G[a] | 3007delG | 4016insT |
| 457TAT→G | 1288insTA | 2184delA | 3028delA | 4021dupT |
| 541delC | 1343delG | 2184insA | 3171delC | 4022insT |
| 574delA | 1471delA | 2307insA | 3171insC | 4040delA |
| 663delT | 1497delGG | 2347delG | 3271delGG | 4279insA |
| 849delG | 1548delG | 2585delT | 3349insT | 4326delTC |
| 935delA | 1609del CA | 2594delGT | 3659delC | |
| CFTRdele1 | CFTRdele16-17b | | 1461ins4 | |
| CFTRdele2 | CFTRdele17a, 17b | | 1924del7 | |
| CFTRdele2, 3 | CFTRdele17a-18 | | 2055del9→A | |
| CFTRdele2-4 | CFTRdele19 | | 2105-2117del13insAGAAA | |
| CFTRdele3-10, 14b-16 | CFTRdele19-21 | | 2372del8 | |
| CFTRdele4-7 | CFTRdele21 | | 2721del11 | |
| CFTRdele4-11 | CFTRdele22-24 | | 2991del32 | |

-continued

| Mutation | | | |
|---|---|---|---|
| CFTR50kbdel | | CFTRdele22, 23 | 3121-977_3499 + 248del2515 |
| CFTRdup6b-10 | | 124del23bp | 3667ins4 |
| CFTRdele11 | | 602del14 | 4010del4 |
| CFTRdele13, 14a | | 852del22 | 4209TGTT→AA |
| CFTRdele14b-17b | | 991del5 | |
| A46D[b] | V520F | Y569D[b] | N1303K |
| G85E | A559T[b] | L1065P | |
| R347P | R560T | R1066C | |
| LA67P[b] | R560S | L1077P[b] | |
| I507del | A561E | M1101K | |

[a]Also known as 2183delAA→G.

198. The method according to embodiment 196, wherein the patient with a F508del/gating genotype has a gating mutation selected from G178R, S549N, S549R, G551D, G551S, G1244E, S1251N, S1255P, and G1349D.

199. The method according to embodiment 196, wherein the patient with a F508del/residual function genotype has a residual function mutation selected from 2789+5G→A, 3849+10kbC→T, 3272-26A→G, 711+3A→G, E56K, P67L, R74W, D110E, D110H, R117C, L206W, R347H, R352Q, A455E, D579G, E831X, S945L, S977F, F1052V, R1070W, F1074L, D1152H, D1270N, E193K, K1060T, R117H, S1235R, 11027T, R668C, G576A, M470V, L997F, R75Q, R1070Q, R31C, D614G, G1069R, R1162L, E56K, A1067T, E193K, and K1060T.

200. The method according to any one of embodiments 1-199, wherein the absolute change in said patient's percent predicted forced expiratory volume in one second (ppFEV$_1$) after 29 days of administration of said at least one compound chosen from Compound I and pharmaceutically acceptable salts thereof, at least one compound chosen from Compound II and pharmaceutically acceptable salts thereof, and at least one compound chosen from Compound III or III-d and pharmaceutically acceptable salts thereof ranges from 3% to 40% relative to the ppFEV1 of the patient prior to said administration.

201. The method according to any one of embodiments 1-200, wherein said absolute change in said patient's ppFEV$_1$ ranges from 3% to 35%.

EXAMPLES

I. Methods of Preparing Compounds
General Experimental Procedures

Reagents and starting materials were obtained by commercial sources unless otherwise stated and were used without purification. Proton and carbon NMR spectra were acquired on either of a Bruker Biospin DRX 400 MHz FTNMR spectrometer operating at a $^1$H and $^{13}$C resonant frequency of 400 and 100 MHz respectively, or on a 300 MHz NMR spectrometer. One dimensional proton and carbon spectra were acquired using a broadband observe (BBFO) probe with 20 Hz sample rotation at 0.1834 and 0.9083 Hz/Pt digital resolution respectively. Proton and carbon spectra were either acquired with temperature control at 30° C. or ambient temperature using standard, previously published pulse sequences and routine processing parameters. Final purity of compounds was determined by reversed phase UPLC using an Acquity UPLC BEH C$_{18}$ column (50×2.1 mm, 1.7 µm particle) made by Waters (pn: 186002350), and a dual gradient run from 1-99% mobile phase B over 3.0 minutes. Mobile phase A=H$_2$O (0.05% CF$_3$CO$_2$H). Mobile phase B=CH$_3$CN (0.035% CF$_3$CO$_2$H).

Flow rate=1.2 mL/min, injection volume=1.5 µL, and column temperature=60° C. Final purity was calculated by averaging the area under the curve (AUC) of two UV traces (220 nm, 254 nm). Low-resolution mass spectra were obtained using a single quadrupole mass spectrometer with a mass accuracy of 0.1 Da and a minimum resolution of 1000 amu across the detection range using electrospray ionization (ESI) using the hydrogen ion (H$^+$). Optical purity of methyl (2S)-2,4-dimethyl-4-nitro-pentanoate was determined using chiral gas chromatography (GC) analysis on an Agilent 7890A/MSD 5975C instrument, using a Restek Rt-βDEXcst (30m×0.25 mm×0.25 um_df) column, with a 2.0 mL/min flow rate (H2 carrier gas), at an injection temperature of 220° C. and an oven temperature of 120° C., 15 minutes.

Compounds I, II, III, and III-d can be prepared by any suitable method in the art, for example, PCT Publication Nos. WO 2011/133751 and WO 2015/160787 and U.S. Pat. No. 8,865,902.

Example 1: Synthesis of Compound I

Part A: Synthesis of (4S)-2,2,4-trimethylpyrrolidine Hydrochloride

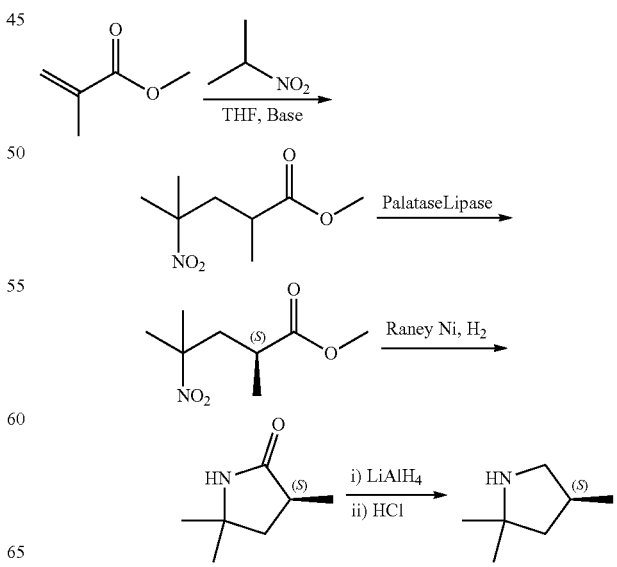

Step 1: Synthesis of methyl-2,4-dimethyl-4-nitro-pentanoate

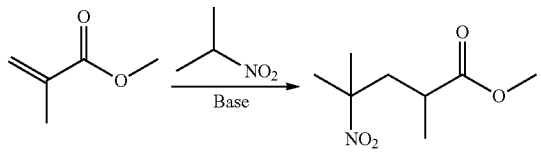

Tetrahydrofuran (THF, 4.5 L) was added to a 20 L glass reactor and stirred under $N_2$ at room temperature. 2-Nitropropane (1.5 kg, 16.83 mol) and 1,8-diazabicyclo[5.4.0]undec-7-ene (DBU) (1.282 kg, 8.42 mol) were then charged to the reactor, and the jacket temperature was increased to 50° C. Once the reactor contents were close to 50° C., methyl methacrylate (1.854 kg, 18.52 mol) was added slowly over 100 minutes. The reaction temperature was maintained at or close to 50° C. for 21 hours. The reaction mixture was concentrated in vacuo then transferred back to the reactor and diluted with methyl tert-butyl ether (MTBE) (14 L). 2 M HCl (7.5 L) was added, and this mixture was stirred for 5 minutes then allowed to settle. Two clear layers were visible—a lower yellow aqueous phase and an upper green organic phase. The aqueous layer was removed, and the organic layer was stirred again with 2 M HCl (3 L). After separation, the HCl washes were recombined and stirred with MTBE (3 L) for 5 minutes. The aqueous layer was removed, and all of the organic layers were combined in the reactor and stirred with water (3 L) for 5 minutes. After separation, the organic layers were concentrated in vacuo to afford a cloudy green oil. Crude product was treated with $MgSO_4$ and filtered to afford methyl-2,4-dimethyl-4-nitropentanoate as a clear green oil (3.16 kg, 99% yield).

$^1$H NMR (400 MHz, Chloroform-d) δ 3.68 (s, 3H), 2.56-2.35 (m, 2H), 2.11-2.00 (m, 1H), 1.57 (s, 3H), 1.55 (s, 3H), 1.19 (d, J=6.8 Hz, 3H).

Step 2: Synthesis of methyl (2S)-2,4-dimethyl-4-nitro-pentanoate

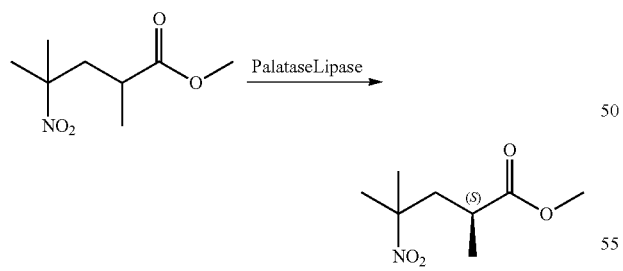

A reactor was charged with purified water (2090 L; 10 vol) and then potassium phosphate monobasic (27 kg, 198.4 moles; 13 g/L for water charge). The pH of the reactor contents was adjusted to pH 6.5 (±0.2) with 20% (w/v) potassium carbonate solution. The reactor was charged with racemic methyl-2,4-dimethyl-4-nitro-pentanoate (209 kg; 1104.6 moles), and Palatase 20000L lipase (13 L, 15.8 kg; 0.06 vol).

The reaction mixture was adjusted to 32±2° C. and stirred for 15-21 hours, and pH 6.5 was maintained using a pH stat with the automatic addition of 20% potassium carbonate solution. When the racemic starting material was converted to >98% ee of the S-enantiomer, as determined by chiral GC, external heating was switched off. The reactor was then charged with MTBE (35 L; 5 vol), and the aqueous layer was extracted with MTBE (3 times, 400-1000 L). The combined organic extracts were washed with aqueous $Na_2CO_3$ (4 times, 522 L, 18% w/w 2.5 vol), water (523 L; 2.5 vol), and 10% aqueous NaCl (314 L, 1.5 vol). The organic layer was concentrated in vacuo to afford methyl (2S)-2,4-dimethyl-4-nitro-pentanoate as a mobile yellow oil (>98% ee, 94.4 kg; 45% yield).

Step 3: Synthesis of (3S)-3,5,5-trimethylpyrrolidin-2-one

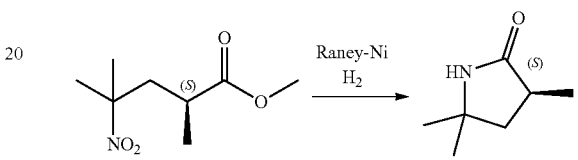

A 20 L reactor was purged with $N_2$. The vessel was charged sequentially with DI water-rinsed, damp Raney® Ni (2800 grade, 250 g), methyl (2S)-2,4-dimethyl-4-nitro-pentanoate (1741 g, 9.2 mol), and ethanol (13.9 L, 8 vol). The reaction was stirred at 900 rpm, and the reactor was flushed with H2 and maintained at ~2.5 bar. The reaction mixture was then warmed to 60° C. for 5 hours. The reaction mixture was cooled and filtered to remove Raney nickel, and the solid cake was rinsed with ethanol (3.5 L, 2 vol). The ethanolic solution of the product was combined with a second equal sized batch and concentrated in vacuo to reduce to a minimum volume of ethanol (~1.5 volumes). Heptane (2.5 L) was added, and the suspension was concentrated again to ~1.5 volumes. This was repeated 3 times; the resulting suspension was cooled to 0-5° C., filtered under suction, and washed with heptane (2.5 L). The product was dried under vacuum for 20 minutes then transferred to drying trays and dried in a vacuum oven at 40° C. overnight to afford (3S)-3,5,5-trimethylpyrrolidin-2-one as a white crystalline solid (2.042 kg, 16.1 mol, 87%). $^1$H NMR (400 MHz, Chloroform-d) δ 6.39 (s, 1H), 2.62 (ddq, J=9.9, 8.6, 7.1 Hz, 1H), 2.17 (dd, J=12.4, 8.6 Hz, 1H), 1.56 (dd, J=12.5, 9.9 Hz, 1H), 1.31 (s, 3H), 1.25 (s, 3H), 1.20 (d, J=7.1 Hz, 3H).

Step 4: Synthesis of (4S)-2,2,4-trimethylpyrrolidine Hydrochloride

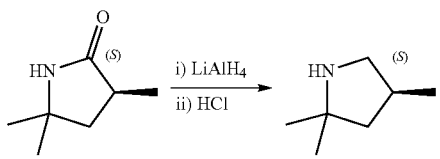

A glass lined 120 L reactor was charged with lithium aluminum hydride pellets (2.5 kg, 66 mol) and dry THF (60 L) and warmed to 30° C. The resulting suspension was charged with (S)-3,5,5-trimethylpyrrolidin-2-one (7.0 kg, 54 mol) in THF (25 L) over 2 hours while maintaining the reaction temperature at 30 to 40° C. After complete addition, the reaction temperature was increased to 60-63° C. and maintained overnight. The reaction mixture was cooled to 22° C., then cautiously quenched with the addition of ethyl acetate (EtOAc) (1.0 L, 10 moles), followed by a mixture of THF (3.4 L) and water (2.5 kg, 2.0 eq), and then a mixture of water (1.75 kg) with 50% aqueous sodium hydroxide (750 g, 2 equiv. water with 1.4 equiv. sodium hydroxide relative to aluminum), followed by 7.5 L water. After the addition was complete, the reaction mixture was cooled to room temperature, and the solid was removed by filtration and washed with THF (3×25 L). The filtrate and washings were combined and treated with 5.0 L (58 moles) of aqueous 37% HCl (1.05 equiv.) while maintaining the temperature below 30° C. The resultant solution was concentrated by vacuum distillation to a slurry. Isopropanol (8 L) was added and the solution was concentrated to near dryness by vacuum distillation. Isopropanol (4 L) was added, and the product was slurried by warming to about 50° C. MTBE (6 L) was added, and the slurry was cooled to 2-5° C. The product was collected by filtration and rinsed with 12 L MTBE and dried in a vacuum oven (55° C./300 torr/$N_2$ bleed) to afford (4S)-2,2,4-trimethylpyrrolidine·HCl as a white, crystalline solid (6.21 kg, 75% yield). $^1$H NMR (400 MHz, DMSO-d6) δ 9.34 (br d, 2H), 3.33 (dd, J=11.4, 8.4 Hz, 1H), 2.75 (dd, J=11.4, 8.6 Hz, 1H), 2.50-2.39 (m, 1H), 1.97 (dd, J=12.7, 7.7 Hz, 1H), 1.42 (s, 3H), 1.38 (dd, J=12.8, 10.1 Hz, 1H), 1.31 (s, 3H), 1.05 (d, J=6.6 Hz, 3H).

Part B: Preparation of N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (Compound I)

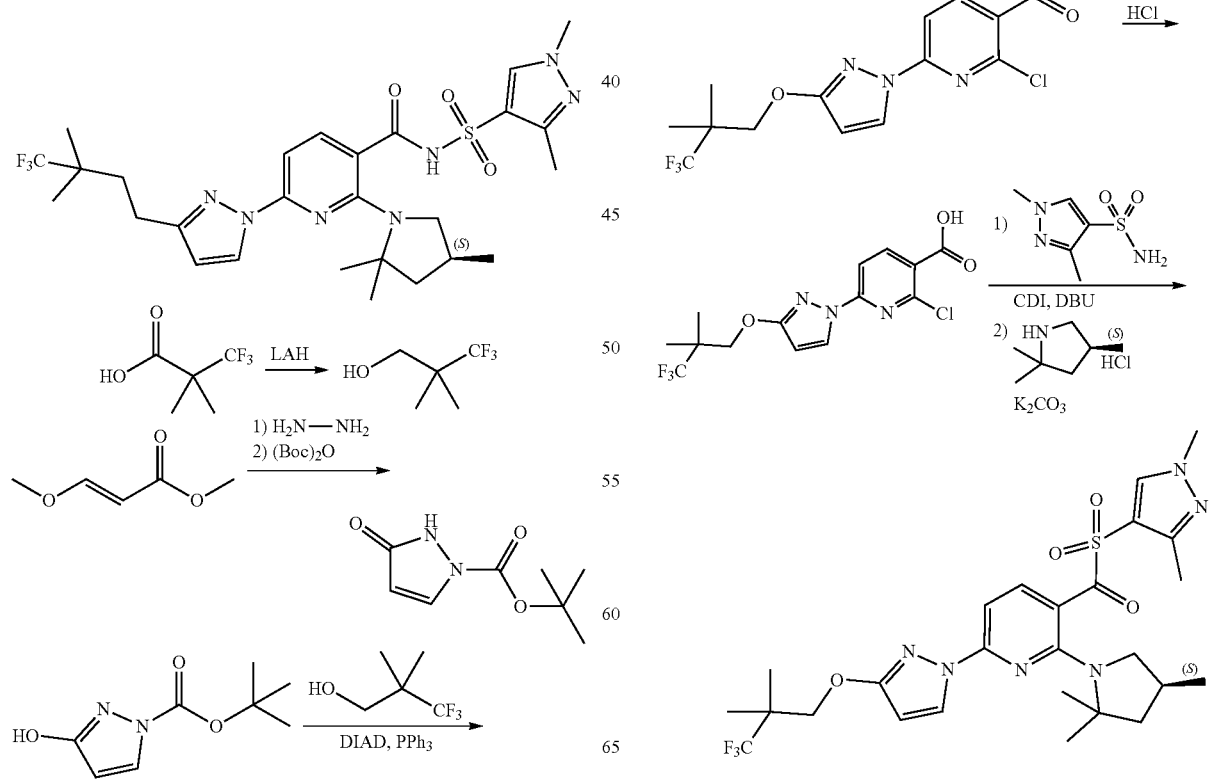

Preparation of Starting Materials 3,3,3-Trifluoro-2,2-dimethyl-propan-1-ol

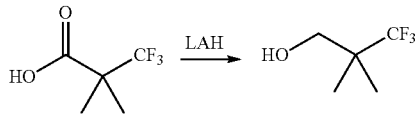

A 1 L 3 neck round bottom flask was fitted with a mechanical stirrer, a cooling bath, an addition funnel, and a J-Kem temperature probe. The vessel was charged with lithium aluminum hydride (LAH) pellets (6.3 g, 0.1665 mol) under a nitrogen atmosphere. The vessel was then charged with tetrahydrofuran (200 mL) under a nitrogen atmosphere. The mixture was allowed to stir at room temperature for 0.5 hours to allow the pellets to dissolve. The cooling bath was then charged with crushed ice in water and the reaction temperature was lowered to 0° C. The addition funnel was charged with a solution of 3,3,3-trifluoro-2,2-dimethyl-propanoic acid (20 g, 0.1281 mol) in tetrahydrofuran (60 mL) and the clear pale yellow solution was added drop wise over 1 hour. After the addition was complete the mixture was allowed to slowly warm to room temperature and stirring was continued for 24 hours. The suspension was cooled to 0° C. with a crushed ice-water in the cooling bath and then quenched by the very slow and drop wise addition of water (6.3 ml), followed by sodium hydroxide solution (15 weight %; 6.3 mL) and then finally with water (18.9 mL). The reaction temperature of the resulting white suspension was recorded at 5° C. The suspension was stirred at ~5° C. for 30 minutes and then filtered through a 20 mm layer of Celite. The filter cake was washed with tetrahydrofuran (2×100 mL). The filtrate was dried over sodium sulfate (150 g) and then filtered. The filtrate was concentrated under reduced pressure to provide a clear colorless oil (15 g) containing a mixture of the product 3,3,3-trifluoro-2,2-dimethyl-propan-1-ol in THF (73% weight of product ~10.95 g, and 27 wt. % THF as determined by 1H-NMR). The distillate from the rotary evaporation was distilled at atmospheric pressure using a 30 cm Vigreux column to provide 8.75 g of a residue containing 60% weight of THF and 40% weight of product (~3.5 g). The estimated total amount of product is 14.45 g (79% yield). 1H NMR (400 MHz, DMSO-d6) δ 4.99 (t, J=5.7 Hz, 1H), 3.38 (dd, J=5.8, 0.9 Hz, 2H), 1.04 (d, J=0.9 Hz, 6H).

Tert-Butyl 3-oxo-2,3-dihydro-1H-pyrazole-1-carboxylate

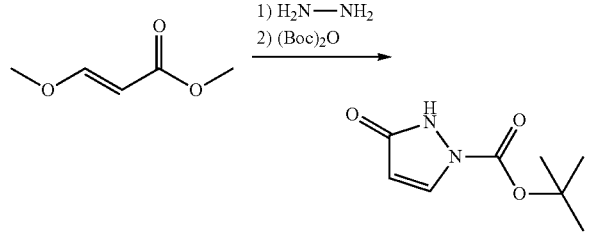

A 50 L Syrris controlled reactor was started and jacket set to 20° C., stirring at 150 rpm, reflux condenser (10° C.) and nitrogen purge. MeOH (2.860 L) and methyl (E)-3-methoxyprop-2-enoate (2.643 kg, 22.76 mol) were added and the reactor was capped. The reaction was heated to an internal temperature of 40° C. and the system was set to hold jacket temp at 40° C. Hydrazine hydrate (1300 g of 55% w/w, 22.31 mol) was added portion wise via addition funnel over 30 min. The reaction was heated to 60° C. for 1 h. The reaction mixture was cooled to 20° C. and triethyamine (2.483 kg, 3.420 L, 24.54 mol) was added portion wise (exothermic), maintaining reaction temp<30° C. A solution of Boc anhydride (di-tert-butyl dicarbonate) (4.967 kg, 5.228 L, 22.76 mol) in MeOH (2.860 L) was added portion wise maintaining temperature <45° C. The reaction mixture was stirred at 20° C. for 16 h. The reaction solution was partially concentrated to remove MeOH, resulting in a clear light amber oil. The resulting oil was transferred to the 50 L reactor, stirred and added water (7.150 L) and heptane (7.150 L). The additions caused a small amount of the product to precipitate. The aqueous layer was drained into a clean container and the interface and heptane layer were filtered to separate the solid (product). The aqueous layer was transferred back to the reactor, and the collected solid was placed back into the reactor and mixed with the aqueous layer. A dropping funnel was added to the reactor and loaded with acetic acid (1.474 kg, 1.396 L, 24.54 mol), then began dropwise addition of acid. The jacket was set to 0° C. to absorb the quench exotherm. After addition (pH=5), the reaction mixture was stirred for 1 h. The solid was collected by filtration and washed with water (7.150 L), and washed a second time with water (3.575 L) and pulled dry. The crystalline solid was scooped out of the filter into a 20 L rotovap bulb and heptane (7.150 L) was added. The mixture was slurried at 45° C. for 30 mins, and then distilled off 1-2 volumes of solvent. The slurry in the rotovap flask was filtered and the solids washed with heptane (3.575 L) and pulled dry. The solid was further dried in vacuo (50° C., 15 mbar) to give tert-butyl 5-oxo-1H-pyrazole-2-carboxylate (2921 g, 71%) as coarse, crystalline solid. 1H NMR (400 MHz, DMSO-d6) δ 10.95 (s, 1H), 7.98 (d, J=2.9 Hz, 1H), 5.90 (d, J=2.9 Hz, 1H), 1.54 (s, 9H).

Step A: Tert-Butyl 3-(3,3,3-trifluoro-2,2-dimethyl-propoxy)pyrazole-1-carboxylate

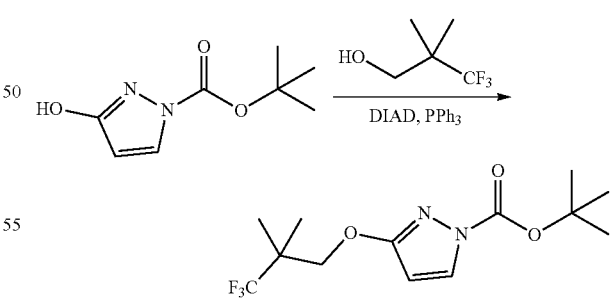

A mixture of 3,3,3-trifluoro-2,2-dimethyl-propan-1-ol (10 g, 70.36 mmol) and tert-butyl 3-hydroxypyrazole-1-carboxylate (12.96 g, 70.36 mmol) in toluene (130 mL) was treated with triphenyl phosphine (20.30 g, 77.40 mmol) followed by isopropyl N-isopropoxycarbonyliminocarbamate (14.99 mL, 77.40 mmol) and the mixture was stirred at 110° C. for 16 hours. The yellow solution was concentrated under reduced pressure, diluted with heptane (100 mL) and the precipitated triphenylphosphine oxide was removed by filtration and washed with heptane/toluene 4:1 (100 mL). The yellow filtrate was evaporated and the residue purified by silica gel chromatography with a linear gradient of ethyl acetate in hexane (0-40%) to give tert-butyl 3-(3,3,3-trifluoro-2,2-dimethyl-propoxy)pyrazole-1-carboxylate (12.3 g, 57%) as an off white solid. ESI-MS m z calc. 308.13477, found 309.0 (M+1)+; Retention time: 1.84 minutes. $^1$H NMR (400 MHz, DMSO-d6) δ 8.10 (d, J=3.0 Hz, 1H), 6.15 (d, J=3.0 Hz, 1H), 4.18 (s, 2H), 1.55 (s, 9H), 1.21 (s, 6H).

Step B: 3-(3,3,3-trifluoro-2,2-dimethyl-propoxy)-1H-pyrazole

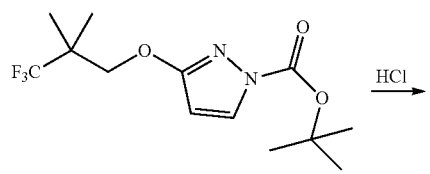

tert-Butyl 3-(3,3,3-trifluoro-2,2-dimethyl-propoxy)pyrazole-1-carboxylate (13.5 g, 43.79 mmol) was treated with 4 M hydrogen chloride in dioxane (54.75 mL, 219.0 mmol) and the mixture was stirred at 45° C. for 1 hour. The reaction mixture was evaporated to dryness and the residue was extracted with 1 M aqueous NaOH (100 ml) and methyl tert-butyl ether (100 ml), washed with brine (50 ml) and extracted with methyl tert-butyl ether (50 ml). The combined organic phases were dried, filtered and evaporated to give 3-(3,3,3-trifluoro-2,2-dimethyl-propoxy)-1H-pyrazole (9.0 g, 96%) as an off white waxy solid. $^{ESI-MS}$ m/z calc. 208.08235, found 209.0 (M+1)$^+$; Retention time: 1.22 minutes. $^1$H NMR (400 MHz, DMSO-d6) δ 11.91 (s, 1H), 7.52 (d, J=2.2 Hz, 1H), 5.69 (t, J=2.3 Hz, 1H), 4.06 (s, 2H), 1.19 (s, 6H).

Step C: Tert-Butyl 2,6-dichloropyridine-3-carboxylate

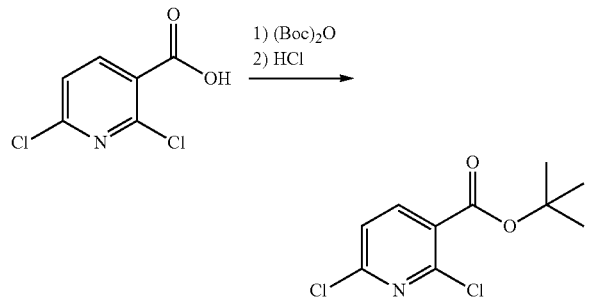

A solution of 2,6-dichloropyridine-3-carboxylic acid (10 g, 52.08 mmol) in THF (210 mL) was treated successively with di-tert-butyl dicarbonate (17 g, 77.89 mmol) and 4-(dimethylamino)pyridine (3.2 g, 26.19 mmol) and left to stir overnight at room temperature. At this point, HCl 1N (400 mL) was added and the mixture was stirred vigorously for about 10 minutes. The product was extracted with ethyl acetate (2×300 mL) and the combined organics layers were washed with water (300 mL) and brine (150 mL) and dried over sodium sulfate and concentrated under reduced pressure to give 12.94 g (96% yield) of tert-butyl 2,6-dichloropyridine-3-carboxylate as a colorless oil. ESI-MS m z calc. 247.01668, found 248.1 (M+1)+; Retention time: 2.27 minutes. $^1$H NMR (300 MHz, CDCl$_3$) ppm 1.60 (s, 9H), 7.30 (d, J=7.9 Hz, 1H), 8.05 (d, J=8.2 Hz, 1H).

Step D: Tert-Butyl 2-chloro-6-[3-(3,3,3-trifluoro-2,2-dimethyl-propoxy)pyrazol-1-yl]pyridine-3-carboxylate

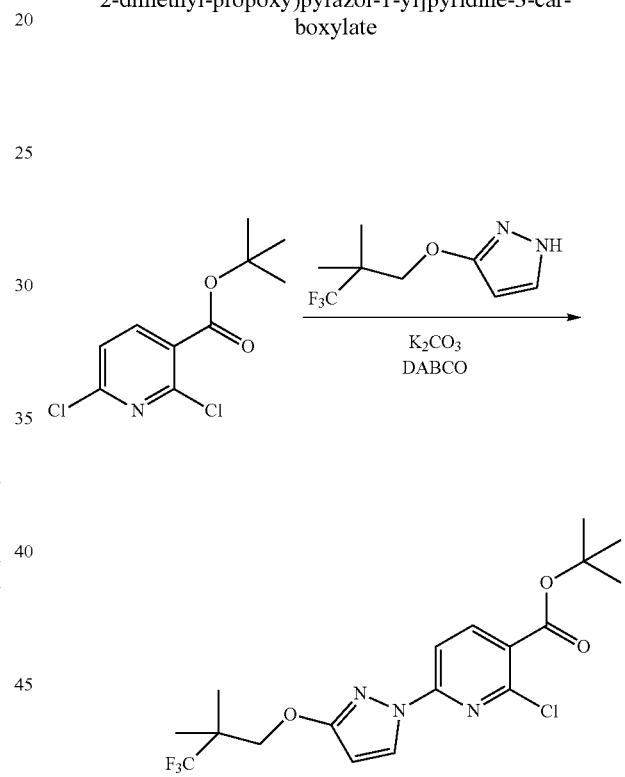

To a solution of tert-butyl 2,6-dichloropyridine-3-carboxylate (10.4 g, 41.9 mmol) and 3-(3,3,3-trifluoro-2,2-dimethyl-propoxy)-1H-pyrazole (9.0 g, 41.93 mmol) in DMF (110 mL) were added potassium carbonate (K$_2$CO$_3$) (7.53 g, 54.5 mmol) and 1,4-diazabicyclo[2.2.2]octane (DABCO) (706 mg, 6.29 mmol) and the mixture was stirred at room temperature for 16 hours. The cream suspension was cooled in a cold water bath and cold water (130 mL) was slowly added. The thick suspension was stirred at room temperature for 1 hour, filtered and washed with plenty of water to give tert-butyl 2-chloro-6-[3-(3,3,3-trifluoro-2,2-dimethyl-propoxy)pyrazol-1-yl]pyridine-3-carboxylate (17.6 g, 99%) as an off white solid. ESI-MS m z calc. 419.12234, found 420.0 (M+1)+; Retention time: 2.36 minutes. $^1$H NMR (400 MHz, DMSO-d6) δ 8.44 (d, J=2.9 Hz, 1H), 8.31 (d, J=8.4 Hz, 1H), 7.76 (d, J=8.4 Hz, 1H), 6.26 (d, J=2.9 Hz, 1H), 4.27 (s, 2H), 1.57 (s, 9H), 1.24 (s, 6H).

Step E: 2-chloro-6-[3-(3,3,3-trifluoro-2,2-dimethyl-propoxy)pyrazol-1-yl]pyridine-3-carboxylic acid

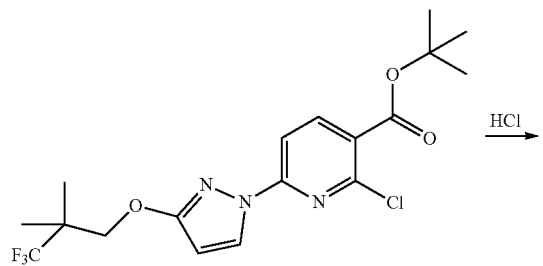

by filtration, washed with isopropanol/water 1:1 (50 mL), plenty of water and dried in a drying cabinet under vacuum at 45-50° C. with a nitrogen bleed overnight to give 2-chloro-6-[3-(3,3,3-trifluoro-2,2-dimethyl-propoxy)pyrazol-1-yl]pyridine-3-carboxylic acid (13.7 g, 91%) as an off white solid. ESI-MS m z calc. 363.05975, found 364.0 (M+1)+; Retention time: 1.79 minutes. $^1$H NMR (400 MHz, DMSO-d6) δ 13.61 (s, 1H), 8.44 (d, J=2.9 Hz, 1H), 8.39 (d, J=8.4 Hz, 1H), 7.77 (d, J=8.4 Hz, 1H), 6.25 (d, J=2.9 Hz, 1H), 4.28 (s, 2H), 1.24 (s, 6H).

Step F: 2-Chloro-N-(1,3-dimethylpyrazol-4-yl)sulfonyl-6-[3-(3,3,3-trifluoro-2,2-dimethyl-propoxy)pyrazol-1-yl]pyridine-3-carboxamide

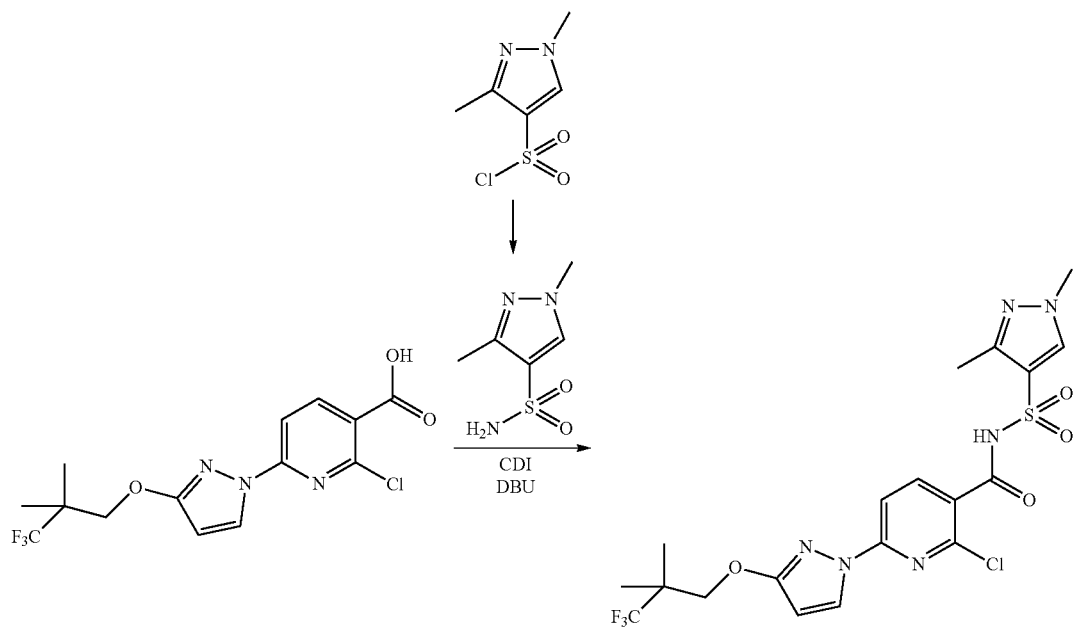

-continued

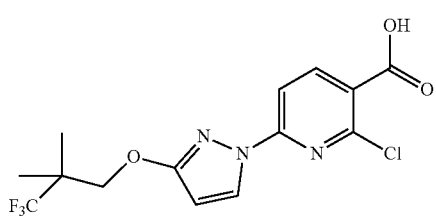

Tert-butyl 2-chloro-6-[3-(3,3,3-trifluoro-2,2-dimethyl-propoxy)pyrazol-1-yl]pyridine-3-carboxylate (17.6 g, 40.25 mmol) was suspended in isopropanol (85 mL) treated with hydrochloric acid (34 mL of 6 M, 201 mmol) and heated to reflux for 3 hours (went almost complete into solution at reflux and started to precipitate again). The suspension was diluted with water (51 mL) at reflux and left to cool to room temperature under stirring for 2.5 h. The solid was collected 2-Chloro-6-[3-(3,3,3-trifluoro-2,2-dimethyl-propoxy)pyrazol-1-yl]pyridine-3-carboxylic acid (100 mg, 0.2667 mmol) and CDI (512 mg, 3.158 mmol) were combined in THF (582.0 μL) and the mixture was stirred at room temperature. Meanwhile, 1,3-dimethylpyrazole-4-sulfonyl chloride (62 mg, 0.3185 mmol) was combined with ammonia (in methanol) in a separate vial, instantly forming a white solid. After stirring for an additional 20 min, the volatiles were removed by evaporation, and 1 mL of dichloromethane was added to the solid residue, and was also evaporated. DBU (100 μL, 0.6687 mmol) was then added and the mixture stirred at 60° C. for 5 minutes, followed by addition of THF (1 mL) which was subsequently evaporated. The contents of the vial containing the CDI activated carboxylic acid in THF were then added to the vial containing the newly formed sulfonamide and DBU, and the reaction mixture was stirred for 4 hours at room temperature. The reaction mixture was diluted with 10 mL of ethyl acetate, and washed with 10 mL solution of citric acid (1 M). The aqueous layer was extracted with ethyl acetate (2×10 mL) and the combined organics were washed with brine, dried over sodium sulfate, and concentrated to give the product as white solid (137 mg, 99%) that was used in the next step without further purification. ESI-MS m/z calc. 520.09076, found 521.1 (M+1)+; Retention time: 0.68 minutes.

Step G: N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide

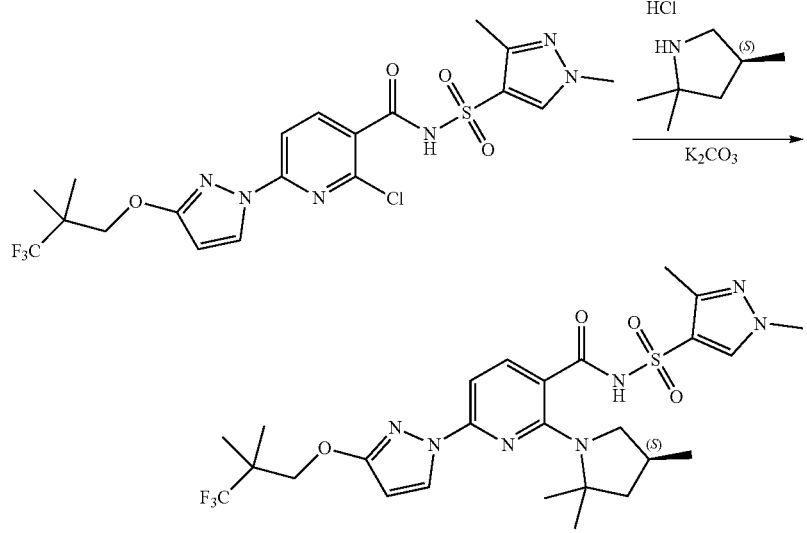

2-Chloro-N-(1,3-dimethylpyrazol-4-yl)sulfonyl-6-[3-(3,3,3-trifluoro-2,2-dimethyl-propoxy)pyrazol-1-yl]pyridine-3-carboxamide (137 mg, 0.2630 mmol), (4S)-2,2,4-trimethylpyrrolidine (Hydrochloride salt) (118 mg, 0.7884 mmol), and potassium carbonate (219 mg, 1.585 mmol) were combined in DMSO (685.0 µL) and the mixture was heated at 130° C. for 16 hours. The reaction was cooled to room temperature, and 1 mL of water was added. After stirring for 15 minutes, the contents of the vial were allowed to settle, and the liquid portion was removed via pipet and the remaining solids were dissolved with 20 mL of ethyl acetate and were washed with 1 M citric acid (15 mL). The layers were separated and the aqueous layer was extracted two additional times with 15 mL of ethyl acetate. The organics were combined, washed with brine, dried over sodium sulfate and concentrated. The resulting solid was further purified by silica gel chromatography eluting with a gradient of methanol in dichloromethane (0-10%) to give N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (72 mg, 41%) as a white solid. ESI-MS m/z calc. 597.2345, found 598.3 (M+1)+; Retention time: 2.1 minutes. $^1$H NMR (400 MHz, DMSO-$d_6$) δ 12.36 (s, 1H), 8.37 (s, 1H), 8.22 (d, J=2.8 Hz, 1H), 7.74 (d, J=8.2 Hz, 1H), 6.93 (d, J=8.2 Hz, 1H), 6.17 (d, J=2.8 Hz, 1H), 4.23 (s, 2H), 3.81 (s, 3H), 2.56 (d, J=10.4 Hz, 1H), 2.41 (t, J=8.7 Hz, 1H), 2.32 (s, 3H), 2.18 (dd, J=12.4, 6.1 Hz, 1H), 1.87 (dd, J=11.7, 5.5 Hz, 1H), 1.55 (d, J=11.2 Hz, 6H), 1.42 (t, J=12.0 Hz, 1H), 1.23 (s, 6H), 0.81 (d, J=6.2 Hz, 3H).

1. Preparation of Form A

The crystalline Form A was obtained as a result of the following synthesis. 2-chloro-N-(1,3-dimethylpyrazol-4-yl)sulfonyl-6-[3-(3,3,3-trifluoro-2,2-dimethyl-propoxy)pyrazol-1-yl]pyridine-3-carboxamide (108 g, 207.3 mmol), (4S)-2,2,4-trimethylpyrrolidine (Hydrochloride salt) (77.55 g, 518.2 mmol), was combined with $K_2CO_3$ (143.2 g, 1.036 mol) in DMSO (432.0 mL) and 1,2-diethoxyethane (108.0 mL) in a 1-L RB flask with a reflux condenser. The resulting suspension was heated at 120° C. and was stirred at temperature overnight. Then the reaction was diluted with DCM (1.080 L) and HCl (933.0 mL of 2 M, 1.866 mol) was slowly added. The liquid phases were separated, and the aqueous phase was extracted with DCM (540.0 mL). The organic phases were combined, washed with water (540.0 mL) (3 x), then dried with $Na_2SO_4$ to afford an amber solution. Silica gel (25 g) was added and then the drying agent/silica gel was filtered off. The filter-bed was washed with DCM (3×50-mL). The organic phases were combined and concentrated (40° C./40 torr) to afford crude N-(1,3-dimethylpyrazol-4-yl)sulfonyl-6-[3-(3,3,3-trifluoro-2,2-dimethyl-propoxy)pyrazol-1-yl]-2-[(4S)-2,2,4-trimethylpyrrolidin-1-yl]pyridine-3-carboxamide (198.6 g, 160% theory) as an off-white solid. The solid was diluted with MTBE (750 mL), warmed at 60° C. (external temperature), and mixed to a homogenous suspension. The suspension was cooled to 30° C. with stirring and the solid was collected by filtration, air-dried, and vacuum-dried to afford Compound 1 (111.1 g; 90%) as a fine, white powder.

The crystalline Form A was also obtained through the following procedure. A suspension of Compound I (150.0 g, 228.1 mmol) in iPrOH (480 mL) and water (120 mL) was heated at 82° C. to obtain a solution. The solution was cooled with a J-Kem controller at a cooling rate of 10° C./h. Once the temperature reached 74° C., the solution was seeded with a sample of Compound I in crystalline Form A. Crystallization occurred immediately. The suspension was cooled to 20° C. The solid was collected by filtration, washed with i-PrOH (2×75 mL), air-dried with suction, and vacuum-dried (55° C./300 torr/$N_2$ bleed) to afford Compound I, Form A (103.3 g) as a white powder. The sample was cooled to ~5° C., let stir for 1 h, and then the solid was collected by filtration (sintered glass/paper). The filter-cake was washed with i-PrOH (75 mL) (2 x), air-dried with suction, air-dried in a drying dish (120.6 g mostly dried), vacuum-dried (55° C./300 torr/$N_2$ bleed) for 4 h, and then RT overnight. Overnight drying afforded 118.3 g (87% yield) of a white powder.

2. Preparation of a Spray Dried Dispersion of Compound I

Compound I spray dried dispersion was prepared using Buchi Mini Spray Dryer B290. HPMCAS-HG (15.0 grams) was dissolved in 200 mL of MeOH/DCM (1/3), and Compound I (15.0 grams) was added and stirred for 30 minutes forming a clear solution. The resulting solution was spray dried under the following conditions resulting in a 50% Compound I/50% HPMCAS-HG spray dried dispersion (Yield: 70%, Solid load: 13%).

|  | Conditions |
| --- | --- |
| Inlet Temperature (° C.) | 80 |
| Outlet Temperature (° C.) | 39 |
| Nitrogen Pressure (PSI) | 95 |
| Aspirator (%) | 100 |
| Pump (%) | 25 |
| Rotameter (mm) | 60 |
| Filter Pressure (mBar) | −50 |
| Condenser Temperature (° C.) | −10 |

Powder X-Ray Diffraction

The powder x-ray diffraction measurements were performed using PANalytical's X-pert Pro diffractometer at room temperature, and atmospheric pressure, with copper radiation (1.54060 A). The incident beam optic was comprised of a variable divergence slit to ensure a constant illuminated length on the sample and on the diffracted beam side; a fast linear solid state detector was used with an active length of 2.12 degrees 2 theta measured in a scanning mode. The powder sample was packed on the indented area of a zero background silicon holder and spinning was performed to achieve better statistics. A symmetrical scan was measured from 4-40 degrees 2 theta with a step size of 0.017 degrees and a scan step time of 15.5s.

FIG. 1 shows the XRPD spectrum of Form A of Compound I.

Figure 2:
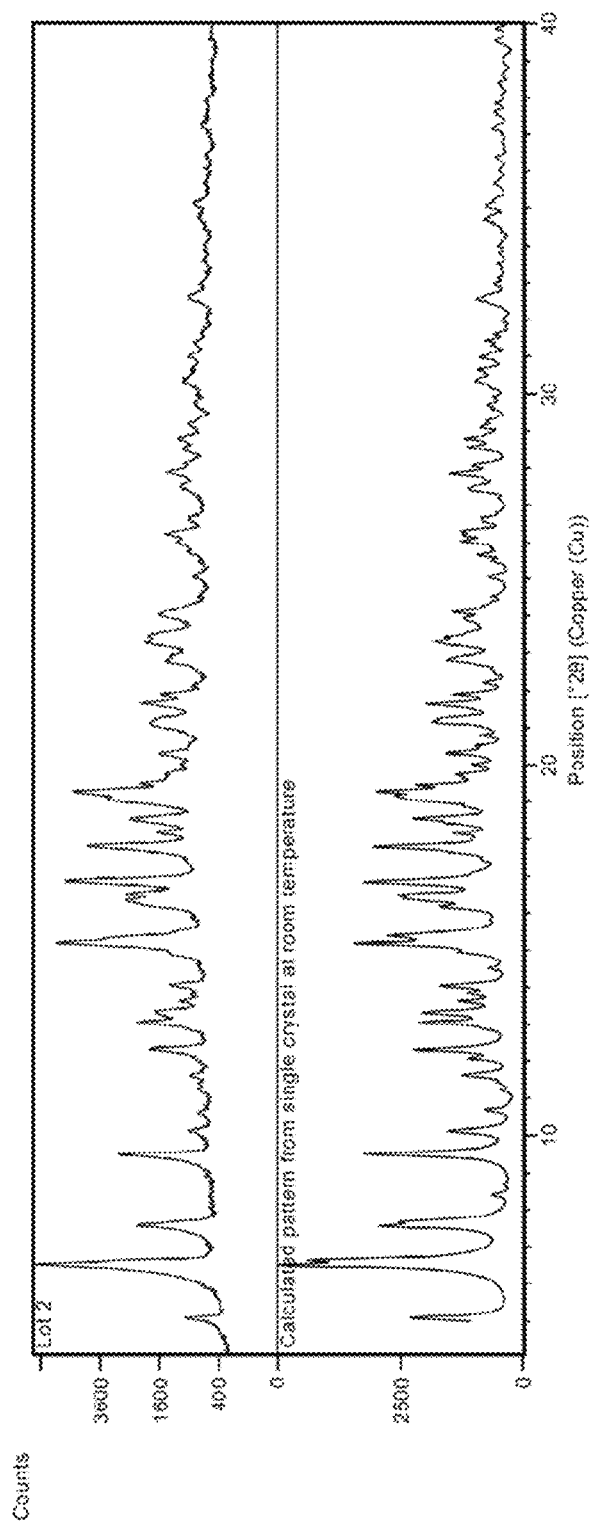
FIG. 2 is an experimental XRPD of Form A of Compound I (top) compared to a calculated XRD (bottom), which is calculated from the single crystal data.

FIG. 2 shows an experimental XRPD of Form A of Compound I (top) compared to a calculated XRD (bottom), which is calculated from the single crystal data. The single crystal structure of Form A has been elucidated. The crystal structure confirms the absolute configuration of the molecule, and the calculated XRPD patterns show good agreement with the experimental patterns. Form A of Compound I forms as an orthorhombic unit cell of P212121, a=15.74 b=22.86 c=26.59 (angstroms), α=β=γ=90, Z=12 V=9575 Flack=0.08. One of ordinary skill in the art would recognize that there may be variation in these crystal parameters depending, for example, on the temperature, pressure, or instrument to instrument variability.

Figure 3:
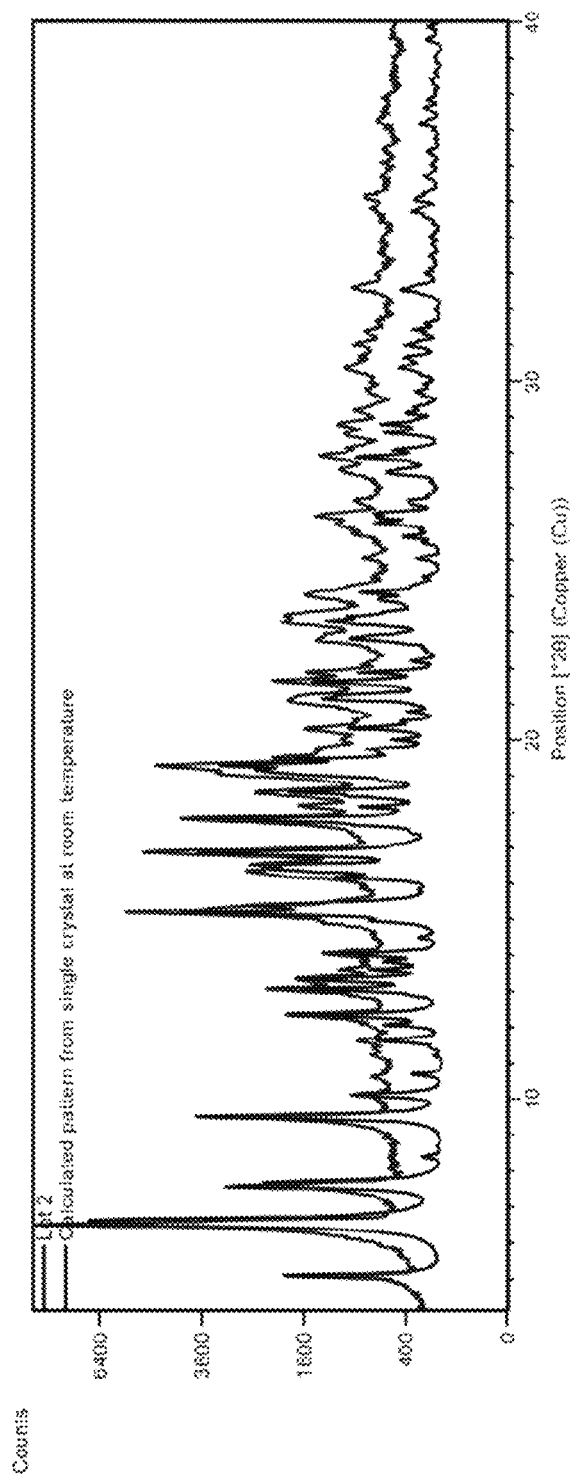
FIG. 3 is an overlay of the experimental and calculated XRPD of Form A of Compound I from FIG. 2.

FIG. 3 shows an overlay of the experimental and calculated XRPD of Form A of Compound I from FIG. 2.

Figure 4:
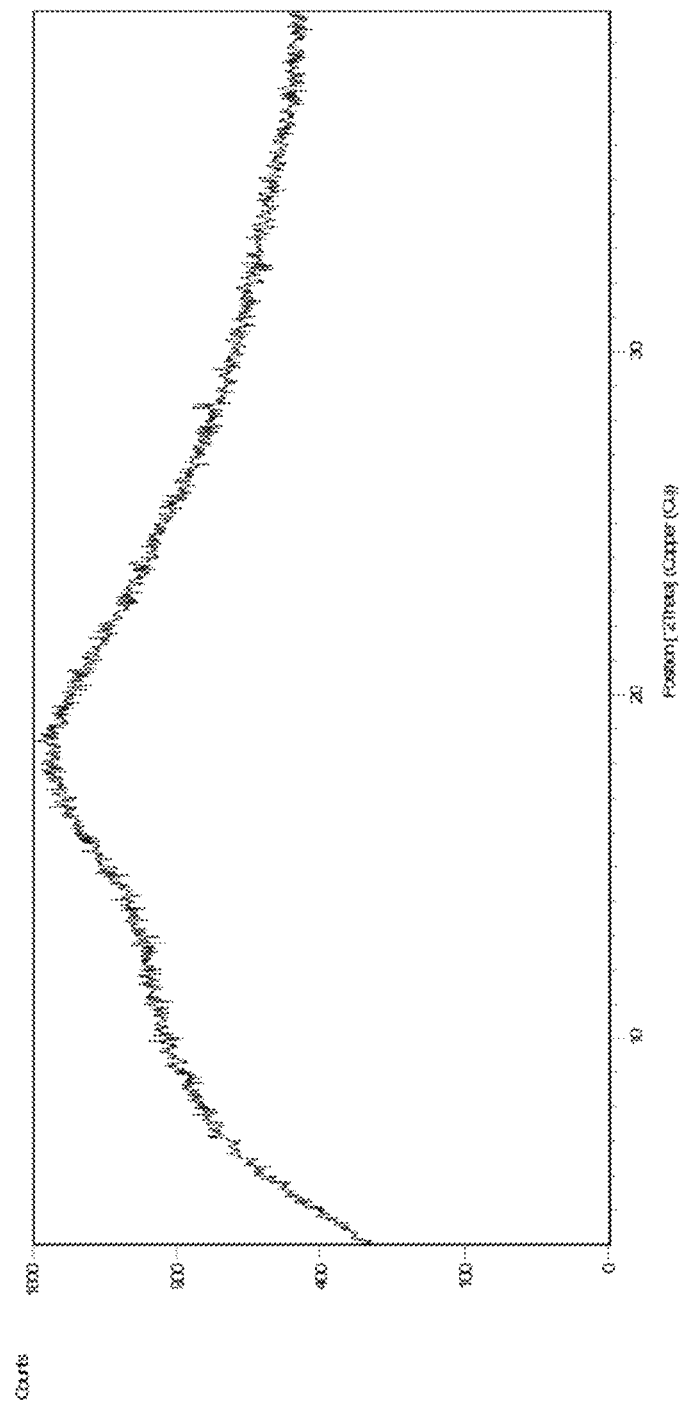
FIG. 4 is an XRPD of a spray dried dispersion of Compound I with HPMCAS-HG.

FIG. 4 shows the XRPD spectrum of amorphous Compound I prepared by spray dried dispersion (SDD) of 50% Compound I in HPMCAS-HG.

Modulated Differential Scanning Calorimetry (MDSC)

MDSC was used to determine the glass transition temperature of the amorphous material. MDSC was performed using TA Discovery DSC differential scanning calorimeter (TA Instruments, New Castle, DE). The instrument was calibrated with indium. Samples of approximately 1-3 mg were weighed into hermetic pans that were crimped using lids with one hole. The MDSC sample was scanned from −20° C. to 200° C. at a heating rate of 2° C./min with +/−1° C. of modulation within 1 minute. Data was collected and analyzed by TA Instruments Trios Software (TA Instruments, New Castle, DE).

Figure 5:
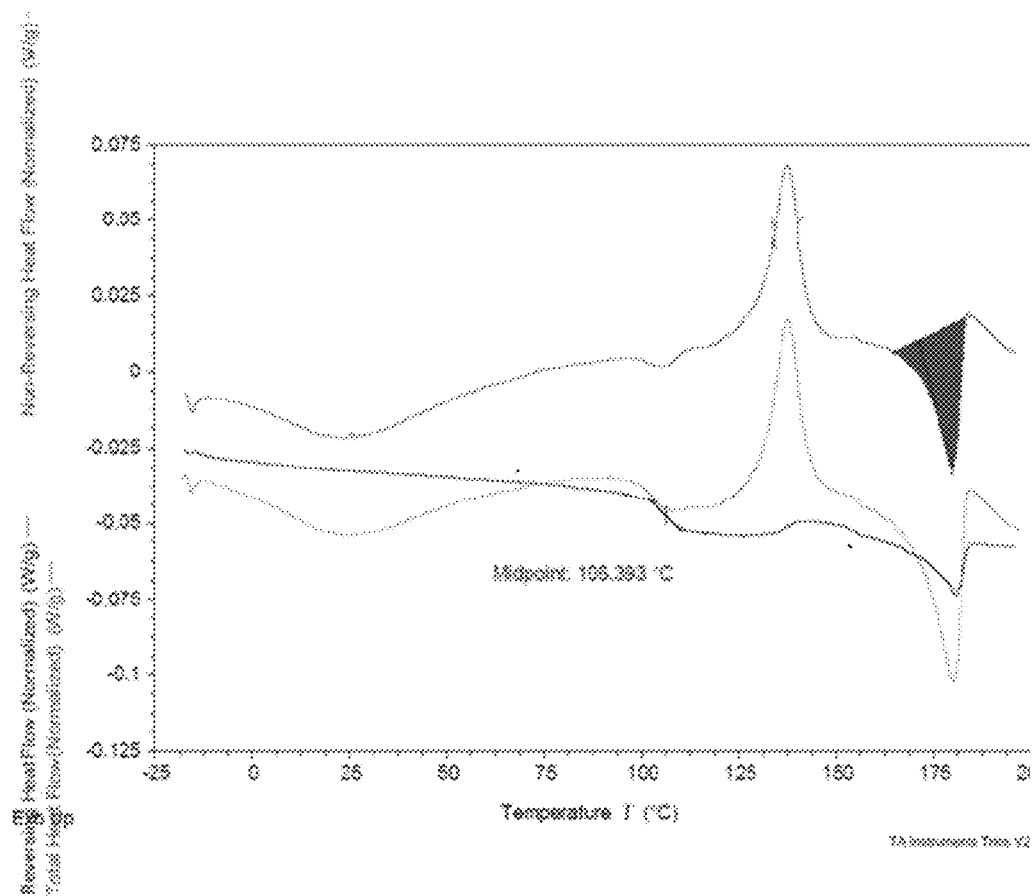
FIG. 5 is a MDSC spectrum of a SDD of 50% Compound I with HPMCAS-HG.
Figure 7:
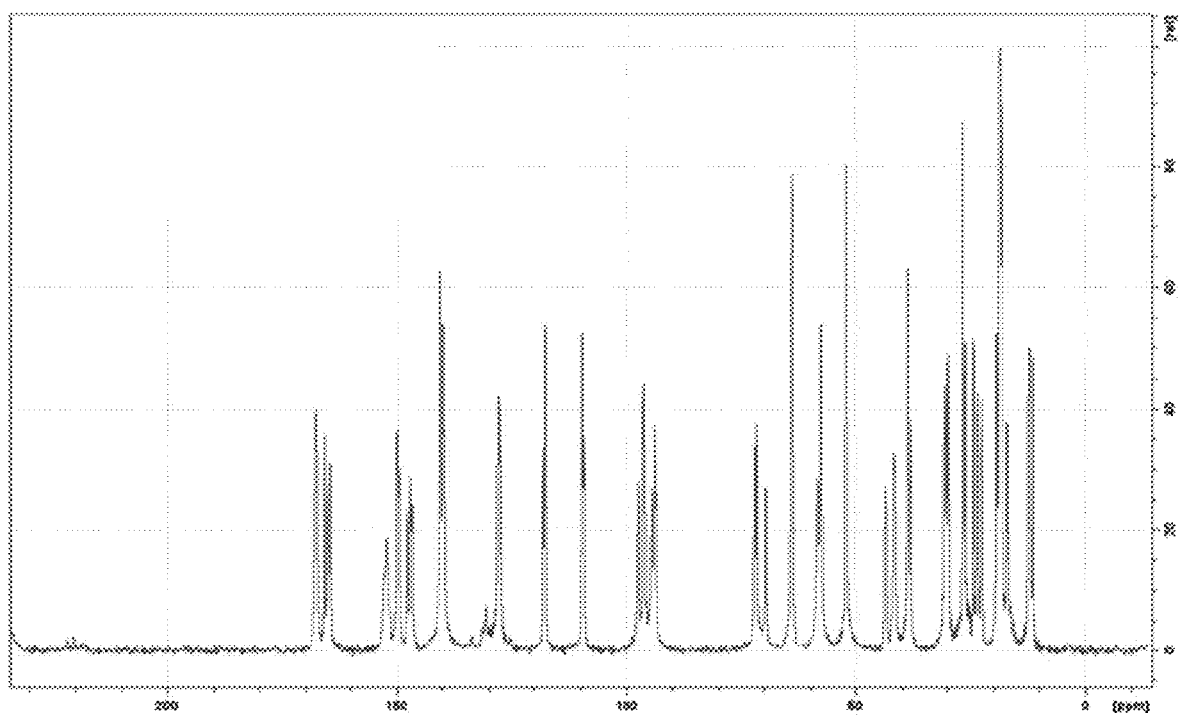
FIG. 7 is a solid state Carbon-13 NMR spectrum of Form A of Compound I, with MAS spinning at 12.5 kHz, referenced against adamantane 29.5 ppm, at 275 K. The spectrum was taken on a Bruker 400 MHz WB SSNMR; BH085908; asset V019431 (console), V015741 (magnet).
Figure 8:
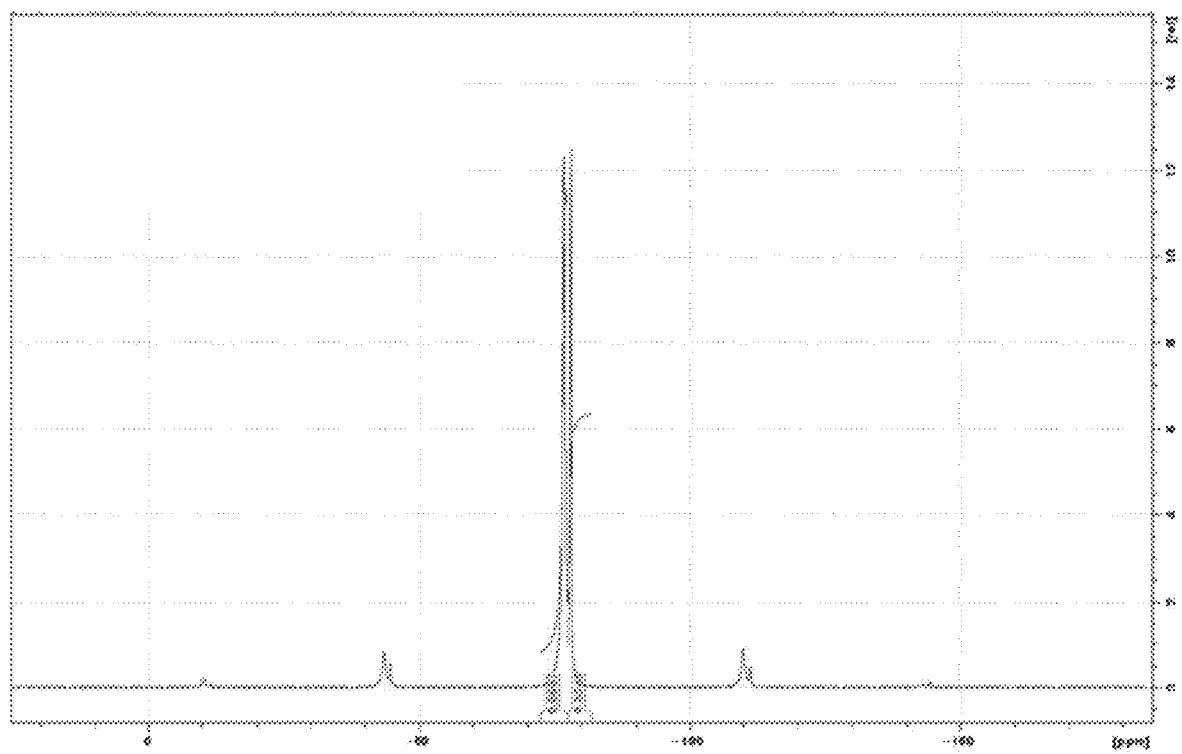
FIG. 8 is a solid state Fluorine-19 NMR spectrum of Form A of Compound I, with MAS spinning at 12.5 kHz, referenced against adamantane 29.5 ppm, at 275 K. The spectrum was taken on a Bruker 400 MHz WB SSNMR; BH085908; asset V019431 (console), V015741 (magnet).

FIG. 5 shows a MDSC spectrum of a spray dried dispersion (SDD) of 50% Compound I in HPMCAS-HG, and shows that the SDD has a midpoint temperature of about 106° C.

Example 2 Synthesis of Compound II: (R)-1-(2,2-Difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide

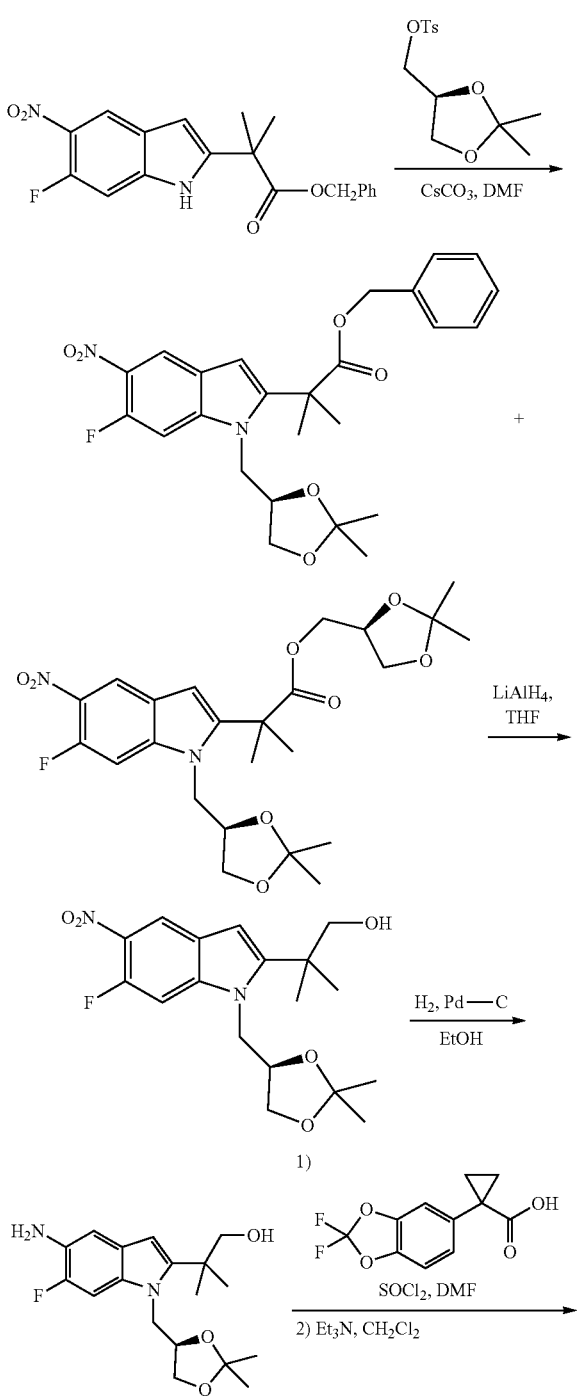

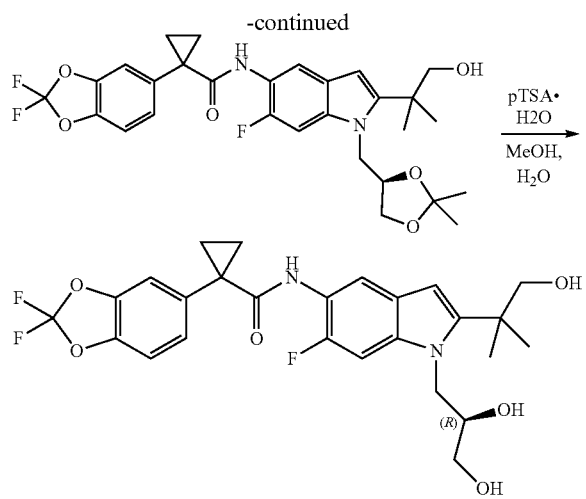

Step A: (R)-Benzyl 2-(1-((2,2-dimethyl-1,3-dioxo-lan-4-yl)methyl)-6-fluoro-5-nitro-1H-indol-2-yl)-2-methylpropanoate and ((S)-2,2-Dimethyl-1,3-dioxo-lan-4-yl)methyl 2-(1-(((R)-2,2-dimethyl-1,3-dioxolan-4-yl)methyl)-6-fluoro-5-nitro-1H-indol-2-yl)-2-methylpropanoate Cesium carbonate (8.23 g, 25.3 mmol) was added to a mixture of benzyl 2-(6-fluoro-5-nitro-1H-indol-2-yl)-2-methylpropanoate (3.0 g, 8.4 mmol) and (S)-(2,2-dimethyl-1,3-dioxolan-4-yl)methyl 4-methylbenzenesulfonate (7.23 g, 25.3 mmol) in DMF (17 mL). The reaction was stirred at 80° C. for 46 hours under a nitrogen atmosphere. The mixture was then partitioned between ethyl acetate and water. The aqueous layer was extracted with ethyl acetate. The combined ethyl acetate layers were washed with brine, dried over MgSO$_4$, filtered and concentrated. The crude product, a viscous brown oil which contains both of the products shown above, was taken directly to the next step without further purification. (R)-Benzyl 2-(1-((2,2-dimethyl-1,3-dioxolan-4-yl)methyl)-6-fluoro-5-nitro-1H-indol-2-yl)-2-methylpropanoate, ESI-MS m z calc. 470.2, found 471.5 (M+1)+. Retention time 2.20 minutes. ((S)-2,2-Dimethyl-1,3-dioxolan-4-yl)methyl 2-(1-(((R)-2,2-dimethyl-1,3-dioxolan-4-yl)methyl)-6-fluoro-5-nitro-1H-indol-2-yl)-2-methylpropanoate, ESI-MS m z calc. 494.5, found 495.7 (M+1)+. Retention time 2.01 minutes.

Step B: (R)-2-(1-((2,2-dimethyl-1,3-dioxolan-4-yl)methyl)-6-fluoro-5-nitro-1H-indol-2-yl)-2-methyl-propan-1-ol The crude reaction mixture obtained in step (A) was dissolved in THF (42 mL) and cooled in an ice-water bath. LiAlH$_4$ (16.8 mL of 1 M solution, 16.8 mmol) was added drop-wise. After the addition was complete, the mixture was stirred for an additional 5 minutes. The reaction was quenched by adding water (1 mL), 15% NaOH solution (1 mL) and then water (3 mL). The mixture was filtered over Celite, and the solids were washed with THF and ethyl acetate. The filtrate was concentrated and purified by column chromatography (30-60% ethyl acetate-hexanes) to obtain (R)-2-(1-((2,2-dimethyl-1,3-dioxolan-4-yl)methyl)-6-fluoro-5-nitro-1H-indol-2-yl)-2-methylpropan-1-ol as a brown oil (2.68 g, 87% over 2 steps). ESI-MS m z calc. 366.4, found 367.3 (M+1)+. Retention time 1.68 minutes.

$^1$H NMR (400 MHz, DMSO-d6) δ 8.34 (d, J=7.6 Hz, 1H), 7.65 (d, J=13.4 Hz, 1H), 6.57 (s, 1H), 4.94 (t, J=5.4 Hz, 1H), 4.64-4.60 (m, 1H), 4.52-4.42 (m, 2H), 4.16-4.14 (m, 1H), 3.76-3.74 (m, 1H), 3.63-3.53 (m, 2H), 1.42 (s, 3H), 1.38-1.36 (m, 6H) and 1.19 (s, 3H) ppm Step C: (R)-2-(5-amino-1-((2,2-dimethyl-1,3-dioxolan-4-yl)methyl)-6-fluoro-1H-indol-2-yl)-2-methyl-propan-1-ol (R)-2-(1-((2,2-dimethyl-1,3-dioxolan-4-yl)methyl)-6-fluoro-5-nitro-1H-indol-2-yl)-2-methylpropan-1-ol (2.5 g, 6.82 mmol) was dissolved in ethanol (70 mL) and the reaction was flushed with N$_2$. Then Pd—C (250 mg, 5% wt) was added. The reaction was flushed with nitrogen again and then stirred under H2 (atm). After 2.5 hours only partial conversion to the product was observed by LCMS. The reaction was filtered through Celite and concentrated. The residue was re-subjected to the conditions above. After 2 hours LCMS indicated complete conversion to product. The reaction mixture was filtered through Celite. The filtrate was concentrated to yield the product as a black solid (1.82 g, 79%). ESI-MS m z calc. 336.2, found 337.5 (M+1)+. Retention time 0.86 minutes. $^1$H NMR (400 MHz, DMSO-d6) δ 7.17 (d, J=12.6 Hz, 1H), 6.76 (d, J=9.0 Hz, 1H), 6.03 (s, 1H), 4.79-4.76 (m, 1H), 4.46 (s, 2H), 4.37-4.31 (m, 3H), 4.06 (dd, J=6.1, 8.3 Hz, 1H), 3.70-3.67 (m, 1H), 3.55-3.52 (m, 2H), 1.41 (s, 3H), 1.32 (s, 6H) and 1.21 (s, 3H) ppm.

Step D: (R)-1-(2,2-difluorobenzo[d][1,3]dioxol-5-yl)-N-(1-((2,2-dimethyl-1,3-dioxolan-4-yl)methyl)-6-fluoro-2-(1-hydroxy-2-methylpropan-2-yl)-1H-indol-5-yl)cyclopropanecarboxamide DMF (3 drops) was added to a stirring mixture of 1-(2,2-difluorobenzo[d][1,3]dioxol-5-yl)cyclopropanecarboxylic acid (1.87 g, 7.7 mmol) and thionyl chloride (1.30 mL, 17.9 mmol). After 1 hour a clear solution had formed. The solution was concentrated under vacuum and then toluene (3 mL) was added and the mixture was concentrated again. The toluene step was repeated once more and the residue was placed on high vacuum for 10 minutes. The acid chloride was then dissolved in dichloromethane (10 mL) and added to a mixture of (R)-2-(5-amino-1-((2,2-dimethyl-1,3-dioxolan-4-yl)methyl)-6-fluoro-1H-indol-2-yl)-2-methylpropan-1-ol (1.8 g, 5.4 mmol) and triethylamine (2.24 mL, 16.1 mmol) in dichloromethane (45 mL). The reaction was stirred at room temperature for 1 hour. The reaction was washed with 1N HCl solution, saturated NaHCO$_3$ solution and brine, dried over MgSO$_4$ and concentrated to yield the product as a black foamy solid (3 g, 100%). ESI-MS m z calc. 560.6, found 561.7 (M+1)+. Retention time 2.05 minutes. $^1$H NMR (400 MHz, DMSO-d6) δ 8.31 (s, 1H), 7.53 (s, 1H), 7.42-7.40 (m, 2H), 7.34-7.30 (m, 3H), 6.24 (s, 1H), 4.51-4.48 (m, 1H), 4.39-4.34 (m, 2H), 4.08 (dd, J=6.0, 8.3 Hz, 1H), 3.69 (t, J=7.6 Hz, 1H), 3.58-3.51 (m, 2H), 1.48-1.45 (m, 2H), 1.39 (s, 3H), 1.34-1.33 (m, 6H), 1.18 (s, 3H) and 1.14-1.12 (m, 2H) ppm Step E: (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide (R)-1-(2,2-difluorobenzo[d][1,3]dioxol-5-yl)-N-(1-((2,2-dimethyl-1,3-dioxolan-4-yl)methyl)-6-fluoro-2-(1-hydroxy-2-methylpropan-2-yl)-1H-indol-5-yl)cyclopropanecarboxamide (3.0 g, 5.4 mmol) was dissolved in methanol (52 mL). Water (5.2 mL) was added followed by p-TsOH·H$_2$O (204 mg, 1.1 mmol). The reaction was heated at 80° C. for 45 minutes. The solution was concentrated and then partitioned between ethyl acetate and saturated NaHCO$_3$ solution. The ethyl acetate layer was dried over MgSO$_4$ and concentrated. The residue was purified by column chromatography (50-100% ethyl acetate-hexanes) to yield the product as a cream colored foamy solid. (1.3 g, 47%, ee >98% by SFC). ESI-MS m z calc. 520.5, found 521.7 (M+1)+. Retention time 1.69 minutes. $^1$H NMR (400 MHz, DMSO-d6) δ 8.31 (s, 1H), 7.53 (s, 1H), 7.42-7.38 (m, 2H), 7.33-7.30 (m, 2H), 6.22 (s, 1H), 5.01 (d, J=5.2 Hz, 1H), 4.90 (t, J=5.5 Hz, 1H), 4.75 (t, J=5.8 Hz, 1H), 4.40 (dd, J=2.6, 15.1 Hz, 1H), 4.10 (dd, J=8.7, 15.1 Hz, 1H), 3.90 (s, 1H), 3.65-3.54 (m, 2H), 3.48-3.33 (m, 2H), 1.48-1.45 (m, 2H), 1.35 (s, 3H), 1.32 (s, 3H) and 1.14-1.11 (m, 2H) ppm.

Example 3 Synthesis of Compound III: N-(2,4-di-tert-butyl-5-hydroxyphenyl)-4-oxo-1,4-dihydroquinoline-3-carboxamide Part A: Preparation of 4-oxo-1,4-dihydroquinoline-3-carboxylic acid

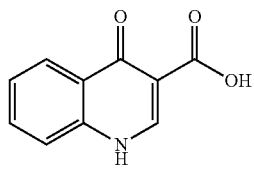 [SMILES: O=C(O)c1c[nH]c2ccccc2c1=O]

Step A: 2-Phenylaminomethylene-malonic acid diethyl ester

A mixture of aniline (25.6 g, 0.275 mol) and diethyl 2-(ethoxymethylene)malonate (62.4 g, 0.288 mol) was heated at 140-150° C. for 2 h. The mixture was cooled to room temperature and dried under reduced pressure to afford 2-phenylaminomethylene-malonic acid diethyl ester as a solid, which was used in the next step without further purification. $^1$H NMR (DMSO-d$_6$) δ 11.00 (d, 1H), 8.54 (d, J=13.6 Hz, 1H), 7.36-7.39 (m, 2H), 7.13-7.17 (m, 3H), 4.17-4.33 (m, 4H), 1.18-1.40 (m, 6H).

Step B: 4-Hydroxyquinoline-3-carboxylic acid ethyl ester

A 1 L three-necked flask fitted with a mechanical stirrer was charged with 2-phenylaminomethylene-malonic acid diethyl ester (26.3 g, 0.100 mol), polyphosphoric acid (270 g) and phosphoryl chloride (750 g). The mixture was heated to 70° C. and stirred for 4 h. The mixture was cooled to room temperature and filtered. The residue was treated with aqueous Na$_2$CO$_3$ solution, filtered, washed with water and dried. 4-Hydroxyquinoline-3-carboxylic acid ethyl ester was obtained as a pale brown solid (15.2 g, 70%). The crude product was used in next step without further purification.

Step C: 4-Oxo-1,4-dihydroquinoline-3-carboxylic acid

4-Hydroxyquinoline-3-carboxylic acid ethyl ester (15 g, 69 mmol) was suspended in sodium hydroxide solution (2N, 150 mL) and stirred for 2 h at reflux. After cooling, the mixture was filtered, and the filtrate was acidified to pH 4 with 2N HCl. The resulting precipitate was collected via filtration, washed with water and dried under vacuum to give 4-oxo-1,4-dihydroquinoline-3-carboxylic acid as a pale white solid (10.5 g, 92%). $^1$H NMR (DMSO-d$_6$) δ 15.34 (s, 1H), 13.42 (s, 1H), 8.89 (s, 1H), 8.28 (d, J=8.0 Hz, 1H), 7.88 (m, 1H), 7.81 (d, J=8.4 Hz, 1H), 7.60 (m, 1H).

Part B: N-(2,4-di-tert-butyl-5-hydroxyphenyl)-4-oxo-1,4-dihydroquinoline-3-carboxamide

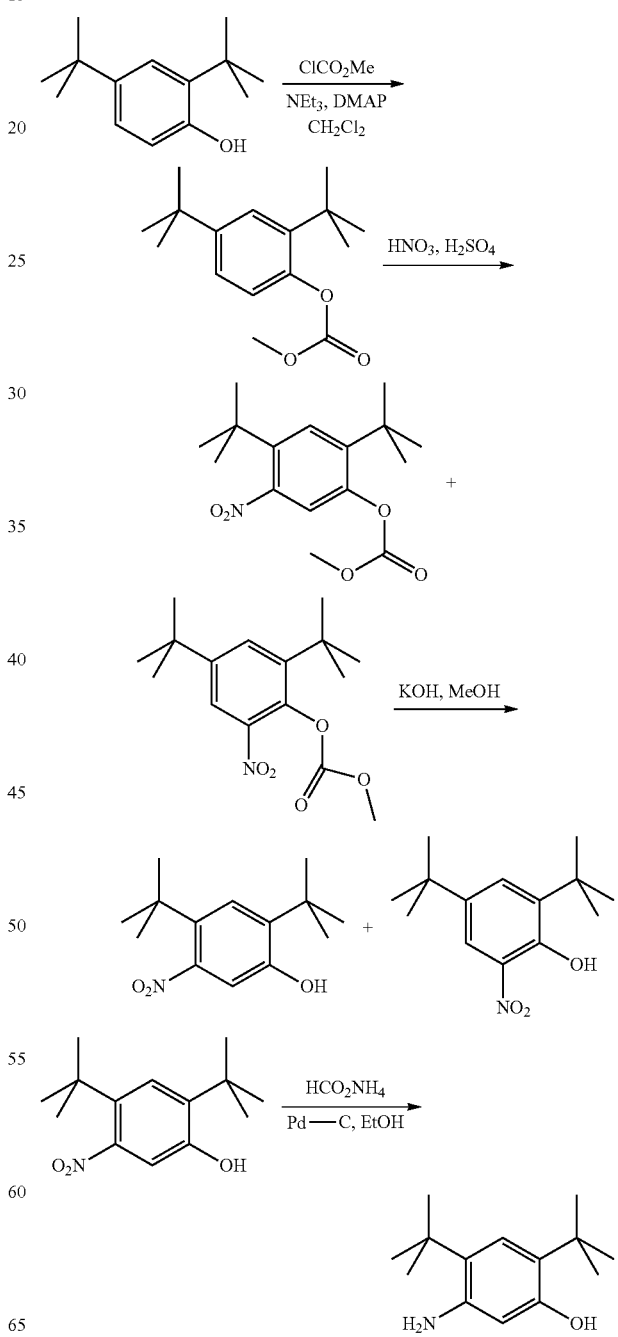

Step A: Carbonic acid 2,4-di-tert-butyl-phenyl ester methyl ester

Methyl chloroformate (58 mL, 750 mmol) was added dropwise to a solution of 2,4-di-tert-butyl-phenol (103.2 g, 500 mmol), Et₃N (139 mL, 1000 mmol) and DMAP (3.05 g, 25 mmol) in dichloromethane (400 mL) cooled in an ice-water bath to 0° C. The mixture was allowed to warm to room temperature while stirring overnight, then filtered through silica gel (approx. 1 L) using 10% ethyl acetate-hexanes (~4 L) as the eluent. The combined filtrates were concentrated to yield carbonic acid 2,4-di-tert-butyl-phenyl ester methyl ester as a yellow oil (132 g, quant.). ¹H NMR (400 MHz, DMSO-d₆) δ 7.35 (d, J=2.4 Hz, 1H), 7.29 (dd, J=8.5, 2.4 Hz, 1H), 7.06 (d, J=8.4 Hz, 1H), 3.85 (s, 3H), 1.30 (s, 9H), 1.29 (s, 9H).

Step B: Carbonic Acid 2,4-di-tert-butyl-5-nitro-phenyl ester methyl ester and Carbonic acid 2,4-di-tert-butyl-6-nitro-phenyl ester methyl ester To a stirring mixture of carbonic acid 2,4-di-tert-butyl-phenyl ester methyl ester (4.76 g, 180 mmol) in conc. sulfuric acid (2 mL), cooled in an ice-water bath, was added a cooled mixture of sulfuric acid (2 mL) and nitric acid (2 mL). The addition was done slowly so that the reaction temperature did not exceed 50° C. The reaction was allowed to stir for 2 h while warming to room temperature. The reaction mixture was then added to ice-water and extracted into diethyl ether. The ether layer was dried (MgSO₄), concentrated and purified by column chromatography (0-10% ethyl acetate-hexanes) to yield a mixture of carbonic acid 2,4-di-tert-butyl-5-nitro-phenyl ester methyl ester and carbonic acid 2,4-di-tert-butyl-6-nitro-phenyl ester methyl ester as a pale yellow solid (4.28 g), which was used directly in the next step.

Step C: 2,4-Di-tert-butyl-5-nitro-phenol and 2,4-Di-tert-butyl-6-nitro-phenol The mixture of carbonic acid 2,4-di-tert-butyl-5-nitro-phenyl ester methyl ester and carbonic acid 2,4-di-tert-butyl-6-nitro-phenyl ester methyl ester (4.2 g, 14.0 mmol) was dissolved in MeOH (65 mL) before KOH (2.0 g, 36 mmol) was added. The mixture was stirred at room temperature for 2 h. The reaction mixture was then made acidic (pH 2-3) by adding conc. HCl and partitioned between water and diethyl ether. The ether layer was dried (MgSO₄), concentrated and purified by column chromatography (0-5% ethyl acetate-hexanes) to provide 2,4-di-tert-butyl-5-nitro-phenol (1.31 g, 29% over 2 steps) and 2,4-di-tert-butyl-6-nitro-phenol. 2,4-Di-tert-butyl-5-nitro-phenol: ¹H NMR (400 MHz, DMSO-d₆) δ 10.14 (s, 1H, OH), 7.34 (s, 1H), 6.83 (s, 1H), 1.36 (s, 9H), 1.30 (s, 9H). 2,4-Di-tert-butyl-6-nitro-phenol: ¹H NMR (400 MHz, CDCl₃) δ 11.48 (s, 1H), 7.98 (d, J=2.5 Hz, 1H), 7.66 (d, J=2.4 Hz, 1H), 1.47 (s, 9H), 1.34 (s, 9H).

Step D: 5-Amino-2,4-di-tert-butyl-phenol

To a refluxing solution of 2,4-di-tert-butyl-5-nitro-phenol (1.86 g, 7.40 mmol) and ammonium formate (1.86 g) in ethanol (75 mL) was added Pd-5% wt. on activated carbon (900 mg). The reaction mixture was stirred at reflux for 2 h, cooled to room temperature and filtered through Celite. The Celite was washed with methanol and the combined filtrates were concentrated to yield 5-amino-2,4-di-tert-butyl-phenol as a grey solid (1.66 g, quant.). ¹H NMR (400 MHz, DMSO-d₆) δ 8.64 (s, 1H, OH), 6.84 (s, 1H), 6.08 (s, 1H), 4.39 (s, 2H, NH₂), 1.27 (m, 18H); HPLC ret. time 2.72 min, 10-99% CH₃CN, 5 min run; ESI-MS 222.4 m/z [M+H]⁺.

Step E: N-(5-hydroxy-2,4-di-tert-butyl-phenyl)-4-oxo-1H-quinoline-3-carboxamide

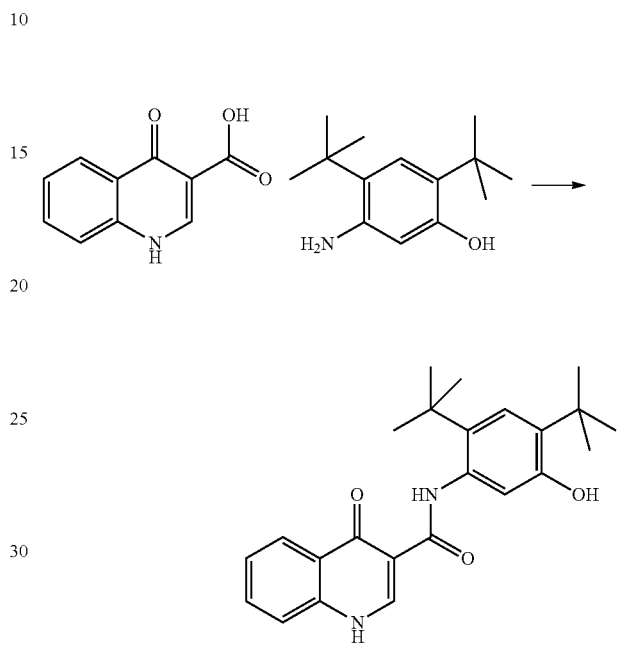

To a suspension of 4-oxo-1,4-dihydroquinolin-3-carboxylic acid (35.5 g, 188 mmol) and HBTU (85.7 g, 226 mmol) in DMF (280 mL) was added Et₃N (63.0 mL, 451 mmol) at ambient temperature. The mixture became homogeneous and was allowed to stir for 10 min before 5-amino-2,4-di-tert-butyl-phenol (50.0 g, 226 mmol) was added in small portions. The mixture was allowed to stir overnight at ambient temperature. The mixture became heterogeneous over the course of the reaction. After all of the acid was consumed (LC-MS analysis, MH+ 190, 1.71 min), the solvent was removed in vacuo. EtOH was added to the orange solid material to produce a slurry. The mixture was stirred on a rotovap (bath temperature 65° C.) for 15 min without placing the system under vacuum. The mixture was filtered and the captured solid was washed with hexanes to provide a white solid that was the EtOH crystallate. Et₂O was added to the solid obtained above until a slurry was formed. The mixture was stirred on a rotovap (bath temperature 25° C.) for 15 min without placing the system under vacuum. The mixture was filtered and the solid captured. This procedure was performed a total of five times. The solid obtained after the fifth precipitation was placed under vacuum overnight to provide N-(5-hydroxy-2,4-di-tert-butyl-phenyl)-4-oxo-1H-quinoline-3-carboxamide as a white powdery solid (38 g, 52%). HPLC ret. time 3.45 min, 10-99% CH₃CN, 5 min run; ¹H NMR (400 MHz, DMSO-d₆) δ 12.88 (s, 1H), 11.83 (s, 1H), 9.20 (s, 1H), 8.87 (s, 1H), 8.33 (dd, J=8.2, 1.0 Hz, 1H), 7.83-7.79 (m, 1H), 7.76 (d, J=7.7 Hz, 1H), 7.54-7.50 (m, 1H), 7.17 (s, 1H), 7.10 (s, 1H), 1.38 (s, 9H), 1.37 (s, 9H); ESI-MS m/z calc'd 392.21; found 393.3 [M+H]⁺.

Example 4: Synthesis of N-(2-(tert-Butyl)-4-(tert-butyl-d,)-5-hydroxyphenyl)-4-oxo-1,4-dihydroquinoline-3-carboxamide (Compound III-d)

Step 1. 2-(tert-Butyl-d9)-4-(tert-butyl)-6-d-phenol

To a solution of 4-tert-butyl phenol (3.43 g, 22.7 mmol) and tert-butyl alcohol-d10 (3.00 mL, 31.8 mmol, 98 atom % D, Cambridge Isotope Laboratories, Inc.) in dichloromethane (40.0 mL) was added $D_2SO_4$ (1.50 mL, 99.5 atom % D, Sigma-Aldrich). The reaction was stirred at room temperature for 15 hours then was diluted with water and extracted with dichloromethane (3×100 mL). The organic layers were combined, washed with saturated $NaHCO_3$, dried ($Na_2SO_4$), filtered, and concentrated in vacuo. The resulting oil was purified by column chromatography ($SiO_2$, 0-15% ethyl acetate/heptanes) to afford 2-(tert-Butyl-d9)-4-(tert-butyl)-6-d-phenol (4.04 g, 83% yield) as a clear oil. $^1$HNMR ($d_6$-DMSO, 400 MHz) δ 9.04 (s, 1H), 7.12 (d, J=2.4 Hz, 1H), 6.98 (dd, J=3.8, 2.5 Hz, 1H), 6.67 (d, J=8.3 Hz, 0.3H), 1.22 (s, 10H).

Step 2. 2-(tert-Butyl-$d_9$)-4-(tert-butyl)-6-d-phenyl methyl carbonate

To a solution of 2-(tert-Butyl-$d_9$)-4-(tert-butyl)-6-d-phenol (4.04 g, 18.8 mmol), triethylamine (5.24 mL, 37.6 mmol) and N,N-dimethylaminopyridine (115 mg, 0.940 mmol) in $CH_2Cl_2$ (40.0 mL) at 0° C. was added methyl chloroformate (2.17 mL, 28.2 mmol). The reaction was stirred at room temperature for 15 hours and additional trimethylamine (1.30 mL, 9.33 mmol) and methyl chloroformate (0.550 mL, 7.15 mmol) were added. After stirring for an additional 1 hour the reaction was diluted with 10% ethyl acetate/heptanes and filtered through a silica plug. The silica plug was then rinsed with additional 10% ethyl acetate/heptanes. The filtrate was combined and concentrated in vacuo to provide 2-(tert-Butyl-$d_9$)-4-(tert-butyl)-6-d-phenyl methyl carbonate (4.69 g, 91% yield) as a light yellow oil which was carried forward without purification. $^1$H NMR ($d_6$-DMSO, 400 MHz) δ 7.33 (d, J=2.4 Hz, 1H), 7.30-7.20 (m, 1H), 7.06 (d, J=8.5 Hz, 0.3H), 3.84 (d, J=0.7 Hz, 3H), 1.28 (s, 9H).

Step 3. 2-(tert-Butyl-$d_9$)-4-(tert-butyl)-6-d-5-nitro-phenol

To a solution of 2-(tert-Butyl-$d_9$)-4-(tert-butyl)-6-d-phenyl methyl carbonate (4.69 g, 17.2 mmol) in sulfuric acid (2.00 mL) at 0° C. was added a 1:1 mixture of sulfuric acid and nitric acid (4.00 mL) dropwise. The reaction was then stirred at room temperature for two hours then slowly added to ice water with vigorous stirring. The resulting slurry was extracted with ethyl acetate (3×100 mL) and the combined organic layers were dried ($Na_2SO_4$), filtered, and concentrated to afford an amber oil containing a mixture of regio-isomers. This crude oil was then taken up in MeOH (100 mL) and KOH (3.50 g) was added. The reaction was stirred at room temperature for 2 hours then was acidified to pH=2 with concentrated HCl. The resulting solution was extracted with diethyl ether (3×100 mL), dried ($MgSO_4$), filtered, and concentrated. The residue was then purified via column chromatography ($SiO_2$, 0-5% ethyl acetate/heptanes) to afford 2-(tert-Butyl-$d_9$)-4-(tert-butyl)-6-d-5-nitro-phenol (1.33 g, 30%) as a light yellow solid. MS (ESI) 260.2 [(M−H)$^-$].

Step 4. 5-Amino-2-(tert-butyl-$d_9$)-4-(tert-butyl)-6-d-phenol

A solution of 2-(tert-Butyl-$d_9$)-4-(tert-butyl)-6-d-5-nitro-phenol (1.33 g, 5.11 mmol) and ammonium formate (1.29 g, 20.4 mmol) in ethanol (60.0 mL) was heated to reflux. At this time, 10% Pd/C (650 mg, 50% wet) was added in small portions and the reaction continued to stir at reflux for two hours. The reaction was then cooled to room temperature, diluted with THF, filtered through Celite® and concentrated in vacuo to afford 5-Amino-2-(tert-butyl-d9)-4-(tert-butyl)-6-d-phenol (1.19 g, 100%) as a pink solid. MS (ESI) 232.3 [(M+H)$^+$].

Step 5. 5-Amino-2-(tert-butyl-$d_9$)-4-(tert-butyl)-phenol

5-Amino-2-(tert-butyl-$d_9$)-4-(tert-butyl)-6-d phenol (298 mg, 1.29 mmol) was dissolved in 5M HCl in 2-propanol (20 mL) and the reaction was stirred at room temperature for 15 hours. The reaction was then concentrated in vacuo and taken back up in 5M HCl in 2-propanol (20 mL). After stirring for an additional 15 hours at room temperature, the reaction was concentrated in vacuo and diluted with saturated aqueous sodium bicarbonate (100 mL). The resulting aqueous solution was extracted with dichloromethane (3×50 mL). The organic layers were combined, dried ($Na_2SO_4$), filtered and concentrated in vacuo to afford 5-Amino-2-(tert-butyl-$d_9$)-4-(tert-butyl)-phenol (240 mg, 81%) as a pink solid. $^1$H NMR ($d_6$-DMSO, 400 MHz) δ 8.62 (s, 1H), 6.83 (s, 1H), 6.08 (s, 1H), 1.27 (s, 9H).

Step 6. N-(2-(tert-Butyl)-4-(tert-butyl-$d_9$)-5-hydroxyphenyl)-4-oxo-1,4-dihydroquinoline-3-carboxamide (Compound III-d)

To a solution of 5-Amino-2-(tert-butyl-$d_9$)-4-(tert-butyl)-phenol (240 mg, 1.04 mmol), 4-oxo-1,4-dihydroquinoline-3-carboxylic acid (purchased from Matrix Scientific, 99 mg, 0.521 mmol) and N,N-diisopropylethylamine (181 μl, 1.04 mmol) in DMF (6.00 mL) was added HATU (198 mg, 0.521 mmol). The reaction was stirred at room temperature for three hours then was diluted with saturated $NaHCO_3$ and extracted with ethyl acetate (3×50 mL). The combined organic extracts were washed with water (3×20 mL), dried ($Na_2SO_4$), filtered, and concentrated in vacuo. The resulting residue was purified via column chromatography ($SiO_2$, 0-70% ethyl acetate/heptanes) to afford N-(2-(tert-Butyl)-4-(tert-butyl-$d_9$)-5-hydroxyphenyl)-4-oxo-1,4-dihydroquinoline-3-carboxamide (Compound III-d) (80 mg, 38% Yield) as a white solid. $^1$H NMR ($d_6$-DMSO, 400 MHz) δ 12.88 (s, 1H), 11.81 (s, 1H), 9.19 (s, 1H), 8.86 (s, 1H), 8.32 (dd, J=8.1, 1.4 Hz, 1H), 7.86-7.77 (m, 1H), 7.75 (d, J=8.2 Hz, 1H), 7.51 (s, 1H), 7.15 (s, 1H), 7.09 (s, 1H) 1.37 (s, 9H); MS (ESI) 402.3 [(M+H)+].

Example 5: Synthesis of Compound IV: 3-(6-(1-(2,2-difluorobenzo[d][1,3]dioxol-5-yl) cyclopropanecarboxamido)-3-methylpyridin-2-yl)benzoic acid Compound IV may be prepared by coupling an acid chloride moiety with an amine moiety according to Schemes IV-A through IV-D.

Scheme IV-A. Synthesis of the acid chloride moiety.

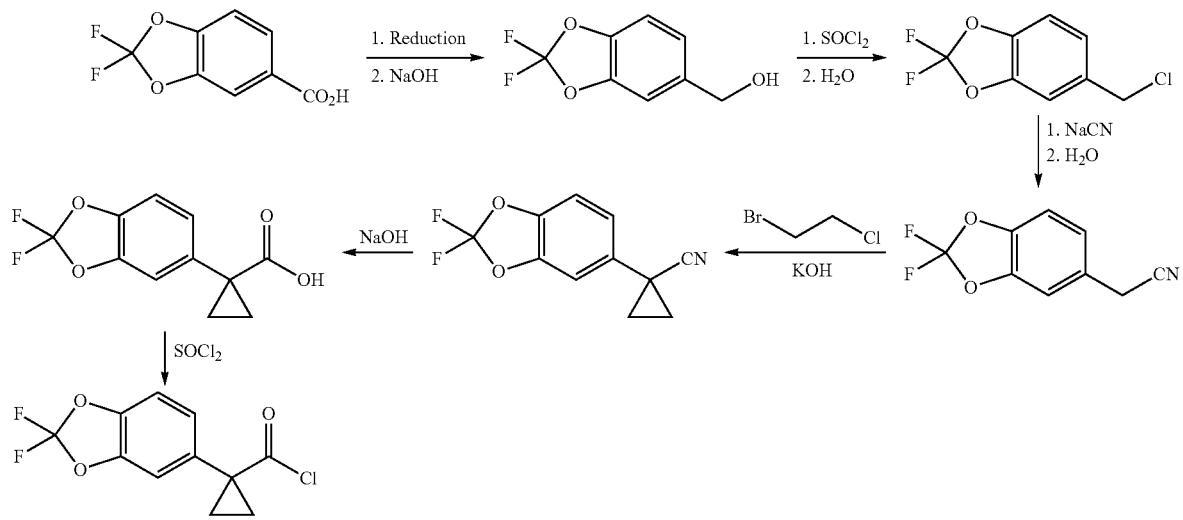

Scheme IV-A depicts the preparation of 1-(2,2-difluorobenzo[d][1,3]dioxol-5-yl)cyclopropanecarbonyl chloride, which is used in Scheme IV-C to make the amide linkage of Compound IV.

The starting material, 2,2-difluorobenzo[d][1,3]dioxole-5-carboxylic acid, is commercially available from Saltigo (an affiliate of the Lanxess Corporation). Reduction of the carboxylic acid moiety in 2,2-difluorobenzo[d][1,3]dioxole-5-carboxylic acid to the primary alcohol, followed by conversion to the corresponding chloride using thionyl chloride (SOCl$_2$), provides 5-(chloromethyl)-2,2-difluorobenzo[d][1,3]dioxole, which is subsequently converted to 2-(2,2-difluorobenzo[d][1,3]dioxol-5-yl)acetonitrile using sodium cyanide. Treatment of 2-(2,2-difluorobenzo[d][1,3]dioxol-5-yl)acetonitrile with base and 1-bromo-2-chloroethane provides 1-(2,2-difluorobenzo[d][1,3]dioxol-5-yl)cyclopropanecarbonitrile. The nitrile moiety in 1-(2,2-difluorobenzo[d][1,3]dioxol-5-yl)cyclopropanecarbonitrile is converted to a carboxylic acid using base to give 1-(2,2-difluorobenzo[d][1,3]dioxol-5-yl)cyclopropanecarboxylic acid, which is converted to the desired acid chloride using thionyl chloride.

Scheme IV-B. Alternative synthesis of the acid chloride moiety.

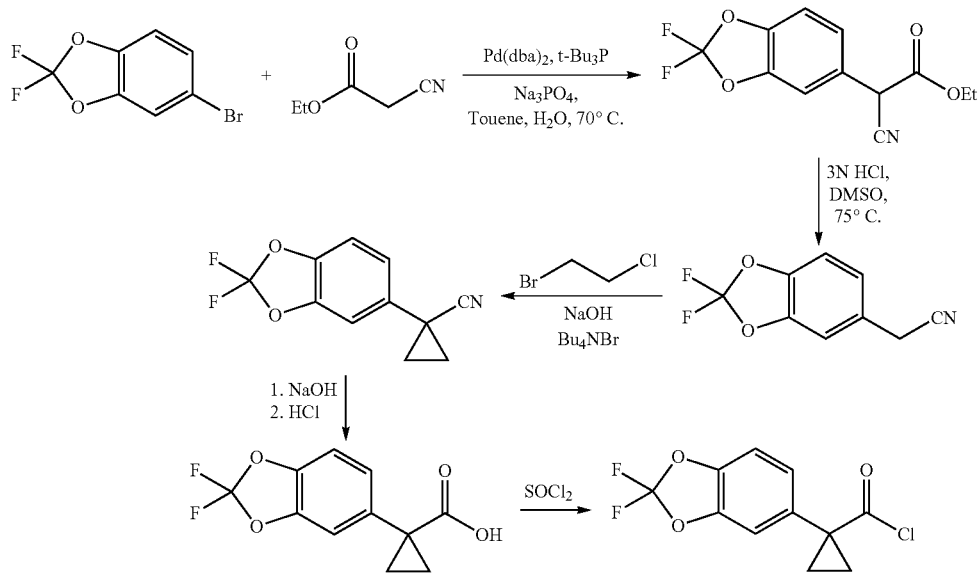

Scheme IV-B depicts an alternative synthesis of the requisite acid chloride. 5-bromomethyl-2,2-difluoro-1,3-benzodioxole is coupled with ethyl cyanoacetate in the presence of a palladium catalyst to form the corresponding alpha cyano ethyl ester. Saponification of the ester moiety to the carboxylic acid gives the cyanoethyl Compound IV. Alkylation of the cyanoethyl compound with 1-bromo-2-chloro ethane in the presence of base gives the cyanocyclopropyl compound. Treatment of the cyanocyclopropyl compound with base gives the carboxylate salt, which is converted to the carboxylic acid by treatment with acid. Conversion of the carboxylic acid to the acid chloride is then accomplished using a chlorinating agent such as thionyl chloride or the like.

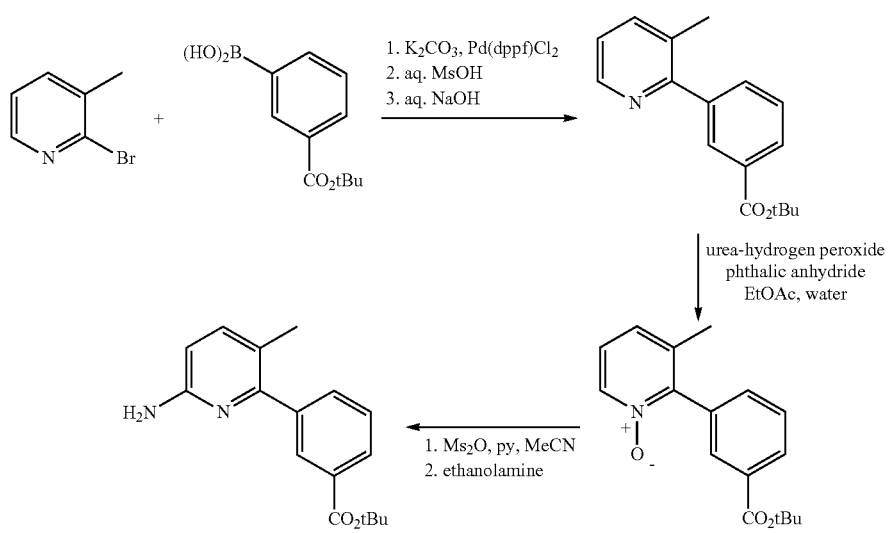

Scheme IV-C. Synthesis of the amine moiety.

Scheme IV-C depicts the preparation of the requisite tert-butyl 3-(6-amino-3-methylpyridin-2-yl)benzoate, which is coupled with 1-(2,2-difluorobenzo[d][1,3]dioxol-5-yl)cyclopropanecarbonyl chloride in Scheme IV-C to give Compound IV. Palladium-catalyzed coupling of 2-bromo-3-methylpyridine with 3-(tert-butoxycarbonyl)phenylboronic acid gives tert-butyl 3-(3-methylpyridin-2-yl)benzoate, which is subsequently converted to the desired compound.

Scheme IV-D. Formation of an acid salt of 3-(6-(1-(2,2-difluorobenzo[d][1,3]dioxol-5-yl) cyclopropanecarboxamido)-3-methylpyridin-2-yl)benzoic acid.

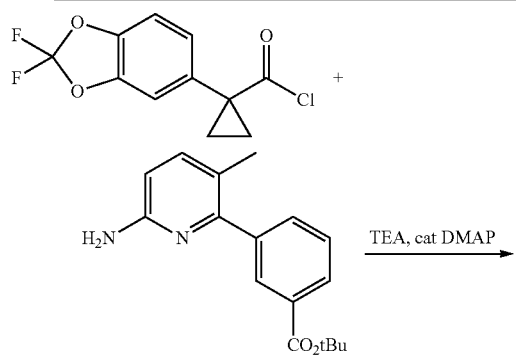

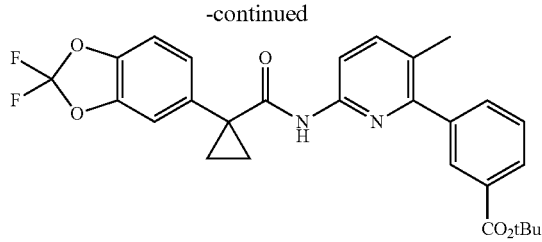

Scheme IV-D depicts the coupling of 1-(2,2-difluorobenzo[d][1,3]dioxol-5-yl)cyclopropanecarbonyl chloride with tert-butyl 3-(6-amino-3-methylpyridin-2-yl)benzoate using triethyl amine and 4-dimethylaminopyridine to initially provide the tert-butyl ester of Compound IV.

Example 6: Assays for Detecting and Measuring F508del-CFTR Modulator Properties of Compounds Membrane Potential Optical Methods for Assaying Properties of F508del-CFTR Modulators An optical assay was employed to measure changes in membrane potential to determine the CFTR modulator properties of compounds. The assay utilized fluorescent voltage sensing dyes to measure changes in membrane potential using a fluorescent plate reader (e.g., FLIPR III, Molecular Devices, Inc.) as a readout for increase in functional F508del in NIH 3T3 cells. The driving force for the response was the creation of a chloride ion gradient in conjunction with channel activation and concurrent with compound treatment by a single liquid addition step after the cells had previously been loaded with a voltage sensing dye.

Assay Procedure

NIH3T3 mouse fibroblasts stably expressing F508del were used for optical measurements of membrane potential. The cells were maintained at 37° C. in 5% $CO_2$ and 90% humidity in Dulbecco's modified Eagle's medium supplemented with 2 mM glutamine, 10% fetal bovine serum, 1×NEAA, P-ME, 1× pen/strep, and 25 mM HEPES in 175 $cm^2$ culture flasks. For all optical assays, the cells were seeded at 12,000 cells/well in 384-well matrigel-coated plates. For the correction assay, the cells were cultured at 37° C. for 18-24 hours and loaded with a voltage sensing dye. The cells were then activated and treated with Compound I. After 18-24 hours, fluorescence from the voltage sensing dye in the cells was measured to assess changes in the membrane potential as a read out for increase in functional F508del CFTR in the NIH3T3 cells.

Using this method, Compound I had an $EC_{50}$ of less than 3 µM and a % Efficacy of ≥100% relative to Compound II.

Ussing Chamber Assay

Ussing chamber experiments were performed on polarized airway epithelial cells expressing F508del to further characterize the F508del modulators identified in the optical assay above. Non-CF and CF airway epithelia were isolated from bronchial tissue, cultured using methods well known in the art, and plated onto Costar® Snapwell™ filters that were precoated with NIH3T3-conditioned media. After four days the apical media was removed and the cells were grown at an air liquid interface for >14 days prior to use. This resulted in a monolayer of fully differentiated columnar cells that were ciliated, features that are characteristic of airway epithelia. Non-CF human bronchial epithelial (HBE) cells were isolated from non-smokers that did not have any known lung disease. CF-HBE cells were isolated from patients homozygous for F508del (F508del/F508del-HBE) or heterozygous for F508del with a different disease causing mutation on the other allele.

HBE cells grown on Costar® Snapwell™ cell culture inserts were mounted in an Ussing chamber (Physiologic Instruments, Inc., San Diego, CA), and the transepithelial resistance and short-circuit current in the presence of a basolateral to apical Cl⁻ gradient ($I_{SC}$) were measured using a voltage-clamp system (Department of Bioengineering, University of Iowa, IA). Briefly, HBE cells were examined under voltage-clamp recording conditions ($V_{hold}$=0 mV) at 37° C. The basolateral solution contained (in mM) 145 NaCl, 0.83 $K_2HPO_4$, 3.3 $KH_2PO_4$, 1.2 $MgCl_2$, 1.2 $CaCl_2$), 10 Glucose, 10 HEPES (pH adjusted to 7.35 with NaOH) and the apical solution contained (in mM) 145 NaGluconate, 1.2 $MgCl_2$, 1.2 $CaCl_2$), 10 glucose, 10 HEPES (pH adjusted to 7.35 with NaOH).

Ussing Chamber Assay Procedure

A basolateral to apical membrane Cl⁻ concentration gradient was set up as follows. Normal Ringer's solution was used on the basolateral membrane, whereas apical NaCl was replaced by equimolar sodium gluconate (titrated to pH 7.4 with NaOH) to give a large Cl⁻ concentration gradient across the epithelium. Compound I was added either to the basolateral side 18-24 hrs prior to assay or to the apical side during the assay. Forskolin (10 µM) was added to the apical side during the assay to stimulate CFTR-mediated Cl⁻ transport. Chloride current was measured to assess the increase in functional CFTR in the cell membrane.

In Table 3, the following meanings apply: EC50: "+++" means <2 uM; "++" means between 2 uM to 5 uM; "+" means between 5 uM to 25 uM. % Efficacy: "+" means <25%; "++" means between 25% and 100%; "+++" means >100%.

TABLE 6

| Compound | HBE $EC_{50}$ (µM) | HBE Max Eff (%) |
| --- | --- | --- |
| Compound I | +++ | +++ |

Example 7

Compound I is a potent, efficacious, and selective next generation CFTR corrector that works by facilitating the processing and trafficking of F508del-CFTR protein to the cell surface, resulting in enhanced chloride transport.

The combination of Compound I and Compound II resulted in more than additive improvement in CFTR processing and trafficking compared to either CFTR corrector alone, suggesting that the two CFTR correctors act through different mechanisms of action, which act synergistically to increase the amount of F508del-CFTR delivered to the cell surface.

In addition, the more than additive effect of the combination of Compound I and Compound II on the processing and trafficking of CFTR suggests that the two CFTR correctors act through different mechanisms to result in the delivery of more CFTR protein to the cell surface compared to either CFTR corrector alone.

The triple combination of Compound I, Compound II, and Compound III enhanced chloride transport more than dual combinations at most concentrations of Compound I Compound 1 was administered to male Sprague Dawley rats as a single nominal intravenous (IV) dose of 3.0 mg/kg in a solution in 10% NMP, 15% EtOH, 35% PEG400, 10% Solutol, and 30% D5W. Compound 1 was also administered to male Sprague Dawley rats at single nominal oral dose (PO) of 3 mg/kg as a solution in 5% NMP, 30% PEG400, 10% TPGS, 5% PVP-K30 at 5 mL/kg dose volume.

The study design, sample tracking, data run design and individual plasma sample concentrations were stored using Watson LIMS software, Version 7.4.2 (Thermo Scientific Inc, Waltham, MA). Plasma concentration-time profiles of Compound 1 in Sprague Dawley rats at scheduled (nominal) sampling times were analyzed by noncompartmental pharmacokinetic methods using PK function within Watson LIMS software, Version 7.4.2 (Thermo Scientific Inc, Waltham, MA). Key pharmacokinetic parameters such as "area under the curve" (AUC), from the time of drug administration, time zero, extrapolated to infinity, clearance (CL), and Percent of oral bioavailability (% F) were determined. The AUC values were calculated using the linear trapezoidal rule.

In Table 7 below, Compound I is shown to have advantageous rat oral exposure (AUC) and oral bioavailability.

TABLE 7

| Compound | Rat iv CL (mL/min/kg) | Rat PO AUC (µg · hr/mL) | Rat PO AUC/dose (µg · hr/mL/mg/kg) | Rat % F |
|---|---|---|---|---|
| Compound I | 1.6 ± 0.4 | 23.5 ± 1.7 | 9.4 ± 0.7 | 84% |

Example 8: Safety and Efficacy Study 1 of Compound I

Part 1 with Healthy Subjects

In Part 1, safety and tolerability of Compound 1 at a total daily dose ranging from 20 mg to 800 mg of Compound I (e.g., 20 mg, 60 mg, 120 mg, 240 mg, 480 mg, and 800 mg) are studied in healthy subjects when administered alone and in TC (triple combination) with Compound II 100 mg qd and Compound III 150 mg q12h.

In the intrum data, single doses of Compound I up to 360 mg were safe and well tolerated; multiple doses of Compound I up to 340 mg for 10 days were safe and well tolerated; and multiple doses of Compound I up to 280 mg qd in TC (triple combo) with Compound II 100 mg qd and Compound III 150 mg q12h were safe and well tolerated after 14 days of dosing.

Part 2 with CF Subjects

In Part 2, evaluation of the safety, tolerability and efficacy of Compound I in combination with Compound II and Compound III in subjects with cystic fibrosis was studied in a randomized, double-blind, placebo- and Compounds II/III-controlled manner. Part 2 has two cohorts: Cohort A, involving subjects with F508del/MF (F/MF) genotypes (e.g., heterozygous for F508del with a second CFTR allele carrying a MF mutation described in Table B) (Part D) and Cohort B, involving subjects with F508del/F508del (F/F) genotype (Part E).

Part D was randomized, double-blind, placebo-controlled and evaluated Compound I in triple combo (TC) with Compound II and Compound III in subjects with CF having F/MF genotypes. Following a 4 week screening period, subjects with F508del/MF genotypes were randomized such that subjects were administered a TC of 50 mg qd, 100 mg qd or 200 mg qd of Compound I as well 100 mg qd of Compound II and 150 mg of Compound III q12h for 28 days followed by a double combination of Compound II and III for one week. Other subjects were administered a triple placebo for 28 days followed by a dual placebo for 1 week. After the 5 weeks of treatment, all subjects participated in a 4 week safety follow-up period.

Part E is randomized, double-blind, Compound II/Compound III double-combo-controlled and evaluates Compound I in triple combo (TC) with Compound II and Compound III in subjects with CF having F/F genotype. For the double combo of Compound II and III, subjects will be administered 50 mg every 12 hours ("q12h") or 100 mg once daily ("qd") of Compound II and 150 mg of Compound III q12h. Subjects who are in the treatment arms are administered 50 mg qd, 100 mg qd, 150 mg qd, 200 mg qd, or 250 mg qd of Compound I, 50 mg q12h or 100 mg qd of Compound II, and 150 mg of Compound III q12h for 28 days of treatment.

TABLE 8

Treatment Arms and Planned Doses for Part 2

| Part | Treatment/Control Arms | Compound I Dosage | Compound II Dosage | Compound III Dosage |
|---|---|---|---|---|
| Part D | TC-high | 200 mg qd | 100 mg qd | 150 mg q12 h |
|  | TC-mid | 100 mg qd | 100 mg qd | 150 mg q12 h |
|  | TC-low | 50 mg qd | 100 mg qd | 150 mg q12 h |
|  | Triple placebo[a] | Placebo | Placebo | Placebo |
| Part E[c] | TC-high | 250 mg qd | 100 mg qd | 150 mg q12 h |
|  | Compound II/Compound III | Placebo[b] | 100 mg qd | 150 mg q12 h |

[a]Triple placebo: subjects are administered with placebos for all 3 Compounds I, II and III.
[b]Placebo: subjects are administered with a placebo for Compound I, and 100 mg qd of Compound II and 150 mg q12 h of Compound III.
[c]In Part E, all subjects will also receive 100 mg qd of Compound II and IVA 150 mg q12 h during (1) a 4 week Run-in Period prior to the 4 week Treatment Period and (2) a 4 week Washout Period following the 4 week Treatment Period.

Primary endpoints for the study include: safety and tolerability assessments based on adverse events (AEs) and serious adverse events (SAEs) from baseline through safety follow-up (e.g., up to 28 days after last dose) after the treatment and absolute change in percent predicted forced expiratory volume in 1 second (ppFEV$_1$) from baseline through daily 29 Visit (±2 days). Secondary endpoints include: absolute change in sweat chloride concentrations from baseline through the Day 29 Visit (±2 days); relative change in ppFEV$_1$ from baseline through the Day 29 Visit (±2 days); absolute change in Cystic Fibrosis Questionnaire-Revised (CFQ-R) respiratory domain score from baseline at the Day 29 Visit (±2 days); PK parameters, area under the concentration time curve during a dosing (AUCtau), and observed pre-dose concentration (Ctrough) of Compounds I, II, and III from baseline through safety follow-up period.

Results of Part D

In Part D, as shown in the tables below, for 4 weeks of Compound I in triple combination with Compound II and Compound III in subjects heterozygous for F508del and a minimal function mutation (F/MF) with ages 18 and older resulted in statistically significant and clinically meaningful improvements in ppFEV$_1$ (7.8-13.8 percentage points) and sweat chloride (33.3-39.1 mmol/L).

In particular, at Day 29, there was a mean absolute improvement in ppFEV$_1$ of +11.1, +7.8, and +13.8 percentage points from baseline in those respectively receiving triple combination regimens of Compound I (50 mg qd), Compound II (100 mg qd) and Compound III (150 mg, q12h); Compound I (100 mg qd), Compound II (100 mg qd) and Compound III (150 mg, q12h); and Compound I (200 mg qd), Compound II (100 mg qd) and Compound III (150 mg, q12h). For those receiving placebo, there was a mean absolute change in ppFEV$_1$ of +0.0.

|  | Placebo N = 12 | Compound I (50 mg, qd)/ Compound II (100 mg, qd)/ Compound III (150 mg, q12 h) N = 10 | Compound I (100 mg, qd)/ Compound II (100 mg, qd)/ Compound III (150 mg, q12 h) N = 22 | Compound I (200 mg, qd)/ Compound II (100 mg, qd)/ Compound III (150 mg, q12 h) N = 21 |
|---|---|---|---|---|
| Baseline ppFEV1; Mean (SD) | 59.0 (14.9) | 56.4 (14.6) | 60.0 (15.5) | 59.4 (18.0) |
| Mean Absolute Within-Group Change | 0.0 (2.0) | 11.1 (2.1) | 7.8 (1.4) | 13.8 (1.4) |

-continued

|  | Placebo N = 12 | Compound I (50 mg, qd)/ Compound II (100 mg, qd)/ Compound III (150 mg, q12 h) N = 10 | Compound I (100 mg, qd)/ Compound II (100 mg, qd)/ Compound III (150 mg, q12 h) N = 22 | Compound I (200 mg, qd)/ Compound II (100 mg, qd)/ Compound III (150 mg, q12 h) N = 21 |
|---|---|---|---|---|
| from Baseline Through Day 29# (SD) | | | | |
| p-value (within-treatment)# | 0.9943 | <0.0001 | <0.0001 | <0.0001 |

All p-values are within group p-values based on mixed effect models; values expressed as 'Through Day 29' are the average of Day 15 and Day 29 measures.

At Day 29, there was a mean decrease in sweat chloride of −38.2, −33.2, and −39.1 mmol/L from baseline in those respectively receiving triple combination regimens of Compound I (50 mg qd), Compound II (100 mg qd) and Compound III (150 mg, q12h); Compound I (100 mg qd), Compound II (100 mg qd) and Compound III (150 mg, q12h); and Compound I (200 mg qd), Compound II (100 mg qd) and Compound III (150 mg, q12h). For those receiving placebo, there was a mean absolute decrease in sweat chloride of −2.2.

|  | Placebo N = 12 | Compound I (50 mg, qd)/ Compound II (100 mg, qd)/ Compound III (150 mg, q12 h) N = 10 | Compound I (100 mg, qd)/ Compound II (100 mg, qd)/ Compound III (150 mg, q12 h) N = 22 | Compound I (200 mg, qd)/ Compound II (100 mg, qd)/ Compound III (150 mg, q12 h) N = 21 |
|---|---|---|---|---|
| Baseline SwCl; Mean (SD) | 103.1 (8.2) | 103.1 (7.8) | 103.6 (12.2) | 103.9 (9.7) |
| Mean Absolute Within-Group Change from Baseline Through Day 29# (SD) | −2.2 (3.9) | −38.2 (4.2) | −33.2 (2.8) | −39.1 (2.9) |
| p-value (within-treatment)# | 0.5804 | <0.0001 | <0.0001 | <0.0001 |

All p-values are within group p-values based on mixed effect models; values expressed as 'Through Day 29' are the average of Day 15 and Day 29 measures.

A secondary endpoint in the triple combination study Part D measured mean absolute change in the respiratory domain of CFQ-Rat Day 29. The mean absolute improvements for patients who received the triple combination were 20.8 points (50 mg Compound I), 15.4 points (100 mg Compound I) and 25.7 points (200 mg Compound I). The improvement for those who received placebo was 4.2 points. The CFQ-R results reported are based on a mixed effect models not adjusted for baseline CFQR.

An overview of treatment emergent adverse events ("TEAE") after 29 days is provided below.

|  | Placebo N = 12 | Compound I (50 mg, qd)/ Compound II (100 mg, qd)/ Compound III (150 mg, q12 h) N = 10 | Compound I (100 mg, qd)/ Compound II (100 mg, qd)/ Compound III (150 mg, q12 h) N = 22 | Compound I (200 mg, qd)/ Compound II (100 mg, qd)/ Compound III (150 mg, q12 h) N = 21 |
|---|---|---|---|---|
| Subjects with any TFAE | 12 (100.00) | 9 (90.0) | 20 (90.9) | 17 (81.0) |
| Subjects with Severe TEAE | 1[a] | 1[c] | 1[d] | 0 |
| Subjects with Serious TEAE | 2[a,b] | 1[c] | 2[d,e] | 0 |
| Subjects with TEAE leading to treatment discontinuation | 0 | 0 | 2[f,g] | 0 |
| Subjects with TEAE leading to drug interruption | 0 | 0 | 0 | 2[h,j] |

[a]PEx;
[b]Haemoptysis;
[c]Jugular vein thrombosis, Pex and DIOS in one subject;
[d]PEx;
[e]PEx and influenza in one subject;
[f]Rash;
[g]Increased bilirubin;
[h]Increased bilirubin;
[j]Constipation.

In summary, the triple combination regimen in Part D of the study was generally well tolerated. The majority of adverse events were mild or moderate. Serious adverse events were reported in five patients: two patients in the placebo group (1 with hemoptysis and 1 with infective pulmonary exacerbation) and three patients in the triple combination groups (1 patient with infective pulmonary exacerbation, jugular vein thrombosis related to a central line and distal intestinal obstruction syndrome; 1 patient with infective pulmonary exacerbation and influenza; and 1 patient with infective pulmonary exacerbation) None of these serious adverse events were considered related to treatment and none resulted in treatment discontinuation. The most common adverse events (>10%), regardless of treatment group, were cough, sputum increased, infective pulmonary exacerbation, hemoptysis, headache, nasal congestion, nausea, oropharyngeal pain and pyrexia. Two patients discontinued treatment due to adverse events in the triple combination treatment groups (1 patient with rash and 1 patient with increased bilirubin without associated elevations in transaminases) and none in the placebo group. Upon discontinuing treatment, the rash resolved and the increased bilirubin returned to baseline. Two patients interrupted treatment due to adverse events in the triple combination groups (1 constipation and 1 increased bilirubin without associated elevations in transaminases); both events resolved when treatment was interrupted and both patients completed triple combination treatment without further incidence.

Compound I/Compound II/Compound III triple combinations were generally safe and well tolerated. There were 2 dose interruptions, both in the Compound I 200 mg dose group, one due to increased bilirubin and one due to constipation. There were 2 treatment discontinuations, both in the Compound I 100 mg dose group, one due to increased bilirubin and one due to rash. A total of 3 subjects treated with the TC had serious adverse events; 1 occurred at the end and 2 occurred after the triple combination treatment period. The most common adverse events (>10%), regardless of treatment group, were cough, sputum increased, infective pulmonary exacerbation, hemoptysis, headache, nasal congestion, nausea, oropharyngeal pain and pyrexia.

Example 9: Safety and Efficacy Study 2 of Compound I

Evaluation of the safety, tolerability and efficacy of Compound I in combination with Compound II and Compound III-d in subjects with cystic fibrosis was studied in a randomized, double-blind, placebo- and Compounds II/III- and Compound II/III-d-controlled manner, with two cohorts: Cohort A, involving subjects with F508del/MF (F/MF) genotypes (e.g., heterozygous for F508del with a second CFTR allele carrying a MF mutation described in Table 5B) and Cohort B, involving subjects with F508del/F508del (F/F) genotype.

As shown in Table 8 above, Part D is randomized, double-blind, placebo-controlled, and evaluated Compound I in TC with Compound II and Compound III in subjects with CF (F/MF genotypes). Part F is randomized, double-blind, placebo-controlled, and evaluates Compound I in TC with Compound II and Compound III-d in subjects with CF (F/MF genotypes).

TABLE 9

Treatment Arms and Planned Doses

| Part | Treatment/ Control Arms | Compound I Dosage | Compound II Dosage | Compound III Dosage | Compound III-d Dosage |
|---|---|---|---|---|---|
| Part D | TC-high | 200 mg qd | 100 mg qd | 150 mg q12 h | N/A |
| Part F | TC2-high | 200 mg qd | 100 mg qd | N/A | 150 mg qd |
| | Triple Placebo | Placebo | Placebo | | Placebo |

$^a$ Triple placebo: subjects are administered with placebos for all 3 Compounds I, II and III-d.

Primary endpoints for the study include: safety and tolerability assessments based on adverse events (AEs) and serious adverse events (SAEs) from baseline through safety follow-up (e.g., up to 28 days after last dose) after the treatment and absolute change in percent predicted forced expiratory volume in 1 second (ppFEV$_1$) from baseline through daily 29 Visit (±2 days). Secondary endpoints include: absolute change in sweat chloride concentrations from baseline through the Day 29 Visit (±2 days); relative change in ppFEV$_1$ from baseline through the Day 29 Visit (±2 days); absolute change in Cystic Fibrosis Questionnaire-Revised (CFQ-R) respiratory domain score from baseline at the Day 29 Visit (±2 days); PK parameters, area under the concentration time curve during a dosing (AUCtau), and observed pre-dose concentration (Ctrough) of Compounds I, II, and III from baseline through safety follow-up period.

Results of Part E

In Part E, all patients received a 4-week run-in of Compound II in combination with Compound III. Patients were then randomized to add either once-daily Compound I (200 mg) or placebo to Compound II and Compound III for four weeks. After the 4-week triple combination dosing period, all patients received four weeks of Compound II and Compound III, followed by a 4-week safety follow-up period.

As shown in the tables below, treatment for 4 weeks of Compound I in triple combination with Compound II and Compound III in subjects homozygous for F508del with ages 18 and older resulted in statistically significant and clinically meaningful improvements in ppFEV$_1$ (11.0 percentage points) and sweat chloride (39.6 mmol/L).

In particular, at Day 29, there was a mean absolute improvement in ppFEV$_1$ of +11.0 percentage points from baseline in those receiving triple combination regimens of Compound I (200 mg qd), Compound II (100 mg qd) and Compound III (150 mg, q12h). For those receiving placebo, there was a mean absolute change in ppFEV$_1$ of +0.4.

| | Compound II (100 mg, qd)/ Compound III (150 mg, q12 h) N = 7 | Compound I (200 mg, qd)/ Compound II (100 mg, qd)/ Compound III (150 mg, q12 h) N = 21 |
|---|---|---|
| Baseline ppFEV1; Mean (SD) | 62.8 (13.2) | 60.0 (15.1) |
| Mean Absolute Within-Group Change from Baseline Through Day 29$^\#$ (SD) | +0.4 (2.8) | +11.0 (1.5) |
| p-value (within-treatment)$^\#$ | 0.8869 | <0.0001 |

$^\#$All p-values are within group p-values based on mixed effect models; values expressed as 'Through Day 29' are the average of Day 15 and Day 29 measures.

At Day 29, there was a mean decrease in sweat chloride of −39.6 mmol/L from baseline in those receiving triple combination regimens of Compound I (200 mg qd), Compound II (100 mg qd), and Compound III (150 mg, q12h). For those receiving placebo, there was a mean absolute increase in sweat chloride of +0.8.

| | Compound II (100 mg, qd)/ Compound III (150 mg, q12 h) N = 7 | Compound I (200 mg, qd)/ Compound II (100 mg, qd)/ Compound III (150 mg, q12 h) N = 21 |
|---|---|---|
| Baseline SwCl; Mean (SD) | 99.5 (9.0) | 92.7 (11.1) |
| Mean Absolute Within-Group Change from Baseline Through Day 29$^\#$ (SD) | +0.8 (4.9) | −39.6 (2.8) |
| p-value (within-treatment)$^\#$ | 0.8712 | <0.001 |

$^\#$All p-values are within group p-values based on mixed effect models; values expressed as 'Through Day 29' are the average of Day 15 and Day 29 measures.

A secondary endpoint in the triple combination study Part E measured mean absolute change in the respiratory domain of CFQ-R at Day 29. The mean absolute improvements for patients who received the triple combination was 20.7 points. The improvement for those who received placebo was 5.2 points. The CFQ-R results reported are based on a mixed effect models not adjusted for baseline CFQR.

An overview of treatment emergent adverse events ("TEAE") after 29 days is provided below.

|  | Compound II (100 mg, qd)/ Compound III (150 mg, q12 h) N = 7 | Compound I (200 mg, qd)/ Compound II (100 mg, qd)/ Compound III (150 mg, q12 h) N = 21 |
|---|---|---|
| Subjects with any TEAE | 5 (71.4) | 20 (95.2) |
| Subjects with Severe TEAE | 1[a] | 1[c] |
| Subjects with Serious TEAE | 1[a] | 0 |
| Subjects with TEAE leading to treatment discontinuation | 1[b] | 1[d] |
| Subjects with TEAE leading to drug interruption | 1[b] | 1[c] |

[a]PEx
[b]Increased bilirubin
[c]Myopathy/increased CK and AST
[d]Chest pain

In summary, the triple combination regimen in Part E of the study was generally well tolerated. The majority of adverse events were mild or moderate. No serious adverse events were reported in the triple combination group and one serious adverse event (pulmonary exacerbation) was reported in the group that received placebo added to tezacaftor and ivacaftor. The most common adverse events occurring in at least two patients in any treatment group were sputum increased, cough, infective pulmonary exacerbation, fatigue, pyrexia, AST increased, CPK increased, chills, haemoptysis, ALT increased, respiration abnormal and sputum discoloured. There was one discontinuation in the triple combination group due to an adverse event (chest pain), and one patient interrupted then discontinued treatment in the group that received placebo added to tezacaftor and ivacaftor due to an adverse event (increased bilirubin without associated elevations in transaminases). One patient in the triple combination group interrupted treatment due to adverse events (myopathy and increased CPK, ALT and AST) that occurred in the tezacaftor/ivacaftor treatment period that followed triple combination dosing. The events resolved following interruption of treatment, and the patient subsequently restarted and completed treatment in the tezacaftor/ivacaftor period without any further incidence.

Results of Part F

In Part F, as shown in the tables below, 4 weeks of Compound I in triple combination with Compound II and Compound III-d in subjects heterozygous for F508del and a minimal function mutation (F/MF) with ages 18 and older resulted in statistically significant and clinically meaningful improvements in ppFEV$_1$ (11.7 percentage points) and sweat chloride (33.6 mmol/L).

In particular, at Day 29, there was a mean absolute improvement in ppFEV$_1$ of +11.7 percentage points from baseline in those receiving triple combination regimens of Compound I (200 mg qd), Compound II (100 mg qd) and Compound III-d (150 mg, qd). For those receiving triple placebo, there was a mean absolute change in ppFEV$_1$ of +1.2. For those in the Part D, "TC-high" arm discussed above, who received triple combination regimens of Compound I (200 mg qd), Compound II (100 mg qd) and Compound III (150 mg, q12h), there was a mean absolute change in ppFEV$_1$ of +13.8.

|  | Triple Placebo N = 8 | Compound I (200 mg, qd)/ Compound II (100 mg, qd)/ Compound III-d (150 mg, qd) N = 21 | PART D, TC-high - Compound I (200 mg, qd)/ Compound II (100 mg, qd)/ Compound III (150 mg, q12 h) N = 21 |
|---|---|---|---|
| Baseline ppFEV1; Mean (SD) | 60.7 (14.0) | 60.6 (17.5) | 59.4 (18.0) |
| Mean Absolute Within-Group Change from Baseline Through Day 29[#] (SE) | 1.2 (2.6) | 11.7 (1.6) | 13.8 (1.4) |
| p-value (within-treatment)[#] | 0.6407 | <0.0001 | <0.0001 |

[#]All p-values are within group p-values based on mixed effect models; values expressed as 'Through Day 29' are the average of Day 15 and Day 29 measures.

At Day 29, there was a mean decrease in sweat chloride of −33.6 mmol/L from baseline in those receiving triple combination regimens of Compound I (200 mg qd), Compound II (100 mg qd) and Compound III-d (150 mg, qd). For those receiving triple placebo, there was a mean absolute decrease in sweat chloride of −2.2. For those in Part D, TC-high who received triple combination regimens of Compound I (200 mg qd), Compound II (100 mg qd) and Compound III (150 mg, q12h), there was a mean absolute decrease in sweat chloride of −39.1.

|  | Triple Placebo N = 8 | Compound I (200 mg, qd)/ Compound II (100 mg, qd)/ Compound III-d (150 mg, qd) N = 21 | PART D, TC-high - Compound I (200 mg, qd)/ Compound II (100 mg, qd)/ Compound III (150 mg, q12 h) N = 21 |
|---|---|---|---|
| Baseline SwCl; Mean (SD) | 96.4 (11.5) | 100.8 (15.4) | 103.9 (9.7) |
| Mean Absolute Within-Group Change from Baseline Through Day 29[#] (SD) | 1.0 (4.6) | −33.6 (2.8) | −39.1 (2.9) |
| p-value (within-treatment)[#] | 0.8359 | <0.0001 | <0.0001 |

[#]All p-values are within group p-values based on mixed effect models; values expressed as 'Through Day 29' are the average of Day 15 and Day 29 measures.

A secondary endpoint in the triple combination study Part F measured mean absolute change in the respiratory domain of CFQ-R at Day 29. The mean absolute improvement for patients who received the triple combination with Compound III-d was 20.2 points. The improvement for those who received triple placebo was 20.2 points. The improvement for those in Part D, TC-high who received triple combination with Compound III was 25.7 points. The CFQ-R results reported are based on a mixed effect models not adjusted for baseline CFQR.

An overview of treatment emergent adverse events ("TEAE") after 29 days is provided below.

|  | Triple Placebo N = 8 | Compound I (200 mg, qd)/ Compound II (100 mg, qd)/ Compound III-d (150 mg, qd) N = 21 | PART D, TC-high - Compound I (200 mg, qd)/ Compound II (100 mg, qd)/ Compound III (150 mg, q12 h) N = 21 |
|---|---|---|---|
| Subjects with any TEAE | 6 (75.0) | 17 (81.0) | 17 (81.0) |
| Subjects with Severe TEAE | 0 | 0 |  |
| Subjects with Serious TEAE | 1[a] | 0 | 0 |
| Subjects with TEAE leading to treatment discontinuation | 0 | 1[b] | 0 |
| Subjects with TEAE leading to drug interruption | 0 | 0 | 2[c,d] |

[a]PEx
[b]Rash
[c]Increased bilirubin
[d]Constipation

In this Part F, the once-daily triple combination regimen of Compound I, Compound II, and Compound III-d was generally well tolerated, and the safety profile was similar to that observed in Part D above with triple combination regimen of Compound I, Compound II, and Compound III. The majority of adverse events were mild or moderate. A serious adverse event was reported in one patient in the placebo group (infective pulmonary exacerbation), and there were no serious adverse events in the triple combination group. The most common adverse events occurring in at least two patients in any treatment group were cough, nausea, oropharyngeal (throat) pain, infective pulmonary exacerbation, nasal congestion, productive cough, sputum increased, chest pain, paranasal sinus discomfort, upper respiratory tract infection and vomiting. There was one discontinuation in the triple combination group due to an adverse event (rash). Following treatment discontinuation, the rash resolved.

A summary of the results of Parts D, E and F is shown below:

|  | Compound I (200 mg) + Compound II/ Compound III N = 21 (F/MF) (Part D) | Compound I (200 mg) + Compound II/ Compound III N = 21 (F/F) (Part E) | Compound I (200 mg) + Compound II/ Compound III-d N = 21 (F/MF) (Part F) |
|---|---|---|---|
| ppFEV1 | | | |
| Baseline ppFEV1; Mean (SD) | 59.4 (18.0) | 60.0 (15.1) | 60.6 (17.5) |
| LS Mean Change (SE) | 13.8 (1.4) | 11.0 (1.5) | 11.7 (1.6) |
| SwCl | | | |
| Baseline SwCl; Mean (SD) | 103.9 (9.7) | 92.7 (11.1) | 100.8 (15.4) |
| LS Mean Change (SE) | −39.1 (2.9) | −39.6 (2.8) | −33.6 (2.8) |
| CFQR* | | | |
| Baseline CFQR; Mean (SD) | 61.1 (17.5) | 71.2 (17.3) | 63.8 (18.2) |
| LS Mean Change (SE) | 25.7 (3.7) | 20.7 (4.0) | 20.2 (4.3) |

*MMRM without adjustment of baseline CFQR

Example 10: Safety and Efficacy Study 3 of Compound I

Study 3A-1 will be a randomized, double-blind, controlled Phase 3 study to evaluate a fixed-dose combination of Compound I (200 mg) with Compound II (100 mg) and Compound III (150 mg) in the morning followed by Compound III (150 mg) in the evening, or placebo in combination with Compound II and Compound III for 4 weeks of treatment in patients ages 12 years or older who are homozygous for the F508del mutation (F/F). Approximately ½ of the patients will receive Compound I, Compound II, and Compound III, and approximately ½ of the will receive placebo, Compound II, and Compound III. All patients will receive Compound II in combination with Compound III during a 4-week run-in prior to the start of the triple combination treatment period. The primary endpoint of the study is the mean absolute change in lung function (ppFEV$_1$) from baseline (end of the 4-week Compound II/Compound III run-in) at week four of treatment with Compound I in combination with Compound II and Compound III compared to those who received placebo, Compound II and Compound III.

Study 3B-1 will be a randomized, double-blind, placebo-controlled Phase 3 study to evaluate a fixed-dose combination of Compound I (200 mg), Compound II (100 mg) and Compound III (150 mg) in the morning followed by Compound III (150 mg) in the evening, or triple placebo, for a total of 24 weeks of treatment in patients ages 12 and older who are heterozygous for the F508del mutation and an MF mutation (F/MF subjects). The primary endpoint of the study will be the mean absolute change in lung function (ppFEV1) from baseline at week four of triple combination treatment compared to placebo.

In Study 3A-2, the following TC and DC arms to evaluate a fixed-dose combination of Compound I (200 mg) with Compound II (100 mg) and Compound III-d (150 mg) (qd) will be studied in subjects with cystic fibrosis (CF) who are homozygous for the F508del mutation (F/F). The total study duration is approximately 16 weeks (4 weeks for screening, followed by 4 weeks for the Compound II/Compound III Run-in Period, followed by 4 weeks for the Treatment Period, which is followed by 4 weeks for the safety follow-up period). In the Compound II/Compound III Run-in Period, all subjects will receive Compound II 100 mg once daily (qd)/Compound III 150 mg every 12 hours (q12h). After completing the Compound II/Compound III Run-in Period, subjects will be randomized to the TC arm or DC arm for the Treatment Period. The Treatment arms and doses to be evaluated are shown in the table below.

| | Run-in Period | | | Treatment Period | | | | |
|---|---|---|---|---|---|---|---|---|
| Treatment Arm | Compound I Dose | Compound II Dose | Compound III Dose | Treatment Arm | Compound I Dose | Compound II Dose | Compound III-d Dose | Compound III Dose |
| Triple Combo (TC) Low | 0 mg | 100 mg qd | 150 mg q12 h | Triple Combo (TC) Low | 100 mg qd | 100 mg qd | 150 mg q12 h | 0 mg |
| High | | | | Triple Combo (TC) High | 200 mg qd | 100 mg qd | 150 mg q12 h | 0 mg |
| Compound II/ Compound III (DC) | 0 mg | 100 mg qd | 150 mg q12 h | Compound II/ Compound III | 0 mg | 100 mg qd | 0 mg | 150 mg q12 h |

In Study 3B-2, the following TC and DC arms to evaluate a fixed-dose combination of Compound I (200 mg) with Compound II (100 mg) and Compound III-d (150 mg) (qd) will be studied in subjects with cystic fibrosis (CF) who are heterozygous for the F508del mutation and an MF mutation (F/MF subjects). The total study duration is approximately 32 weeks (4 weeks for the screening period, followed by 24 weeks for the Treatment Period, which is followed by 4 weeks for the safety follow-up period). Unlike in Study 3A, there is no Run-in Period in Study 3B. Subjects will be randomized to the TC arm or triple placebo arm. The doses to be evaluated are shown in the table below.

| Treatment Arms and Doses | | | |
|---|---|---|---|
| Treatment Arm | Compound I Dose | Compound II Dose | Compound III-d Dose |
| TC Low | 100 mg qd | 100 mg qd | 150 mg q12 h |
| TC High | 200 mg qd | 100 mg qd | 150 mg q12 h |
| Triple placebo | 0 mg | 0 mg | 0 mg | q12 h: every 12 hours;
qd: once daily;
TC: triple combination

Example 11: Safety and Efficacy Study 4 of Compound I

To evaluate the long-term safety and efficacy of Compound I, in Study 4, patients who complete the Treatment Period in Study 3A or 3B will receive the TC at the same doses evaluated in Study 3A or 3B. The total study duration is approximately 100 weeks (including a 96-week Treatment Period (not including the 4 weeks for Study 3A or 3B) followed by a 4 week safety follow-up period).

Other Embodiments

The foregoing discussion discloses and describes merely exemplary embodiments of this disclosure. One skilled in the art will readily recognize from such discussion and from the accompanying drawings and claims, that various changes, modifications and variations can be made therein without departing from the spirit and scope of this disclosure as defined in the following claims.

The invention claimed is:

1. A method of treating cystic fibrosis comprising administering to a patient in need thereof:

(a) 200 mg once daily of crystalline Form A of Compound I:

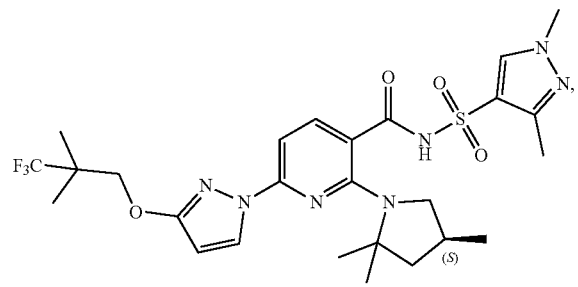

(b) 100 mg once daily of amorphous Compound II:

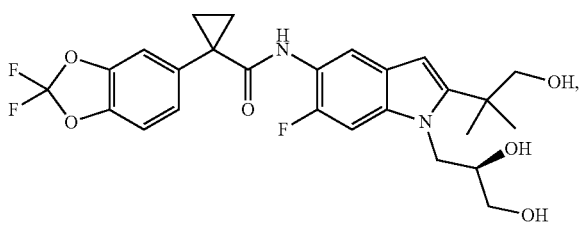 [SMILES: CC(C)(CO)c1cc2cc(NC(=O)C3(c4ccc5c(c4)OC(F)(F)O5)CC3)c(F)cc2n1C[C@@H](O)CO]

and (c) 150 mg per dose twice daily of amorphous Compound III:

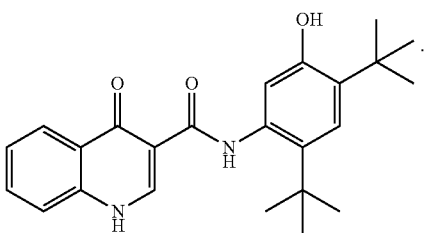 [SMILES: CC(C)(C)c1cc(C(C)(C)C)c(NC(=O)c2c[nH]c3ccccc3c2=O)cc1O]

2. A method of treating cystic fibrosis comprising administering to a patient in need thereof:
(a) 100 mg once daily of crystalline Form A of Compound I:

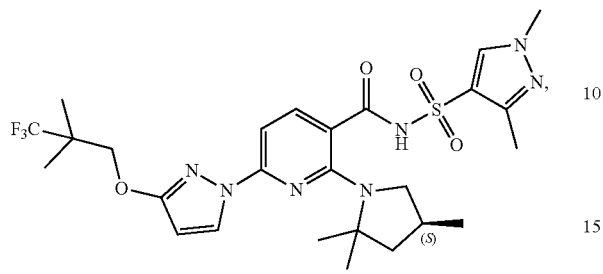

(b) 50 mg once daily of amorphous Compound II:

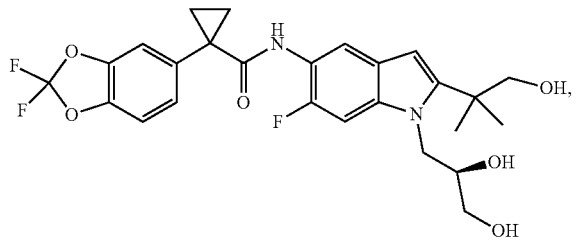 [SMILES: CC(C)(CO)c1cc2cc(NC(=O)C3(c4ccc5c(c4)OC(F)(F)O5)CC3)c(F)cc2n1C[C@@H](O)CO]

and
(c) 75 mg per dose twice daily of amorphous Compound III:

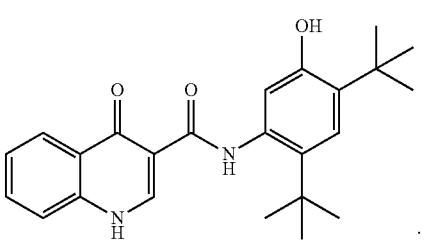 [SMILES: CC(C)(C)c1cc(C(C)(C)C)c(NC(=O)c2c[nH]c3ccccc3c2=O)cc1O]

3. The method of claim 1, wherein the method comprises administering 200 mg of Compound I, 100 mg of Compound II, and 150 mg of Compound III; followed by administering 150 mg of Compound III 12 hours later.

4. The method of claim 2, wherein the method comprises administering 100 mg of Compound I, 50 mg of Compound II, and 75 mg of Compound III; followed by administering 75 mg of Compound III 12 hours later.

* * * * *